US006280738B1

(12) United States Patent
Tai et al.

(10) Patent No.: US 6,280,738 B1
(45) Date of Patent: Aug. 28, 2001

(54) NON-IGA FC BINDING FORMS OF THE GROUP B STREPTOCOCCAL β ANTIGENS

(75) Inventors: Joseph Y. Tai, Fort Washington, PA (US); Milan S Blake, Fulton, MD (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 08/923,992

(22) Filed: Sep. 5, 1997

Related U.S. Application Data

(60) Provisional application No. 60/024,707, filed on Sep. 6, 1996.

(51) Int. Cl.[7] ........................ A61K 39/09; A61K 39/385; C07K 14/315

(52) U.S. Cl. .................................. 424/197.11; 424/190.1; 424/244.1; 424/282.1; 424/831; 514/54; 530/403; 530/825

(58) Field of Search ............................ 424/190.1, 197.11, 424/244.1, 282.1, 831; 514/54; 530/350, 402, 403, 825

(56) References Cited

U.S. PATENT DOCUMENTS 4,757,134 7/1988 Blake et al. ......................... 530/350
5,595,740 1/1997 Brady ............................... 424/190.1
5,644,030 7/1997 Faulmann ............................ 530/350

FOREIGN PATENT DOCUMENTS

WO 84/02194 6/1984 (WO) .

OTHER PUBLICATIONS

Anthony, B.F. et al., "Nonimmune Binding of Human Immunoglobulin A to Type II Group B Streptococci," *Infect. Immun. 58*(*6*):1789–1795 (1990).

Baker, C.J. et al., "Immunogenicity of Polysaccharides from Type III, Group B Streptococcus," *J. Clin. Invest. 61*(*4*):1107–1110 (1978).

Brady, L.J. and M.D.P. Boyle, "Identification of Non–Immunoglobulin A–Fc–Binding Forms and Low–Molecular-Weight Secreted Forms of the Group B Streptococcal β Antigen," *Infect. Immun. 57*(*5*):1573–1581 (1989).

Chun, C.S.Y. et al., "Group B Streptococcal C Protein–Associated Antigens: Association with Neonatal Sepsis," *J. Infect. Dis. 163*(*4*):786–791 (1991).

Cleat, P.H. and K.N. Timmis, "Cloning and Expression in *Escherichia coli* of the Ibc Protein Genes of Group B Streptococci: Binding of Human Immunoglobulin A to the Beta Antigen," *Infect. Immun. 55*(*5*):1151–1155 (1987).

Fischer, G. et al., "From the National Institute of Allergy and Infectious Diseases, Summary of the National Institutes of Health Workshop on Group B Streptococcal Infection," *J. Infect. Dis. 148*(*1*):163–166 (1983).

Flores, A.E. et al., "Antibody profiles to the group B streptococcal beta antigen in maternal and infant paired sera," *APMIS 101*(*1*):41–49 (1993).

Hedén, L.–O. et al., "Molecular characterization of an IgA receptor from group B streptococci: sequence of the gene, identification of a proline–rich region with unique structure and isolation of N–terminal fragments with IgA–binding capacity," *Eur. J. Immunol. 21:*1481–1490 (1991).

Jerlström, P.G. et al., "The IgA–binding β antigen of the c protein complex of Group B streptococci: sequence determination of its gene and detection of two binding regions," *Mol. Microbiol. 5*(*4*):843–849 (1991).

Kvam, A.I. et al., "Binding of human IgA to HCl–extracted c protein from group B streptococci (GBS)," *APMIS 100*(*12*):1129–1132 (1992).

Lindahl, G. et al., "Characterization of an IgA receptor from group B streptococci: specificity for serum IgA," *Eur. J. Immunol. 20*(*9*):2241–2247 (1990).

Liszewski, M.K. and J.P. Atkinson, "The Complement System," in: *Fundamental Immunology,* Third Edition, Paul, W.E., Ed., Raven Press, New York; pp. 933–935 (1993).

Madoff, L.C. et al., "Protection of Neonatal Mice from Group B Streptococcal Infection by Maternal Immunization with Beta C Protein," *Infect. Immun. 60*(*12*):4989–4994 (1992).

Michel, J.L. et al., "Cloned Alpha and Beta C–Protein Antigens of Group B Streptococci Elicit Protective Immunity," *Infect. Immun. 59*(*6*):2023–2028 (1991).

Michel, J.L. et al., "Large, identical, tandem repeating units in the C protein alpha antigen gene, bca, of group B streptococci," *Proc. Natl. Acad. Sci. USA 89*(*21*):10060–10064 (1992).

Russell–Jones, G.J. et al., "A Surface Receptor Specific for Human IgA on Group B Streptococci Possessing the Ibc Protein Antigen," *J. Exp. Med. 160*(*5*):1467–1475 (1984).

(List continued on next page.)

*Primary Examiner*—Christopher L. Chin
*Assistant Examiner*—James L. Grun
(74) *Attorney, Agent, or Firm*—C. Joseph Faraci

(57) ABSTRACT

A-$X_{202}X_{203}X_{204}X_{205}X_{206}X_{207}X_{208}X_{209}X_{210}X_{211}X_{212}X_{213}$-B, wherein A represents amino acid residues 38–201 of SEQ ID NO: 2, B represents a sequence starting from amino acid 214 of SEQ ID NO: 2 and terminating at an amino acid between residues 1131 and 1164, inclusive, of SEQ ID NO: 2, and $X_{202}$ through $X_{213}$ are each selected independently from Ala, Val, Leu, Ile, Pro, Met, Phe, Trp, a bond, or a wild-type amino acid as found at a corresponding position of residues 202–213 of SEQ ID NO: 2, with the proviso that at least one of $X_{202}$ through $X_{213}$, inclusive, is other than the wild type amino acid found at the corresponding position of SEQ ID NO: 2. The LPXTG motif, as found in the native protein at amino acid residues corresponding to residues 1132–1136 of SEQ ID NO: 2, may be deleted in the sequence of the mutant Cβ protein. The mutant Cβ protein is conjugated to a streptococcal capsular polysacharide in a vaccine composition, also having an acceptable pharmaceutical carrier, for use in a method of including an immune response in an animal. Nucleic acid molecules encoding the mutant protein, vectors containing these molecules, and host cells transformed therewith are also disclosed.

12 Claims, 35 Drawing Sheets

OTHER PUBLICATIONS

Russell–Jones, G.J. and E.C. Gotschlich, "Identification of Protein Antigens of Group B Streptococci, with Special Reference to the Ibc Antigens," *J. Exp. Med. 160*(*5*):1476–1484 (1984).

Jerlström, P.G. et al., "Identification of an Immunoglobulin A Binding Motif Located in the β–Antigen of the c Protein Complex of Group B Streptococci," *Infection & Immunity 64*(*7*):2787–2793 (Jul. 1996).

Madoff, L.C. et al., "Maternal Immunization of Mice with Group B Streptococcal Type III Polysaccharide–Beta C Protein Conjugate Elicits Protective Antibody to Multiple Serotypes," *J. Clin. Invest. 94:*286–292 (1994).

International Search Report for International Application No. PCT/US97/15319, mailed Dec. 22, 1997.

Bowie, J.U. et al., "Deciphering the Message in Protein Sequences: Tolerance to Amino Acid Substitutions," *Science 247:*1306–1310 (Mar. 1990).

Navarre, W.W. and Schneewind, O., "Proteolytic cleavage and cell wall anchoring at the LPXTG motif of surface proteins in Gram–positive bacteria," *Mol. Microbiol. 14:*115–121 (Oct. 1994).

Schneewind, O. et al., "Structure of the Cell Wall Anchor of Surface Proteins in *Staphylococcus aureus,*" *Science 268:*103–106 (Apr. 1995).

```
AAGCTTAGCCTTGTCAATAATCACAAATTTGTAGATCACTTCCTTTTTAGGACTGTAAAGCATCCTAATTACTTTTTAAATATATTACCAGAACTAGTTGGTTTGGCCCTGGTGAGTCAT  120

GCTTATGTGACATTCATCTTTATTTTTCCTGTCTATGCGGTTATTCTTTATCAAAGAATAGCAGAGGAAGAAAAATTATTGCAGGAAGTTATTATTCCGAATGGAAGAATGAAAGGTTAA  240

                                                                                                   M  F  K  S  N  Y  E  R  K  M  R  Y  S  I    -24
AAATAATATACCCAATTTAATATGCAGTTCATATTGGAAGGGTATACTGTAGATAAATAAAATATTGGAGGATATCGATATGTTTAAATCTAATTATGAAAGAAAAATGCGTTATTCCAT  360
                                                                                                 └─►S
 R  K  F  S  V  G  V  A  S  V  A  V  A  S  L  F  M  G  S  V  A  H  A  S  E  L  V  K  D  D  S  V  K  T  T  E  V  A  A  K    17
TCGTAAATTTAGTGTAGGAGTAGCTAGTGTAGCGGTAGCTAGTTTGTTCATGGGAAGCGTTGCTCATGCAAGTGAGCTTGTAAAGGACGATAGTGTGAAGACTACCGAGGTTGCAGCTAA  480
                                                                      └─►P
 P  Y  P  S  M  A  Q  T  D  Q  G  N  N  S  S  S  S  E  L  E  T  T  K  M  E  I  P  T  T  D  I  K  K  A  V  E  P  V  E  K    57
GCCCTATCCAAGTATGGCTCAAACAGATCAAGGAAATAATTCATCATCCTCGGAACTTGAGACAACAAAGATGGAAATTCCTACAACAGACATAAAAAAAGCTGTTGAACCGGTCGAGAA  600

 T  A  G  E  T  S  A  T  D  T  G  K  R  E  K  Q  L  Q  Q  W  K  N  N  L  K  N  D  V  D  N  T  I  L  S  H  E  Q  K  N  E    97
AACAGCTGGGGAAACATCTGCCACTGATACTGGAAAACGAGAGAAACAATTACAACAATGGAAAAATAATCTAAAAAATGATGTGGATAACACAATTCTATCTCATGAACAGAAAAATGA  720

 F  K  T  K  I  D  E  T  N  D  S  D  A  L  L  E  L  E  N  Q  F  N  E  T  N  R  L  L  H  I  K  Q  H  E  E  V  E  K  D  K   137
GTTTAAAACAAAAATTGATGAAACAAATGATTCTGATGCATTATTAGAATTAGAAAATCAATTTAACGAAACTAATAGACTGTTACACATCAAACAACATGAAGAAGTTGAGAAAGATAA  840

 K  A  K  Q  Q  K  T  L  K  Q  S  D  T  K  V  D  L  S  N  I  D  K  E  L  N  H  Q  K  S  Q  V  E  K  M  A  E  Q  K  G  I   177
GAAAGCTAAGCAACAGAAAACTCTGAAACAGTCAGATACGAAAGTAGATCTAAGCAATATTGACAAAGAGCTTAATCATCAAAAAAGTCAAGTTGAAAAAATGGCAGAGCAAAAGGGAAT  960
                                              └─►Bgl II
 T  N  E  D  K  D  S  M  L  K  K  I  E  D  I  R  K  Q  A  Q  Q  A  D  K  K  E  D  A  E  V  K  V  R  E  E  L  G  K  L  F   217
CACAAATGAAGATAAAGATTCTATGCTGAAAAAAATCGAAGATATTCGTAAACAAGCTCAACAAGCAGATAAAAAAGAAGATGCCGAAGTAAAGGTTCGTGAAGAACTAGGTAAACTCTT 1080

 S  S  T  K  A  G  L  D  Q  E  I  Q  E  H  V  K  K  E  T  S  S  E  E  N  T  Q  K  V  D  E  H  Y  A  N  S  L  Q  N  L  A   257
TAGTTCAACTAAAGCTGGTCTGGATCAAGAAATTCAAGAGCATGTGAAGAAAGAAACGAGTAGTGAGGAAAATACTCAGAAAGTTGATGAACACTATGCTAATAGCCTTCAGAACCTTGC 1200
```

FIG.1A

Q K S L E E L D K A T T N E Q A T Q V K N Q F L E N A Q K L K E I Q P L I K E T 297
TCAAAAATCTCTTGAAGAACTAGATAAGGCAACTACCAATGAACAAGCTACACAAGTTAAAAATCAATTCTTAGAAAACGCTCAAAAGCTCAAAGAAATACAACCTCTTATCAAAGAAAC 1230

N V K L Y K A M S E S L E Q V E K E L K H N S E A N L E D L V A K S K E I V R E 337
GAATGTGAAATTGTATAAGGCTATGAGTGAGAGCTTGGAGCAGGTTGAGAAGGAATTAAAACATAATTCGGAAGCTAATTTAGAAGATTTGGTTGCGAAATCTAAAGAAATCGTAAGAGA 1440

Y E G K L N Q S K N L P E L K Q L E E E A H S K L K Q V V E D F R K K F K T S E 377
ATACGAAGGAAAACTTAATCAATCTAAAAATCTTCCAGAATTAAAGCAACTAGAAGAGGAAGCTCATTCGAATGGGAAACAAGTTGTGGAGGATTTTAGAAAAAAATTTAAAACGTCAGA 1560

Q V T P K K R V K R D L A A N E N N Q Q K I E L T V S P E N I T V Y E G E D V K 417
GCAAGTGACACCAAAAAAACGTGTCAAACGAGATTTAGCTGCTAATGAAAATAATCAACAAAAGATTGAGTTAACAGTTTCACCAGAGAATATCACTGTATATGAAGGTGAAGACGTGAA 1680
(→ B)

F T V T A K S D S K T T L D F S D L L T K Y N P S V S D R I S T N Y K T N T D N 457
ATTTACAGTCACAGCTAAAAGTGATTCGAAGACGACGTTGGACTTCAGTGATCTTTTAACAAAATATAATCCGTCTGTATCAGATAGAATTAGTACAAATTATAAGACTAACACGGATAA 1800

H K I A E I T I K N L K L N E S Q T V T L K A K D D S G N V V E K T F T I T V Q 497
TCATAAGATTGCCGAAATCACTATCAAGAATTTGAAGCTAAATGAAAGTCAAACAGTGACTCTAAAAGCTAAAGATGATTCTGGCAATGTAGTTGAAAAAACATTCACTATTACAGTGCA 1920

K K E E K Q V P K T P E Q K D S K T E E K V P Q E P K S N D K N Q L Q E L I K S 537
AAAGAAAGAGGAGAAACAAGTTCCTAAAACACCAGAGCAGAAAGATTCTAAAACGGAAGAAAAGGTTCCTCAAGAACCAAAATCAAATGACAAGAATCAATTACAAGAGTTGATTAAATC 2040

A Q Q E L E K L E K A I K E L M E Q P E I P S N P E Y G I Q K S I W E S Q K E P 577
AGCTCAACAAGAACTGGAAAAGTTAGAAAAAGCAATAAAAGAATTAATGGAGCAACCAGAGATTCCATCCAATCCAGAGTATGGTATTCAAAAATCTATTTGGGAGTCACAAAAAGAGCC 2160

I Q E A I T S F K K I I G D S S S K Y Y T E H Y F N K Y K S D F M N Y Q L H A Q 617
TATCCAGGAAGCCATAACAAGTTTTAAGAAGATTATTGGTGATTCATCTTCAAAATACTACACAGAGCACTATTTTAACAAATATAAATCTGATTTTATGAATTATCAACTTCATGCACA 2280

FIG.1B

```
 M  E  M  L  T  R  K  V  V  Q  Y  M  N  K  Y  P  D  N  A  E  I  K  K  I  F  E  S  D  M  K  R  T  K  E  D  N  Y  G  S  L   657
AATGGAGATGCTGACTAGAAAAGTGGTTCAGTATATGAACAAATATCCTGATAATGCAGAAATTAAAAAGATATTTGAGTCAGATATGAAGAGAACGAAAGAAGATAATTACGGAAGTTT  2400

 E  N  D  A  L  K  G  Y  F  E  K  Y  F  L  T  P  F  N  K  I  K  Q  I  V  D  D  L  D  K  K  V  E  Q  D  Q  P  A  P  I  P   697
AGAAAATGATGCTTTGAAAGGCTATTTTGAGAAATATTTCCTTACACCATTTAATAAAATTAAGCAGATTGTAGATGATTTGGATAAAAAAGTAGAACAAGATCAGCCAGCACCAATTCC  2520

 E  N  S  E  M  D  Q  A  K  E  D  A  K  I  A  V  S  K  Y  M  S  K  V  L  D  G  V  H  Q  H  L  Q  K  K  N  N  S  K  I  V   737
GGAAAATTCAGAAATGGATCAGGCTAAGGAAAAGGCTAAGATTGCTGTATCGAAGTATATGAGTAAGGTTTTAGATGGAGTTCATCAACATCTGCAGAAGAAAAATAACAGTAAAATTGT  2640
                                                                                                   Pst I

 D  L  F  K  E  L  E  A  I  K  Q  Q  T  I  F  D  I  D  N  A  K  T  E  V  E  I  D  N  L  V  H  D  A  F  S  K  M  N  A  T   777
TGATCTTTTTAAGGAACTTGAAGCGATTAAACAACAAACTATTTTTGATATTGACAATGCAAAGACTGAAGTAGAGATTGATAACTTAGTACACGATGCATTCTCAAAAATGAATGCTAC  2760

 V  A  K  F  Q  K  G  L  E  T  N  T  P  E  T  P  D  T  P  K  I  P  E  L  P  Q  A  P  D  T  P  Q  A  P  D  T  P  H  V  P   817
TGTTGCTAAATTTCAAAAAGGTCTAGAGACAAATACGCCAGAAACTCCAGATACACCGAAGATTCCAGAGCTACCTCAAGCCCCAGATACACCGCAGGCTCCAGACACACCGCATGTTCC  2880
                                      Wr1                                                                      Wr2

 E  S  P  K  A  P  E  A  P  R  V  P  E  S  P  K  T  P  E  A  P  H  V  P  E  S  P  K  A  P  E  A  P  R  V  P  E  S  P  K   857
GGAATCACCAAAGGCCCCAGAAGCACCGCGTGTTCCGGAATCACCAAAGACTCCAGAAGCACCGCATGTTCCGGAATCACCAAAGGCCCCAGAAGCACCGCGTGTTCCGGAATCACCAAA  3000
                                                                Wr3

 T  P  E  A  P  H  V  P  E  S  P  K  T  P  E  A  P  K  I  P  K  P  P  K  T  P  D  V  P  K  L  P  D  V  P  K  L  P  D  V   897
GACTCCAGAAGCACCGCATGTTCCGGAATCACCAAAGACTCCAGAAGCACCAAAGATTCCGAAACCCCCTAAGACTCCAGACGTCCCTAAGCTTCCAGACGTCCCTAAGCTTCCAGACGT  3120
             Wr4                                                                       Wr5

 P  K  L  P  D  A  P  K  L  P  D  G  L  N  K  V  G  N  A  V  F  T  S  T  D  G  N  T  K  V  T  V  V  F  D  K  P  T  D  A   937
CCCTAAGCTTCCAGATGCACCGAAGTTACCAGATGGGTTAAATAAAGTTGGACAAGCAGTATTTACATCAACTGATGGAAATACTAAGGTTACGGTTGTATTTGATAAACCTACAGATGC  3240
                                      Wn

 D  K  L  H  L  K  E  V  T  T  K  E  L  A  D  K  I  A  H  K  T  G  G  G  T  V  R  V  F  D  L  S  L  S  K  G  G  K  E  T   977
TGATAAGTTACATCTCAAGGAAGTAACGACGAAAGAGTTGGCTGATAAAATTGCTCATAAAACAGGAGGAGGAACAGTTCGTGTGTTTGACTTATCTCTTTCTAAAGGAGGCAAGGAAAC  3360
```

FIG.1C

```
 H  V  D  G  E  R  T  V  R  L  A  L  G  N  T  G  S  D  V  H  V  Y  H  V  K  E  N  G  D  L  E  R  I  P  S  K  V  E  N  G   1017
ACATGTCAATGGAGAACGAACTGTTCGGCTCGCGCTTGGGCAGACTGGCTCAGATGTTCACGTCTATCACGTAAAGGAAAATGGCGACCTTGAGCGTATTCCTTCTAAAGTTGAAAATGG   3480

 Q  V  V  F  K  T  N  H  F  S  L  F  A  I  K  T  L  S  K  D  Q  N  V  T  P  P  K  Q  T  K  P  S  T  Q  G  S  Q  V  E  I   1057
GCAAGTTGTTTTTAAAACGAACCACTTCAGTTTGTTTGCGATTAAGACACTTTCTAAGGATCAAAATGTTACTCCACCGAAGCAGACTAAACCTTCTACCCAAGGCAGTCAAGTAGAGAT   3600

 A  E  S  Q  T  G  K  F  Q  S  K  A  A  N  H  K  A  L  A  T  G  N  E  T  V  A  K  G  N  P  T  S  T  T  E  K  K  L  P  Y   1097
TGCAGAGAGTCAAACTGGAAAATTCCAGAGTAAAGCAGCTAATCATAAAGCACTGGCTACTGGAAATGAAACAGTGGCAAAAGGAAATCCTACATCAACAACGGAAAAGAAATTGCCATA   1720
                                                                                                                 └─►M

 T  G  V  A  S  N  L  V  L  E  I  M  G  L  L  G  L  I  G  T  S  F  I  A  M  K  R  R  K  S                                  1127
TACAGGAGTGGCATCTAATCTAGTTCTTGAAATTATGGGTCTCCTTGGTTTGATTGGAACTTCATTCATCGCAATGAAAAGAAGAAAATCATGATTCAGTTTTTTAAAAATATCCACTTT   3840

CGATATCTAGCATTTGATTGGTTATCTGTGGATGATTCTAAAGATGTTACCTATCGTTGGTATGTAACAATTATAAGTCATTTCATATAAAAGAGGCTCTTTGTCAACTGTAGTTGGTTG   3960

AAACAAGGCTACAAACTAGAAAGGACGCATTTTGTCCTTTCTTTTTGATGTTGAGGGCAATGAAAATACGCTTTTTGAAGTTTTCAAAATTCCGAAAACTAAAGATATTGTATTTGAAAA   4080

GTTTAATGAGATGATTAGTTGCTTCCAATTTTGCGTTGGAGTAGGTTTACTGAAGGACGTTGACGATATTCTCTTTGCTTTTGAGAATGATTTTAAAGATAGTCTGAAAAAGAGGATGAA   4200
```

```
DGB2R -> 1-phase Translation
DNA sequence     3406 b.p.   agatctcgatcc ... tcgagcaccacc   linear

1    /    1                               31   /   11
aga tct cga tcc cgc gaa att aat acg act cac tat agg gga att gtg agc gga taa caa
arg ser arg ser arg glu ile asn thr thr his tyr arg gly ile val ser gly OCH gln
61   /   21                               91   /   31
ttc ccc tct aga aat aat ttt gtt taa ctt taa gaa gga gat ata cat atg AGT GAG CTT
phe pro ser arg asn asn phe val OCH leu OCH glu gly asp ile his met ser glu leu
121  /   41                               151  /   51
GTA AAG GAC GAT AGT GTG AAG ACT ACC GAG GTT GCA GCT AAG CCC TAT CCA AGT ATG GCT
val lys asp asp ser val lys thr thr glu val ala ala lys pro tyr pro ser met ala
181  /   61                               211  /   71
CAA ACA GAT CAA GGA AAT AAT TCA TCA TCC TCG GAA CTT GAG ACA ACA AGG ATG GAA ATT
gln thr asp gln gly asn asn ser ser ser ser glu leu glu thr thr arg met glu ile
241  /   81                               271  /   91
CCT ACA ACA CAC ATA AAA AAA GCT GTT GAA CCG GTC GAG AAA ACA GCT GGG GAA ACA TCT
pro thr thr asp ile lys lys ala val glu pro val glu lys thr ala gly glu thr ser
301  /  101                               331  /  111
GCC ACT GAT ACT GGA AAA CGA GAG AAA CAA TTA CAA CAA TGG AAA AAT AAT CTA AAA AAT
ala thr asp thr gly lys arg glu lys gln leu gln gln trp lys asn asn leu lys asn
361  /  121                               391  /  131
GAT GTG GAT AAC ACA ATT CTA TCT CAT GAA CAG AAA AAT GAG TTT AAA ACA AAA ATT GAT
asp val asp asn thr ile leu ser his glu gln lys asn glu phe lys thr lys ile asp
421  /  141                               451  /  151
GAA ACA AAT GAT TCT GAT GCA TTA TTA GAA TTA GAA AAT CAA TTT AAC GAA ACT AAT AGA
glu thr asn asp ser asp ala leu leu glu leu glu asn gln phe asn glu thr asn arg
```

FIG.6A

```
481 / 161                                 511 / 171
CTG TTA CAC ATC AAA CAA CAT GAA GAA GTT GAG AAA CAT AAC AAA CCT AAC CAA CAG AAA
leu leu his ile lys gln his glu glu val glu lys asp lys lys ala lys gln gln lys
541 / 181                                 571 / 191
ACT CTG AAA CAG TCA GAT ACG AAA GTA GAT CTA AGC AAT ATT GAC AAA GAG CTT AAT CAT
thr leu lys gln ser asp thr lys val asp leu ser asn ile asp lys glu leu asn his
601 / 201                                 631 / 211
CAA AAA AGT CAA GTT GAA gcA ATG GCA GAG CAA gcG GGA ATC ACA AAT GAA GAT AAA GAT
gln lys ser gln val glu ala met ala glu gln ala gly ile thr asn glu asp lys asp
661 / 221                                 691 / 231
TCT ATC CTG AAA AAA ATC GAA GAT ATT CGT AAA CAA GCT CAA CAA GCA GAT AAA AAA GAA
ser met leu lys lys ile glu asp ile arg lys gln ala gln gln ala asp lys lys glu
721 / 241                                 751 / 251
GAT GCC GAA GTA AAG GTT CGT GAA GAA CTA GGT AAA CTC TTT AGT TCA ACT AAA GCT GGT
asp ala glu val lys val arg glu glu leu gly lys leu phe ser ser thr lys ala gly
781 / 261                                 811 / 271
CTG GAT CAA CAA ATT CAA GAG CAT GTG AAG AAA GAA ACG AGT AGT GAG GAA AAT ACT CAG
leu asp gln glu ile gln glu his val lys lys glu thr ser ser glu glu asn thr gln
841 / 281                                 871 / 291
AAA GTT GAT GAA CAC TAT GCT AAT AGC CTT CAG AAC CTT GCT CAA AAA TCT CTT GAA GAA
lys val asp glu his tyr ala asn ser leu gln asn leu ala gln lys ser leu glu glu
901 / 301                                 931 / 311
CTA GAT AAG GCA ACT ACC AAT GAA CAA GCT ACA CAA GTT AAA AAT CAA TTC TTA GAA AAC
leu asp lys ala thr thr asn glu gln ala thr gln val lys asn gln phe leu glu asn
961 / 321                                 991 / 331
GCT CAA AAG CTC AAA GAA ATA CAA CCT CTT ATC AAA GAA ACG AAT GTG AAA TTG TAT AAG
ala gln lys leu lys glu ile gln pro leu ile lys glu thr asn val lys leu tyr lys
```

FIG.6B

```
1021 /  341                                       1051 /  351
GCT ATG AGT GAG AGC TTG GAG CAG GTT GAG AAG CAA TTA AAA CAT AAT 7CG GAA GCT AAT
ala met ser glu ser leu glu gln val glu lys glu leu lys his asn ser glu ala asn
1081 /  361                                       1111 /  371
TTA CAA GAT TTG GTT GCG AAA TCT AAA GAA ATC GTA AGA GAA TAC GAA GGA AAA CTT AAT
leu glu asp leu val ala lys ser lys glu ile val arg glu tyr glu gly lys leu asn
1141 /  381                                       1171 /  391
CAA TCT AAA AAT CTT CCA GAA TTA AAG CAA CTA GAA GAG GAA GCT CAT TCG AAG TTG AAA
gln ser lys asn leu pro glu leu lys gln leu glu glu glu ala his ser lys leu lys
1201 /  401                                       1231 /  411
CAA GTT GTG GAG CAT TTT AGA AAA AAA TTT AAA ACG TCA GAG CAA GTG ACA CCA AAA AAA
gln val val glu asp phe arg lys lys phe lys thr ser glu gln val thr pro lys lys
1261 /  421                                       1291 /  431
CGT GTC AAA CGA GAT TTA GCT GCr AAT GAA AAT AAT CAA CAA AAG ATT GAG TTA ACA GTT
arg val lys arg asp leu ala ala asn glu asn asn gln gln lys ile glu leu thr val
1321 /  441                                       1351 /  451
TCA CCA GAG AAT ATC ACT GTA TAT GAA GGT GAA GAC GTG AAA TTT ACA GTC ACA GCT AAA
ser pro glu asn ile thr val tyr glu gly glu asp val lys phe thr val thr ala lys
1381 /  461                                       1411 /  471
AGT GAT TCG AAG ACG ACG TTG GAC TTC AGT GAT CTT TTA ACA AAA TAT AAT CCG TCT GTA
ser asp ser lys thr thr leu asp phe ser asp leu leu thr lys tyr asn pro ser val
1441 /  481                                       1471 /  491
TCA GAT AGA ATT AGT ACA AAT TAT AAG ACT AAC ACG GAT AAT CAT AAG ATT GCC GAA ATC
ser asp arg ile ser thr asn tyr lys thr asn thr asp asn his lys ile ala glu ile
1501 /  501                                       1531 /  511
ACT ATC AAG AAT TTG AAG CTA AAT CAA AGT CAA ACA GTG ACT CTA AAA GCT AAA GAT GAT
thr ile lys asn leu lys leu asn glu ser gln thr val thr leu lys ala lys asp asp
```

FIG.6C

```
1561 /  521                             1591 /  531
TCT GGC AAT GTA GTT GAA AAA ACA TTC ACT ATT ACA GTC CAA AAG AAA GAG GAG AAA CAA
ser gly asn val val glu lys thr phe thr ile thr val gln lys lys glu glu lys gln
1621 /  541                             1651 /  551
GTT CCT AAA ACA CCA GAG CAG AAA CAT TCT AAA ACG GAA CAA AAC GTT CCT CAA GAA CCA
val pro lys thr pro glu gln lys asp ser lys thr glu glu lys val pro gln glu pro
1681 /  561                             1711 /  571
AAA TCA AAT GAC AAG AAT CAA TTA CAA GAG TTG ATT AAA TCA GCT CAA CAA GAA CTC GAA
lys ser asn asp lys asn gln leu gln glu leu ile lys ser ala gln gln glu leu glu
1741 /  581                             1771 /  591
AAG TTA GAA AAA GCA ATA AAA GAA TTA ATG GAG CAA CCA GAG ATT CCA TCC AAT CCA GAG
lys leu glu lys ala ile lys glu leu met glu gln pro glu ile pro ser asn pro glu
1801 /  601                             1831 /  611
TAT GGT ATT CAA AAA TCT ATT TGG GAG TCA CAA AAA GAG CCT ATC CAG GAA GCC ATA ACA
tyr gly ile gln lys ser ile trp glu ser gln lys glu pro ile gln glu ala ile thr
1861 /  621                             1891 /  631
AGT TTT AAC AAG ATT ATT GGT GAT TCA TCT TCA AAA TAC TAC ACA GAG CAC TAT TTT AAC
ser phe lys lys ile ile gly asp ser ser ser lys tyr tyr thr glu his tyr phe asn
1921 /  641                             1951 /  651
AAA TAT AAA TCT CAT TTT ATG AAT TAT CAA CTT CAT GCA CAA ATG GAG ATC CTG ACT AGA
lys tyr lys ser asp phe met asn tyr gln leu his ala gln met glu met leu thr arg
1981 /  661                             2011 /  671
AAA GTG GTT CAG TAT ATG AAC AAA TAT CCT GAT AAT GCA GAA ATT AAA AAG ATA TTT GAG
lys val val gln tyr met asn lys tyr pro asp asn ala glu ile lys lys ile phe glu
2041 /  681                             2071 /  691
TCA GAT ATG AAG AGA ACG AAA GAA GAT AAT TAC GGA AGT TTA GAA AAT GAT GCT TTG AAA
ser asp met lys arg thr lys glu asp asn tyr gly ser leu glu asn asp ala leu lys
```

FIG.6D

```
2101 /  701                                       2131 /  711
GGC TAT TTT GAG AAA TAT TTC CTT ACA CCA TTT AAT AAA ATT AAG CAG ATT GTA GAT GAT
gly tyr phe glu lys tyr phe leu thr pro phe asn lys ile lys gln ile val asp asp
2161 /  721                                       2191 /  731
TTG GAT AAA AAA GTA GAA CAA GAT CAG CCA GCA CCA ATT CCG GAA AAT TCA GAA ATG GAT
leu asp lys lys val glu gln asp gln pro ala pro ile pro glu asn ser glu met asp
2221 /  741                                       2251 /  751
CAG GCT AAG GAA AAG GCT AAG ATT GCT GTA TCG AAG TAT ATG AGT AAG GTT TTA GAT GGA
gln ala lys glu lys ala lys ile ala val ser lys tyr met ser lys val leu asp gly
2281 /  761                                       2311 /  771
GTT CAT CAA CAT CTG CAG AAG AAA AAT CAC AGT AAA ATT GTT GAT CTT TTT AAG GAA CTT
val his gln his leu gln lys lys asn his ser lys ile val asp leu phe lys glu leu
2341 /  781                                       2371 /  791
GAA GCG ATT AAA CAA CAA ACT ATT TTT GAT ATT GAC AAT GCA AAG ACT GAA GTA GAG ATT
glu ala ile lys gln gln thr ile phe asp ile asp asn ala lys thr glu val glu ile
2401 /  801                                       2431 /  811
GAT AAC TTA GTA CAC GAT GCA TTC TCA AAA ATG AAT GCT ACT GTT GCT AAA TTT CAA AAA
asp asn leu val his asp ala phe ser lys met asn ala thr val ala lys phe gln lys
2461 /  821                                       2491 /  831
GGT CTA GAG ACA AAT ACG CCA GAA ACT CCA GAT ACA CCG AAG ATT CCA GAG CTA CCT CAA
gly leu glu thr asn thr pro glu thr pro asp thr pro lys ile pro glu leu pro gln
2521 /  841                                       2551 /  851
GCC CCA GAT ACA CCG CAG GCT CCA GAC ACA CCG CAT GTT CCG GAA TCA CCA AAG GCC CCA
ala pro asp thr pro gln ala pro asp thr pro his val pro glu ser pro lys ala pro
```

FIG.6E

```
2581 /  861                                       2611 /  871
GAA GCA CCG CGT GTT CCG GAA TCA CCA AAC ACT CCA GAA GCA CCG CAT GTT CCG GAA TCA
glu ala pro arg val pro glu ser pro lys thr pro glu ala pro his val pro glu ser
2641 /  881                                       2671 /  891
CCA AAG GCC CCA GAA CCA CCG CGT GTT CCG GAA TCA CCA AAC ACT CCA GAA GCA CCG CAT
pro lys ala pro glu ala pro arg val pro glu ser pro lys thr pro glu ala pro his
2701 /  901                                       2731 /  911
GTT CCG GAA TCA CCA AAG ACT CCA GAA GCA CCA AAG ATT CCG GAA CCC CCT AAG ACT CCA
val pro glu ser pro lys thr pro glu ala pro lys ile pro glu pro pro lys thr pro
2761 /  921                                       2791 /  931
GAC GTC CCT AAG CTT CCA GAC GTC CCT AAG CTT CCA CAC GTC CCT AAG CTT CCA GAT GCA
asp val pro lys leu pro asp val pro lys leu pro asp val pro lys leu pro asp ala
2821 /  941                                       2851 /  951
CCG AAG TTA CCA GAT GGG TTA AAT AAA GTT GGA CAA GCA GTA TTT ACA TCA ACT GAT GGA
pro lys leu pro asp gly leu asn lys val gly gln ala val phe thr ser thr asp gly
2881 /  961                                       2911 /  971
AAT ACT AAG GTT ACG GTT GTA TTT GAT AAA CCT ACA GAT GCT GAT AAG TTA CAT CTC AAG
asn thr lys val thr val val phe asp lys pro thr asp ala asp lys leu his leu lys
2941 /  981                                       2971 /  991
GAA CTA ACG ACG AAA GAG TTG GCT GAT AAA ATT GCT CAT AAA ACA GGA GGA GGA ACA GTT
glu val thr thr lys glu leu ala asp lys ile ala his lys thr gly gly gly thr val
3001 / 1001                                       3031 / 1011
CGT CTG TTT GAC TTA TCT CTT TCT AAA GGA GGC AAG GAA ACA CAT GTC AAT GGA GAA CGA
arg val phe asp leu ser leu ser lys gly gly lys glu thr his val asn gly glu arg
3061 / 1021                                       3091 / 1031
ACT GTT CGG CTC GCG CTT GGG CAG ACT GGC TCA GAT GTT CAC GTC TAT CAC GTA AAG GAA
thr val arg leu ala leu gly gln thr gly ser asp val his val tyr his val lys glu
```

FIG.6F

```
3121 / 1041                                 3151 / 1051
AAT GGC GAC CTT GAG CGT ATT CCT TCT AAA GTT GAA AAT GGG CAA GTT GTT TTT AAA ACG
asn gly asp leu glu arg ile pro ser lys val glu asn gly gln val val phe lys thr
3181 / 1061                                 3211 / 1071
AAC CAC TTC AGT TTG TTT GCG ATT AAG ACA CTT TCT kAG GAT CAA AAT GTT ACT CCA CCG
asn his phe ser leu phe ala ile lys thr leu ser lys asp gln asn val thr pro pro
3241 / 1081                                 3271 / 1091
AAG CAG ACT AAA CCT TCT ACC CAA GGC AGT CAA GTA GAG ATT GCA GAG AGT CAA ACT GGA
lys gln thr lys pro ser thr gln gly ser gln val glu ile ala glu ser gln thr gly
3301 / 1101                                 3331 / 1111
AAA TTC CAG AGT AAA GCA GCT kAT CAT AAA GCA CTG GCT ACT GGA AAT GkA ACA GTG GCA
lys phe gln ser lys ala ala asn his lys ala leu ala thr gly asn glu thr val ala
3361 / 1121                                 3391 / 1131
AAA GGA AAT CCT ACA TCA ACA ACG GAA AAG AAA ctc gag cac cac
lys gly asn pro thr ser thr thr glu lys lys leu glu his his
```

FIG.6G

```
bagorf pnv34/A6/seq -> 1-phase Translation
DNA sequence     3384 b.p.   atgAGTGAGCTT ... AGAAGAAAATCA   linear

1   /   1                                31  /  11
atg AGT GAG CTT GTA AAG GAC GAT AGT GTG AAG ACT ACC GAG GTT GCA GCT AAG CCC TAT
met ser glu leu val lys asp asp ser val lys thr thr glu val ala ala lys pro tyr
61  /  21                                91  /  31
CCA AGT ATG GCT CAA ACA GAT CAA GGA AAT AAT TCA TCA TCC TCG GAA CTT GAG ACA ACA
pro ser met ala gln thr asp gln gly asn asn ser ser ser ser glu leu glu thr thr
121 /  41                                151 /  51
AgG ATG GAA ATT CCT ACA ACA GAC ATA AAA AAA GCT GTT GAA CCG GTC GAG AAA ACA GCT
arg met glu ile pro thr thr asp ile lys lys ala val glu pro val glu lys thr ala
181 /  61                                211 /  71
GGG GAA ACA TCT GCC ACT GAT ACT GGA AAA CGA GAG AAA CAA TTA CAA CAA TGG AAA AAT
gly glu thr ser ala thr asp thr gly lys arg glu lys gln leu gln gln trp lys asn
241 /  81                                271 /  91
AAT CTA AAA AAT GAT GTG GAT AAC ACA ATT CTA TCT CAT GAA CAG AAA AAT GAG TTT AAA
asn leu lys asn asp val asp asn thr ile leu ser his glu gln lys asn glu phe lys
301 / 101                                331 / 111
ACA AAA ATT GAT GAA ACA AAT GAT TCT GAT GCA TTA TTA GAA TTA GAA AAT CAA TTT AAC
thr lys ile asp glu thr asn asp ser asp ala leu leu glu leu glu asn gln phe asn
361 / 121                                391 / 131
GAA ACT AAT AGA CTG TTA CAC ATC AAA CAA CAT GAA GAA GTT GAG AAA GAT AAG AAA GCT
glu thr asn arg leu leu his ile lys gln his glu glu val glu lys asp lys lys ala
421 / 141                                451 / 151
AAG CAA CAG AAA ACT CTG AAA CAG TCA GAT ACG AAA GTA GAT CTA AGC AAT ATT GAC AAA
lys gln gln lys thr leu lys gln ser asp thr lys val asp leu ser asn ile asp lys
481 / 161                                511 / 171
GAG CTT AAT CAT CAA AAA AGT CcA GTT GAA AAA ATG GCA GAG CcA AAG GGA ATC ACA AAT
glu leu asn his gln lys ser pro val glu lys met ala glu pro lys gly ile thr asn
```

FIG.7A

```
541  /  181                              571  /  191
GAA GAT AAA GAT TCT ATG CTG AAA AAA ATC GAA GAT ATT CGT AAA CAA GCT CAA CAA GCA
glu asp lys asp ser met leu lys lys ile glu asp ile arg lys gln ala gln gln ala
601  /  201                              631  /  211
GAT AAA AAA GAA GAT GCC GAA GTA AAG GTT CGT GAA GAA CTA GGT AAA CTC TTT AGT TCA
asp lys lys glu asp ala glu val lys val arg glu glu leu gly lys leu phe ser ser
661  /  221                              691  /  231
ACT AAA GCT GGT CTG GAT CAA GAA ATT CAt GAG CAT GTG AAG AAA GAA ACG AGT AGT GAG
thr lys ala gly leu asp gln glu ile his glu his val lys lys glu thr ser ser glu
721  /  241                              751  /  251
GAA AAT ACT CAG AAA GTT GAT GAA CAC TAT GCT AAT AGC CTT CAG AAC CTT GCT CAA AAA
glu asn thr gln lys val asp glu his tyr ala asn ser leu gln asn leu ala gln lys
781  /  261                              811  /  271
TCT CTT GAA GAA CTA GAT AAG GCA ACT ACC AAT GAA CAA GCT ACA CAA GTT AAA AAT CAA
ser leu glu glu leu asp lys ala thr thr asn glu gln ala thr gln val lys asn gln
841  /  281                              871  /  291
TTC TTA GAA AAC GCT CAA AAG CTC AAA GAA ATg CAA CCT CTT ATC AAA GAA ACG AAT GTG
phe leu glu asn ala gln lys leu lys glu met gln pro leu ile lys glu thr asn val
901  /  301                              931  /  311
AAA TTG TAT AAG GCT ATG AGT GAG AGC TTG GAG CAG GTT GAG AAG GAA TTA AAA CAT AAT
lys leu tyr lys ala met ser glu ser leu glu gln val glu lys glu leu lys his asn
961  /  321                              991  /  331
TCG GAA GCT AAT TTA GAA GAT TTG GTT GCG AAA TCT AAA GAA ATC GTA AGA GAA TAC GAA
ser glu ala asn leu glu asp leu val ala lys ser lys glu ile val arg glu tyr glu
1021 /  341                              1051 /  351
GGA AAA CTT AAT CAA TCT AAA AAT CTT CCA GAA TTA AAG CAA CTA GAA GAG GAA GCT CAT
gly lys leu asn gln ser lys asn leu pro glu leu lys gln leu glu glu glu ala his
1081 /  361                              1111 /  371
TCG AAG TTG AAA CAA GTT GTG GAG GAT TTT AGA AAA AAA TTT AAA ACG TCA GAG CAA GTG
ser lys leu lys gln val val glu asp phe arg lys lys phe lys thr ser glu gln val
```

FIG.7B

```
1141 /  381                                       1171 /  391
ACA CCA AAA AAA CGT GTC AAA CGA GAT TTA GCT GCT AAT GAA AAT AAT CAA CAA AAG ATT
thr pro lys lys arg val lys arg asp leu ala ala asn glu asn asn gln gln lys ile
1201 /  401                                       1231 /  411
GAG TTA ACA GTT TCA CCA GAG AAT ATC ACT GTA TAT GAA GGT GAA GAC GTG AAA TTT ACA
glu leu thr val ser pro glu asn ile thr val tyr glu gly glu asp val lys phe thr
1261 /  421                                       1291 /  431
GTC ACA GCT AAA AGT GAT TCG AAG ACG ACG TTG GAC TTC AGT GAT CTT TTA ACA AAA TAT
val thr ala lys ser asp ser lys thr thr leu asp phe ser asp leu leu thr lys tyr
1321 /  441                                       1351 /  451
AAT CCG TCT GTA TCA GAT AGA ATT AGT ACA AAT TAT AAG ACT AAC ACG GAT AAT CAT AAG
asn pro ser val ser asp arg ile ser thr asn tyr lys thr asn thr asp asn his lys
1381 /  461                                       1411 /  471
ATT GCC GAA ATC ACT ATC AAG AAT TTG AAG CTA AAT GAA AGT CAA ACA GTG ACT CTA AAA
ile ala glu ile thr ile lys asn leu lys leu asn glu ser gln thr val thr leu lys
1441 /  481                                       1471 /  491
GCT AAA GAT GAT TCT GGC AAT GTA GTT GAA AAA ACA TTC ACT ATT ACA GTG CAA AAG AAA
ala lys asp asp ser gly asn val val glu lys thr phe thr ile thr val gln lys lys
1501 /  501                                       1531 /  511
GAG GAG AAA CAA GTT CCT AAA ACA CCA GAG CAG AAA GAT TCT AAA ACG GAA GAA AAG GTT
glu glu lys gln val pro lys thr pro glu gln lys asp ser lys thr glu glu lys val
1561 /  521                                       1591 /  531
CCT CAA GAA CCA AAA TCA AAT GAC AAG AAT CAA TTA CAA GAG TTG ATT AAA TCA GCT CAA
pro gln glu pro lys ser asn asp lys asn gln leu gln glu leu ile lys ser ala gln
1621 /  541                                       1651 /  551
CAA GAA CTG GAA AAG TTA GAA AAA GCA ATA AAA GAA TTA ATG GAG CAA CCA GAG ATT CCA
gln glu leu glu lys leu glu lys ala ile lys glu leu met glu gln pro glu ile pro
1681 /  561                                       1711 /  571
TCC AAT CCA GAG TAT GGT ATT CAA AAA TCT ATT TGG GAG TCA CAA AAA GAG CCT ATC CAG
ser asn pro glu tyr gly ile gln lys ser ile trp glu ser gln lys glu pro ile gln
```

FIG.7C

```
1741 /  581                             1771 /  591
GAA GCC ATA ACA AGT TTT AAG AAG ATT ATT GGT GAT TCA TCT TCA AAA TAC TAC ACA GAG
glu ala ile thr ser phe lys lys ile ile gly asp ser ser ser lys tyr tyr thr glu
1801 /  601                             1831 /  611
CAC TAT TTT AAC AAA TAT AAA TCT GAT TTT ATG AAT TAT CAA CTT CAT GCA CAA ATG GAG
his tyr phe asn lys tyr lys ser asp phe met asn tyr gln leu his ala gln met glu
1861 /  621                             1891 /  631
ATG CTG ACT AGA AAA GTG GTT CAG TAT ATG AAC AAA TAT CCT GAT AAT GCA GAA ATT AAA
met leu thr arg lys val val gln tyr met asn lys tyr pro asp asn ala glu ile lys
1921 /  641                             1951 /  651
AAG ATA TTT GAG TCA GAT ATG AAG AGA ACG AAA GAA GAT AAT TAC GGA AGT TTA GAA AAT
lys ile phe glu ser asp met lys arg thr lys glu asp asn tyr gly ser leu glu asn
1981 /  661                             2011 /  611
GAT GCT TTG AAA GGC TAT TTT GAG AAA TAT TTC CTT ACA CCA TTT AAT AAA ATT AAG CAG
asp ala leu lys gly tyr phe glu lys tyr phe leu thr pro phe asn lys ile lys gln
2041 /  681                             2071 /  691
ATT GTA GAT GAT TTG GAT AAA AAA GTA GAA CAA GAT CAG CCA GCA CCA ATT CCG GAA AAT
ile val asp asp leu asp lys lys val glu gln asp gln pro ala pro ile pro glu asn
2101 /  701                             2131 /  711
TCA GAA ATG GAT CAG GCT AAG GAA AAG GCT AAG ATT GCT GTA TCG AAG TAT ATG AGT AAG
ser glu met asp gln ala lys glu lys ala lys ile ala val ser lys tyr met ser lys
2161 /  721                             2191 /  731
GTT TTA GAT GGA GTT CAT CAA CAT CTG CAG AAG AAA AAT cAC AGT AAA ATT GTT GAT CTT
val leu asp gly val his gln his leu gln lys lys asn his ser lys ile val asp leu
2221 /  741                             2251 /  751
TTT AAG GAA CTT GAA GCG ATT AAA CAA CAA ACT ATT TTT GAT ATT GAC AAT GCA AAG ACT
phe lys glu leu glu ala ile lys gln gln thr ile phe asp ile asp asn ala lys thr
2281 /  761                             2311 /  771
GAA GTA GAG ATT GAT AAC TTA GTA CAC GAT GCA TTC TCA AAA ATG AAT GCT ACT GTT GCT
glu val glu ile asp asn leu val his asp ala phe ser lys met asn ala thr val ala
```

FIG.7D

```
2341 /  781                             2371 /  791
AAA TTT CAA AAA GGT CTA GAG ACA AAT ACG CCA GAA ACT CCA GAT ACA CCG AAG ATT CCA
lys phe gln lys gly leu glu thr asn thr pro glu thr pro asp thr pro lys ile pro
2401 /  801                             2431 /  811
GAG CTA CCT CAA GCC CCA GAT ACA CCG CAG GCT CCA GAC ACA CCG CAT GTT CCG GAA TCA
glu leu pro gln ala pro asp thr pro gln ala pro asp thr pro his val pro glu ser
2461 /  821                             2491 /  831
CCA AAG GCC CCA GAA GCA CCG CGT GTT CCG GAA TCA CCA AAG ACT CCA GAA GCA CCG CAT
pro lys ala pro glu ala pro arg val pro glu ser pro lys thr pro glu ala pro his
2521 /  841                             2551 /  851
GTT CCG GAA TCA CCA AAG GCC CCA GAA GCA CCG CGT GTT CCG GAA TCA CCA AAG ACT CCA
val pro glu ser pro lys ala pro glu ala pro arg val pro glu ser pro lys thr pro
2581 /  861                             2611 /  871
GAA GCA CCG CAT GTT CCG GAA TCA CCA AAG ACT CCA GAA GCA CCA AAG ATT CCG GAA CCC
glu ala pro his val pro glu ser pro lys thr pro glu ala pro lys ile pro glu pro
2641 /  881                             2671 /  891
CCT AAG ACT CCg GAC GTC CCT AAG CTT CCA GAC GTC CCT AAG CTT CCA GAC GTC CCT AAG
pro lys thr pro asp val pro lys leu pro asp val pro lys leu pro asp val pro lys
2701 /  901                             2731 /  911
CTT CCA GAT GCA CCG AAG TTA CCA GAT GGG TTA AAT AAA GTT GGA CAA GCA GTA TTT ACA
leu pro asp ala pro lys leu pro asp gly leu asn lys val gly gln ala val phe thr
2761 /  921                             2791 /  931
TCA ACT GAT GGA AAT ACT AAG GTT ACG GTT GTA TTT GAT AAA CCT ACA GAT GCT GAT AAG
ser thr asp gly asn thr lys val thr val val phe asp lys pro thr asp ala asp lys
2821 /  941                             2851 /  951
TTA CAT CTC AAG GAA GTA ACG ACG AAA GAG TTG GCT GAT AAA ATT GCT CAT AAA ACA GGA
leu his leu lys glu val thr thr lys glu leu ala asp lys ile ala his lys thr gly
2881 /  961                             2911 /  971
GGA GGA ACA GTT CGT GTG TTT GAC TTA TCT CTT TCT AAA GGA GGC AAG GAA ACA CAT GTC
gly gly thr val arg val phe asp leu ser leu ser lys gly gly lys glu thr his val
```

FIG. 7E

```
2941 /  981                                   2971 /  991
AAT GGA GAA CGA ACT GTT CGG CTC GCG CTT GGG CAG ACT GGC TCA GAT GTT CAC GTC TAT
asn gly glu arg thr val arg leu ala leu gly gln thr gly ser asp val his val tyr
3001 / 1001                                   3031 / 1011
CAC GTA AAG GAA AAT GGC GAC CTT GAG CGT ATT CCT TCT AAA GTT GAA AAT GGG CAA GTT
his val lys glu asn gly asp leu glu arg ile pro ser lys val glu asn gly gln val
3061 / 1021                                   3091 / 1031
GTT TTT AAA ACG AAC CAC TTC AGT TTG TTT GCG ATT AAG ACA CTT TCT AAG GAT CAA AAT
val phe lys thr asn his phe ser leu phe ala ile lys thr leu ser lys asp gln asn
3121 / 1041                                   3151 / 1051
GTT ACT CCA CCG AAG CAG ACT AAA CCT TCT ACC CAA GGC AGT CAA GTA GAG ATT GCA GAG
val thr pro pro lys gln thr lys pro ser thr gln gly ser gln val glu ile ala glu
3181 / 1061                                   3211 / 1071
AGT CAA ACT GGA AAA TTC CAG AGT AAA GCA GCT AAT CAT AAA GCA CTG GCT ACT GGA AAT
ser gln thr gly lys phe gln ser lys ala ala asn his lys ala leu ala thr gly asn
3241 / 1081                                   3271 / 1091
GAA ACA GTG GCA AAA GGA AAT CCT ACA TCA ACA ACG GAA AAG AAA TTG CCA TAT ACA GGA
glu thr val ala lys gly asn pro thr ser thr thr glu lys lys leu pro tyr thr gly
3301 / 1101                                   3331 / 1111
GTG GCA TCT AAT CTA GTT CTT GAA ATT ATG GGT CTC CTT GGT TTG ATT GGA ACT TCA TTC
val ala ser asn leu val leu glu ile met gly leu leu gly leu ile gly thr ser phe
3361 / 1121
ATC GCA ATG AAA AGA AGA AAA TCA
ile ala met lys arg arg lys ser
```

FIG.7F

```
DGB1R -> 1-phase Translation
DNA sequence     3388 b.p.   agatctcgatcc ... tcgagcaccacc   linear

1   /   1                            31   /   11
aga tct cga tcc cgc gaa att aat acg act cac tat agg gga att gtg agc gga taa caa
arg ser arg ser arg glu ile asn thr thr his tyr arg gly ile val ser gly OCH gln
61  /   21                           91   /   31
ttc ccc tct aga aat aat ttt gtt taa ctt taa gaa gga gat ata cat atg AGT GAG CTT
phe pro ser arg asn asn phe val OCH leu OCH glu gly asp ile his met ser glu leu
121  /  41                           151  /   51
GTA AAG GAC GAT AGT GTG AAG ACT ACC GAG GTT GCA GCT AAG CCC TAT CCA AGT ATG GCT
val lys asp asp ser val lys thr thr glu val ala ala lys pro tyr pro ser met ala
181  /  61                           211  /   71
CAA ACA GAT CAA GGA AAT AAT TCA TCA TCC TCG GAA CTT GAG ACA ACA AGG ATG GAA ATT
gln thr asp gln gly asn asn ser ser ser ser glu leu glu thr thr arg met glu ile
241  /  81                           271  /   91
CCT ACA ACA GAC ATA AAA AAA GCT GTT GAA CCG GTC GAG AAA ACA GCT GGG GAA ACA TCT
pro thr thr asp ile lys lys ala val glu pro val glu lys thr ala gly glu thr ser
301  /  101                          331  /  111
GCC ACT CAT ACT GGA AAA CGA GAG AAA CAA TTA CAA CAA TGG AAA AAT AAT CTA AAA AAT
ala thr asp thr gly lys arg glu lys gln leu gln gln trp lys asn asn leu lys asn
361  /  121                          391  /  131
GAT GTG GAT AAC ACA ATT CTA TCT CAT GAA CAG AAA AAT GAG TTT AAA ACA AAA ATT GAT
asp val asp asn thr ile leu ser his glu gln lys asn glu phe lys thr lys ile asp
421  /  141                          451  /  151
GAA ACA AAT GAT TCT GAT GCA TTA TTA GAA TTA GAA AAT CAA TTT AAC GPLA ACT AAT AGA
glu thr asn asp ser asp ala leu leu glu leu glu asn gln phe asn glu thr asn arg
```

FIG.8A

```
481 / 161                               511 / 171
CTG TTA CAC ATC AAA CAA CAT GAA GAA GTT GAG AAA GAT AAG AAA GCT AAG CAA CAG AAA
leu leu his ile lys gln his glu glu val glu lys asp lys lys ala lys gln gln lys
541 / 181                               571 / 191
ACT CTG AAA CAG TCA GAT ACG AAA GTA GAT CTA AGC AAT ATT GAC AAA GAG CTT AAT CAT
thr leu lys gln ser asp thr lys val asp leu ser asn ile asp lys glu leu asn his
601 / 201                               631 / 211
CAA AAA AGT CAA gaa gcG GGA ATC ACA AAT GAA GAT AAA GAT TCT ATG CTG AAA AAA ATC
gln lys ser gln glu ala gly ile thr asn glu asp lys asp ser met leu lys lys ile
661 / 221                               691 / 231
GAA GAT ATT CGT AAA CAA GCT CAA CAA CCA GAT AAA AAA GAA GAT GCC GAA GTA AAG GTT
glu asp ile arg lys gln ala gln gln ala asp lys lys glu asp ala glu val lys val
721 / 241                               751 / 251
CGT GAA GAA CTA GGT AAA CTC TTT AGT TCA ACT AAA GCT GGT CTG GAT CAA GAA ATT CAA
arg glu glu leu gly lys leu phe ser ser thr lys ala gly leu asp gln glu ile gln
781 / 261                               811 / 271
GAG CAT GTG AAG AAA GAA ACG AGT AGT GAG GAA AAT ACT CAG AAA GTT GAT GAA CAC TAT
glu his val lys lys glu thr ser ser glu glu asn thr gln lys val asp glu his tyr
841 / 281                               871 / 291
GCT AAT AGC CTT CAG AAC CTT GCT CAA AAA TCT CTT GAA GAA CTA GAT AAG GCA ACT ACC
ala asn ser leu gln asn leu ala gln lys ser leu glu glu leu asp lys ala thr thr
901 / 301                               931 / 311
AAT GkA CAA GCT ACA CAA GTT AAA AAT CAA TTC TTA GAA AAC GCT CAA AAG CTC AAA GAA
asn glu gln ala thr gln val lys asn gln phe leu glu asn ala gln lys leu lys glu
961 / 321                               991 / 331
ATA CAA CCT CTT ATC AAA GAA ACG AAT GTG AAA TTG TAT AAG GCT ATG AGT GAG AGC TTG
ile gln pro leu ile lys glu thr asn val lys leu tyr lys ala met ser glu ser leu
```

FIG.8B

```
1021 /  341                                 1051 /  351
GAG CAG GTT GAG AAG GAA TTA AAA CAT AAT TCG GAA GCT AAT TTA GAA GAT TTG GTT GCG
glu gln val glu lys glu leu lys his asn ser glu ala asn leu glu asp leu val ala
1081 /  361                                 1111 /  371
AAA TCT AAA GAA ATC GTA AGA GAA TAC GAA GGA AAA CTT AAT CAA TCT AAA AAT CTT CCA
lys ser lys glu ile val arg glu tyr glu gly lys leu asn gln ser lys asn leu pro
1141 /  381                                 1171 /  391
GAA TTA AAG CAA CTA GAA GAG GAA GCT CAT TCG AAG TTG AAA CAA GTT GrG GAG GAT TTT
glu leu lys gln leu glu glu glu ala his ser lys leu lys gln val val glu asp phe
1201 /  401                                 1231 /  411
AGA AAA AAA TTT AAA ACG TCA GAG CAA GTG ACA CCA AAA AAA CGT CTC AAA CGA GAT TTA
arg lys lys phe lys thr ser glu gln val thr pro lys lys arg val lys arg asp leu
1261 /  421                                 1291 /  431
GCT GCT AAT GAA AAT AAT CAA CAA AAG ATT GAG TTA ACA GTT TCA CCA GAG AAT ATC ACT
ala ala asn glu asn asn gln gln lys ile glu leu thr val ser pro glu asn ile thr
1321 /  441                                 1351 /  451
GTA TAT GAA GGT GAA GAC GTG AAA TTT ACA GTC ACA GCT AAA AGT GAT TCG AAG ACG ACG
val tyr glu gly glu asp val lys phe thr val thr ala lys ser asp ser lys thr thr
1381 /  461                                 1411 /  471
TTG GAC TTC AGT GAT CTT TTA ACA AAA TAT AAT CCG TCT GTA TCA GAT AGA ATT AGT ACA
leu asp phe ser asp leu leu thr lys tyr asn pro ser val ser asp arg ile ser thr
1441 /  481                                 1471 /  491
AAT TAT AAG ACT AAC ACG GAT AAT CAT AAG ATT GCC GAA ATC ACT ATC AAG AAT TTG AAG
asn tyr lys thr asn thr asp asn his lys ile ala glu ile thr ile lys asn leu lys
1501 /  501                                 1531 /  511
CTA AAT GAA AGT CAA ACA GTG ACT CTA AAA GCT AAA GAT GAT TCT GGC AAT GTA GTT GAA
leu asn glu ser gln thr val thr leu lys ala lys asp asp ser gly asn val val glu
```

FIG.8C

```
1561 /  521                                1591 /  531
AAA ACA TTC ACT ATT ACA GTG CAA AAG AAA GAG GAG AAA CAA GTT CCT AAA ACA CCA GAG
lys thr phe thr ile thr val gln lys lys glu glu lys gln val pro lys thr pro glu
1621 /  541                                1651 /  551
CAG AAA GAT TCT AAA ACG GAA GAA AAG GTT CCT CAA GAA CCA AAA TCA AAT GAC AAG AAT
gln lys asp ser lys thr glu glu lys Val pro gln glu pro lys ser asn asp lys asn
1681 /  561                                1711 /  571
CAA TTA CAA GAG TTG ATT AAA TCA GCT CAA CAA GAA CTG GAA AAG TTA GAA AAA GCA ATA
gln leu gln glu leu ile lys ser ala gln gln glu leu glu lys leu glu lys ala ile
1741 /  581                                1771 /  591
AAA GAA TTA ATG GAG CAA CCA GAG ATT CCA TCC AAT CCA GAG TAT GGT ATT CAA AAA TCT
lys glu leu met glu gln pro glu ile pro ser asn pro glu tyr gly ile gln lys ser
1801 /  601                                1831 /  611
ATT TGG GAG TCA CAA AAA GAG CCT ATC CAG GAA GCC ATA ACA AGT TTT AAG AAG ATT ATT
ile trp glu ser gln lys glu pro ile gln glu ala ile thr ser phe lys lys ile ile
1861 /  621                                1891 /  631
GGT GAT TCA TCT TCA AAA TAC TAC ACA GAG CAC TAT TTT AAC AAA TAT AAA TCT CAT TTT
gly asp ser ser ser lys tyr tyr thr glu his tyr phe asn lys tyr lys ser asp phe
1921 /  641                                1951 /  651
ATG AAT TAT CAA CTT CAT GCA CAA ATG GAG ATG CTG ACT AGA AAA GTG GTT CAG TAT ATG
met asn tyr gln leu his ala gln met glu met leu thr arg lys val val gln tyr met
1981 /  661                                2011 /  671
AAC AAA TAT CCT GAT AAT GCA GAA ATT AAA AAG ATA TTT GAG TCA GAT ATG AAG AGA ACG
asn lys tyr pro asp asn ala glu ile lys lys ile phe glu ser asp met lys arg thr
2041 /  681                                2071 /  691
AAA GAA GAT AAT TAC GGA AGT TTA GAA AAT GAT GCT TTG AAA GGC TAT TTT GAG AAA TAT
lys glu asp asn tyr gly ser leu glu asn asp ala leu lys gly tyr phe glu lys tyr
```

FIG.8D

```
2101 /  701                                       2131 /  711
TTC CTT ACA CCA TTT AAT AAA ATT AAG CAG ATT GTA GAT GAT TTC GAT AAA AAA GTA GAA
phe leu thr pro phe asn lys ile lys gln ile val asp asp leu asp lys lys val glu
2161 /  721                                       2191 /  731
CAA GAT CAG CCA GCA CCA ATT CCG GAA AAT TCA GAA ATG GAT CAG GCT AAG GAA AAG GCT
gln asp gln pro ala pro ile pro glu asn ser glu met asp gln ala lys glu lys ala
2221 /  741                                       2251 /  751
AAG ATT GCT GTA TCG AAG TAT ATG AGT AAG GTT TTA GAT GGA GTT CAT CAA CAT CTG CAG
lys ile ala val ser lys tyr met ser lys val leu asp gly val his gln his leu gln
2281 /  761                                       2311 /  771
AAG AAA AAT CAC AGT AAA ATT GTT GAT CTT TTT AAG GAA CTT GAA GCG ATT AAA CAA CAA
lys lys asn his ser lys ile val asp leu phe lys glu leu glu ala ile lys gln gln
2341 /  781                                       2371 /  791
ACT ATT TTT GAT ATT GAC AAT GCA AAG ACT GAA GTA GAG ATT GAT AAC TTA GTA CAC GAT
thr ile phe asp ile asp asn ala lys thr glu val glu ile asp asn leu val his asp
2401 /  801                                       2431 /  811
GCA TTC TCA AAA ATG AAT GCT ACT GTT GCT AAA TTT CAA AAA GGT CTA GAG ACA AAT ACG
ala phe ser lys met asn ala thr val ala lys phe gln lys gly leu glu thr asn thr
2461 /  821                                       2491 /  831
CCA GAA ACT CCA GAT ACA CCG AAG ATT CCA GAG CTA CCT CAA GCC CCA GAT ACA CCG CAG
pro glu thr pro asp thr pro lys ile pro glu leu pro gln ala pro asp thr pro gln
2521 /  841                                       2551 /  851
GCT CCA GAC ACA CCG CAT GTT CCG CAA TCA CCA AAG GCC CCA GAA GCA CCG CGT GTT CCG
ala pro asp thr pro his val pro glu ser pro lys ala pro glu ala pro arg val pro
2581 /  861                                       2611 /  871
GAA TCA CCA AAG ACT CCA GAA GCA CCC CAT GTT CCG GAA TCA CCA AAG GCC CCA GAA GCA
glu ser pro lys thr pro glu ala pro his val pro glu ser pro lys ala pro glu ala
```

FIG.8E

```
2641 /  881                             2671 /  891
CCG CGT GTT CCG GAA TCA CCA AAG ACT CCA GAA GCA CCG CAT GTT CCG GAA TCA CCA AAG
pro arg val pro glu ser pro lys thr pro glu ala pro his val pro glu ser pro lys
2701 /  901                             2731 /  911
ACT CCA GAA GCA CCA AAG ATT CCG GAA CCC CCT AAG ACT CCA GAC GTC CCT AAC CTT CCA
thr pro glu ala pro lys ile pro glu pro pro lys thr Pro asp Val pro lys leu pro
2761 /  921                             2791 /  931
GAC GTC CCT AAG CTT CCA GAC GTC CCT AAG CTT CCA GAT GCA CCG AAG TTA CCA CAT GGG
asp Val pro lys leu pro asp Val pro lys leu pro asp ala pro lys leu pro asp gly
2821 /  941                             2851 /  951
TTA AAT AAA GTT GGA CAA GCA GTA TTT ACA TCA ACT GAT GGA AAT ACT AAG GTT ACG GTT
leu asn lys Val gly gln ala Val phe thr ser thr asp gly asn thr lys Val thr Val
2881 /  961                             2911 /  971
GTA TTT GAT AAA CCT ACA GAT GCT GAT AAG TTA CAT CTC AAG GAA GTA ACG ACG AAA GAG
Val phe asp lys pro thr asp ala asp lys leu his leu lys glu Val thr thr lys glu
2941 /  981                             2971 /  991
TTG GCT GAT AAA ATT GCT CAT AAA ACA GGA GGA GGA ACA GTT CGT GTG TTT GAC TTA TCT
leu ala asp lys ile ala his lys thr gly gly gly thr val arg val phe asp leu ser
3001 / 1001                             3031 / 1011
CTT TCT AAA GGA GGC AAG GAA ACA CAT GTC AAT GGA GAA CGA ACT GTT CGG CTC GCG CTT
leu ser lys gly gly lys glu thr his Val asn gly glu arg thr Val arg leu ala leu
3061 / 1021                             3091 / 1031
GGG CAG ACT GGC TCA GAT GTT CAC GTC TAT CAC GTA AAG GAA AAT GGC GAC CTT GAG CGT
gly gln thr gly ser asp Val his val tyr his val lys glu asn gly asp leu glu arg
3121 / 1041                             3151 / 1051
ATT CCT TCT AAA GTT GAA AAT GGG CAA GTT GTT TTT AAA ACG AAC CAC TTC AGT TTG TTT
ile pro ser lys Val glu asn gly gln val val phe lys thr asn his phe ser leu phe
```

FIG.8F

```
3181 / 1061                                3211 / 1071
GCG ATT AAG ACA CTT TCT AAG GAT CAA AAT GTT ACT CCA CCG AAG CAG ACT AAA CCT TCT
ala ile lys thr leu ser lys asp gln asn val thr pro pro lys gln thr lys pro ser
3241 / 1081                                3271 / 1091
ACC CAA GGC AGT CAA GTA GAG ATT GCA GAG AGT CAA ACT GGA AAA TTC CAG ACT AAA GCA
thr gln gly ser gln val glu ile ala glu ser gln thr gly lys phe gln ser lys ala
3301 / 1101                                3331 / 1111
GCT AAT CAT AAA CCA CTG GCT ACT GGA AAT GAA ACA GTG GCA AAA GGA AAT CCT ACA TCA
ala asn his lys ala leu ala thr gly asn glu thr Val ala lys gly asn pro thr ser
3361 / 1121
ACA ACG GAA AAG AAA ctc gag cac cac
thr thr glu lys lys leu glu his his
```

FIG.8G

```
pnv231 -> 1-phase Translation
DNA sequence     3492 b.p.   atgtttaaatct ... AGAAGAAAATCA   linear

1   /   1                                  31   /   11
atg ttt aaa tct aat tat gaa aga aaa atg cgt tat tcc att cgt aaa ttt agt gta gga
met phe lys ser asn tyr glu arg lys met arg tyr ser ile arg lys phe ser val gly
61   /   21                                 91   /   31
gta gct agt gta gcg gta gct agt ttg ttc atg gga agc gtt gct cat gca AGT GAG CTT
val ala ser val ala val ala ser leu phe met gly ser val ala his ala ser glu leu
121  /   41                                 151  /   51
GTA AAG CAC GAT AGT GTG AAG ACT ACC GAG GTT GCA GCT AAG CCC TAT CCA AGT ATG GCT
val lys asp asp ser val lys thr thr glu val ala ala lys pro tyr pro ser met ala
181  /   61                                 211  /   71
CAA ACA GAT CAA GGA AAT AAT TCA TCA TCC TCG GAA CTT GAG ACA ACA AAG ATC GAA ATT
gln thr asp gln gly asn asn ser ser ser ser glu leu glu thr thr lys met glu ile
241  /   81                                 271  /   91
CCT ACA ACA GAC ATA AAA AAA GCT GTT GAA CCG CTC GAG AAA ACA GCT GGG GAA ACA TCT
pro thr thr asp ile lys lys ala val glu pro val glu lys thr ala gly glu thr ser
301  /  101                                 331  /  111
GCC ACT GAT ACT GGA AAA CGA GAG AAA CAA TTA CAA CAA TGG AAA AAT AAT CTA AAA AAT
ala thr asp thr gly lys arg glu lys gln leu gln gln trp lys asn asn leu lys asn
361  /  121                                 391  /  131
GAT GTG CAT AAC ACA ATT CTA TCT CAT GAA CAG AAA AAT GAG TTT AAA ACA AAA ATT GAT
asp val asp asn thr ile leu ser his glu gln lys asn glu phe lys thr lys ile asp
421  /  141                                 451  /  151
GAA ACA AAT GAT TCT GAT GCA TTA TTA GAA TTA GAA AAT CAA TTT AAC GAA ACT AAT AGA
glu thr asn asp ser asp ala leu leu glu leu glu asn gln phe asn glu thr asn arg
```

FIG.9A

```
481 / 161                               511 / 171
CTG TTA CAC ATC AAA CAA CAT GAA GAA GTT GAG AAA GAT AAG AAA GCT AAG CAA CAG AAA
leu leu his ile lys gln his glu glu val glu lys asp lys lys ala lys gln gln lys
541 / 181                               571 / 191
ACT CTG AAA CAG TCA GAT ACC AAA GTA GAT CTA AGC AAT ATT GAC AAA GAG CTT AAT CAT
thr leu lys gln ser asp thr lys val asp leu ser asn ile asp lys glu leu asn his
601 / 201                               631 / 211
CAA AAA AGT CAA GTT GAA Acc ATG GCA GAG CAA ctc GGg ATC ACA AAT GAA GAT AAA GAT
gln lys ser gln val glu thr met ala glu gln leu gly ile thr asn glu asp lys asp
661 / 221                               691 / 231
TCT ATG CTG AAA AAA ATC GAA GAT ATT CGT AAA CAA GCT CAA CAA GCA GAT AAA AAA GAA
ser met leu lys lys ile glu asp ile arg lys gln ala gln gln ala asp lys lys glu
721 / 241                               751 / 251
GAT GCC GAA GTA AAG GTT CGT GAA GAA CTA GGT AAA CTC TTT ACT TCA ACT AAA GCT GGT
asp ala glu val lys val arg glu glu leu gly lys leu phe ser ser thr lys ala gly
781 / 261                               811 / 271
CTG GAT CAA GAA ATT CAA GAG CAT GTG AAG AAA GAA ACG ACT AGT GAG GAA AAT ACT CAG
leu asp gln glu ile gln glu his val lys lys glu thr ser ser glu glu asn thr gln
841 / 281                               871 / 291
AAA GTT GAT GAA CAC TAT CCT AAT AGC CTT CAG AAC CTT GCT CAA AAA TCT CTT GAA GAA
lys val asp glu his tyr ala asn ser leu gln asn leu ala gln lys ser leu glu glu
901 / 301                               931 / 311
CTA GAT AAG GCA ACT ACC AAT GAA CAA GCT ACA CAA GTT AAA AAT CAA TTC TTA GAA AAC
leu asp lys ala thr thr asn glu gln ala thr gln val lys asn gln phe leu glu asn
961 / 321                                991 / 331
GCT CAA AAG CTC AAA GAA ATA CAA CCT CTT ATC AAA GAA ACG AAT GTG AAA TTG TAT AAG
ala gln lys leu lys glu ile gln pro leu ile lys glu thr asn val lys leu tyr lys
```

FIG.9B

```
1021 /  341                                 1051 /  351
GCT ATG AGT GAG AGC TTG GAG CAG GTT GAG AAG CAA TTA AAA CAT AAT TCG CAA GCT AAT
ala met ser glu ser leu glu gln val glu lys glu leu lys his asn ser glu ala asn
1081 /  361                                 1111 /  371
TTA GAA GAT TTG GTT GCG AAA TCT AAA GAA ATC GTA AGA GAA TAC GAA GGA AAA CTT AAT
leu glu asp leu val ala lys ser lys glu ile val arg glu tyr glu gly lys leu asn
1141 /  381                                 1171 /  391
CAA TCT AAA AAT CTT CCA GAA TTA AAG CAA CTA GAA GAG GAA GCT CAT TCG AAG TTG AAA
gln ser lys asn leu pro glu leu lys gln leu glu glu glu ala his ser lys leu lys
1201 /  401                                 1231 /  411
CAA GTT GTG GAG GAT TTT AGA AAA AAA TTT AAA ACC TCA GAG CAA GTG ACA CCA AAA AAA
gln val val glu asp phe arg lys lys phe lys thr ser glu gln val thr pro lys lys
1261 /  421                                 1291 /  431
CGT GTC AAA CGA GAT TTA GCT GCT AAT GAA AAT AAT CAA CAA AAG ATT GAG TTA ACA GTT
arg val lys arg asp leu ala ala asn glu asn asn gln gln lys ile glu leu thr val
1321 /  441                                 1351 /  451
TCA CCA GAG AAT ATC ACT GTA TAT GAA GGT GAA GAC CTG AAA TTT ACA CTC ACA GCT AAA
ser pro glu asn ile thr val tyr glu gly glu asp val lys phe thr val thr ala lys
1381 /  461                                 1411 /  471
AGT GAT TCG AAG ACG ACG TTG GAC TTC AGT GAT CTT TTA ACA AAA TAT AAT CCG TCT GTA
ser asp ser lys thr thr leu asp phe ser asp leu leu thr lys tyr asn pro ser val
1441 /  481                                 1471 /  491
TCA GAT AGA ATT AGT ACA AAT TAT AAG ACT AAC ACG GAT AAT CAT AAG ATT GCC GAA ATC
ser asp arg ile ser thr asn tyr lys thr asn thr asp asn his lys ile ala glu ile
1501 /  501                                 1531 /  511
ACT ATC AAG AAT TTG AAG CTA AAT GAA AGT CAA ACA GTG ACT CTA AAA GCT AAA GAT GAT
thr ile lys asn leu lys leu asn glu ser gln thr val thr leu lys ala lys asp asp
```

FIG.9C

```
1561 /  521                             1591 /  531
TCT GGC AAT GTA GTT CAA AAA ACA TTC ACT ATT ACA GTG CAA AAG AAA GAG GAG AAA CAA
ser gly asn val val glu lys thr phe thr ile thr val gln lys lys glu glu lys gln
1621 /  541                             1651 /  551
GTT CCT AAA ACA CCA GAG CAG AAA GAT TCT AAA ACG GAA GAA AAG GTT CCT CAA GAA CCA
val pro lys thr pro glu gln lys asp ser lys thr glu glu lys val pro gln glu pro
1681 /  561                             1711 /  571
AAA TCA AAT GAC AAG AAT CAA TTA CAA GAG TTG ATT AAA TCA GCT CAA CAA CAA CTG GAA
lys ser asn asp lys asn gln leu gln glu leu ile lys ser ala gln gln glu leu glu
1741 /  581                             1771 /  591
AAG TTA GAA AAA GCA ATA AAA GAA TTA ATG GAG CAA CCA GAG ATT CCA TCC AAT CCA GAG
lys leu glu lys ala ile lys glu leu met glu gln pro glu ile pro ser asn pro glu
1801 /  601                             1831 /  611
TAT GGT ATT CAA AAA TCT ATT TGG GAG TCA CAA AAA GAG CCT ATC CAG GAA GCC ATA ACA
tyr gly ile gln lys ser ile trp glu ser gln lys glu pro ile gln glu ala ile thr
1861 /  621                             1891 /  631
AGT TTT AAG AAG ATT ATT GGT GAT TCA TCT TCA AAA TAC TAC ACA GAG CAC TAT TTT AAC
ser phe lys lys ile ile gly asp ser ser ser lys tyr tyr thr glu his tyr phe asn
1921 /  641                             1951 /  651
AAA TAT AAA TCT GAT TTT ATG AAT TAT CAA CTT CAT GCA CAA ATG GAG ATG CTG ACT AGA
lys tyr lys ser asp phe met asn tyr gln leu his ala gln met glu met leu thr arg
1981 /  661                             2011 /  671
AAA GTG GTT CAG TAT ATC AAC AAA TAT CCT GAT AAT GCA GAA ATT AAA AAG ATA TTT GAG
lys val val gln tyr met asn lys tyr pro asp asn ala glu ile lys lys ile phe glu
2041 /  681                             2071 /  691
TCA GAT ATG AAG AGA ACG AAA GAA GAT AAT TAC GGA AGT TTA GAA AAT GAT GCT TTG AAA
ser asp met lys arg thr lys glu asp asn tyr gly ser leu glu asn asp ala leu lys
```

FIG.9D

```
2101 /  701                             2131 /  711
GGC TAT TTT GAG AAA TAT TTC CTT ACA CCA TTT AAT AAA ATT AAG CAG ATT GTA GAT GAT
gly tyr phe glu lys tyr phe leu thr pro phe asn lys ile lys gln ile val asp asp
2161 /  721                             2191 /  731
TTG GAT AAA AAA GTA GAA CAA GAT CAG CCA GCA CCA ATT CCG GAA AAT TCA GAA ATG GAT
leu asp lys lys val glu gln asp gln pro ala pro ile pro glu asn ser glu met asp
2221 /  741                             2251 /  751
CAG GCT AAG GAA AAG GCT AAG ATT GCT GTA TCG AAG TAT ATG AGT AAG GTT TTA GAT GGA
gln ala lys glu lys ala lys ile ala val ser lys tyr met ser lys val leu asp gly
2281 /  761                             2311 /  771
GTT CAT CAA CAT CTG CAG AAG AAA AAT AAC ACT AAA ATT GTT GAT CTT TTT AAG GAA CTT
val his gln his leu gln lys lys asn asn ser lys ile val asp leu phe lys glu leu
2341 /  781                             2371 /  791
GAA GCG ATT AAA CAA CAA ACT ATT TTT GAT ATT GAC AAT GCA AAG ACT GAA GTA GAG ATT
glu ala ile lys gln gln thr ile phe asp ile asp asn ala lys chr glu val glu ile
2401 /  801                             2431 /  811
GAT AAC TTA GTA CAC GAT GCA TTC TCA AAA ATG AAT GCT ACT GTT GCT AAA TTT CAA AAA
asp asn leu val his asp ala phe ser lys met asn ala thr val ala lys phe gln lys
2461 /  821                             2491 /  831
GGT CTA GAG ACA AAT ACG CCA GAA ACT CCA CAT ACA CCC AAG ATT CCA GAG CTA CCT CAA
gly leu glu thr asn thr pro glu thr pro asp thr pro lys ile pro glu leu pro gln
2521 /  841                             2551 /  851
GCC CCA GAT ACA CCG CAG GCT CCA GAC ACA CCG CAT GTT CCG GAA TCA CCA AAG GCC CCA
ala pro asp thr pro gln ala pro asp thr pro his val pro glu ser pro lys ala pro
2581 /  861                             2611 /  871
GAA GCA CCC CGT GTT CCG GAA TCA CCA AAC ACT CCA GAA GCA CCG CAT GTT CCC CAA TCA
glu ala pro arg val pro glu ser pro lys thr pro glu ala pro his val pro glu ser
```

FIG.9E

```
2641 /  881                                       2671 /  891
CCA AAG GCC CCA GAA GCA CCG CGT GTT CCG GAA TCA CCA AAC ACT CCA GAA GCA CCG CAT
pro lys ala pro glu ala pro arg val pro glu ser pro lys thr pro glu ala pro his
2701 /  901                                       2731 /  911
GTT CCG GAA TCA CCA AAG ACT CCA GAA GCA CCA AAG ATT CCG GAA CCC CCT AAG ACT CCA
val pro glu ser pro lys thr pro glu ala pro lys ile pro glu pro pro lys thr pro
2761 /  921                                       2791 /  931
GAC GTC CCT AAG CTT CCA GAC GTC CCT AAG CTT CCA GAC GTC CCT AAG CTT CCA GAT GCA
asp val pro lys leu pro asp val pro lys leu pro asp val pro lys leu pro asp ala
2821 /  941                                       2851 /  951
CCC AAG TTA CCA GAT GGG TTA AAT AAA GTT GGA CAA GCA GTA TTT ACA TCA ACT GAT GGA
pro lys leu pro asp gly leu asn lys val gly gln ala val phe thr ser thr asp gly
2881 /  961                                       2911 /  971
AAT ACT AAG GTT ACG GTT GTA TTT GAT AAA CCT ACA GAT GCT GAT AAG TTA CAT CTC AAG
asn thr lys val thr val val phe asp lys pro thr asp ala asp lys leu his leu lys
2941 /  981                                       2971 /  991
GAA CTA ACG ACG AAA GAG TTG GCT GAT AAA ATT GCT CAT AAA ACA GGA GGA GGA ACA GTT
glu val thr thr lys glu leu ala asp lys ile ala his lys thr gly gly gly thr val
3001 / 1001                                       3031 / 1011
CGT GTG TTT GAC TTA TCT CTT TCT AAA GGA GGC AAG GAA ACA CAT GTC AAT GGA CAA CGA
arg val phe asp leu ser leu ser lys gly gly lys glu thr his val asn gly glu arg
3061 / 1021                                       3091 / 1031
ACT GTT CGG CTC GCG CTT GGG CAG ACT GGC TCA GAT GTT CAC GTC TAT CAC GTA AAG GAA
thr val arg leu ala leu gly gln thr gly ser asp val his val tyr his val lys glu
3121 / 1041                                       3151 / 1051
AAT GGC GAC CTT GAG CGT ATT CCT TCT AAA GTT GAA AAT GGG CAA GTT GTT TTT AAA ACG
asn gly asp leu glu arg ile pro ser lys val glu asn gly gln val val phe lys thr
```

FIG.9F

```
3181 / 1061                                  3211 / 1071
AAC CAC TTC AGT TTG TTT GCG ATT AAG ACA CTT TCT AAG GAT CAA AAT GTT ACT CCA CCG
asn his phe ser leu phe ala ile lys thr leu ser lys asp gln asn val thr pro pro
3241 / 1081                                  3271 / 1091
AAG CAG ACT AAA CCT TCT ACC CAA GGC AGT CAA GTA GAG ATT GCA GAG AGT CAA ACT GGA
lys gln thr lys pro ser Lhr gln gly ser gln val glu ile ala glu ser gln thr gly
3301 / 1101                                  3331 / 1111
AAA TTC CAG AGT AAA GCA GCT AAT CAT AAA GCA CTC GCT ACT GGA AAT GAA ACA GTG GCA
lys phe gln ser lys ala ala asn his lys ala leu ala thr gly asn glu thr val ala
3361 / 1121                                  3391 / 1131
AAA GGA AAT CCT ACA TCA ACA ACG CAA AAG AAA TTG CCA TAT ACA GGA GTG GCA TCT AAT
lys gly asn pro thr ser thr thr glu lys lys leu pro tyr thr gly val ala ser asn
3421 / 1141                                  3451 / 1151
CTA GTT CTT GAA ATT ATG GGT CTC CTT GGT TTG ATT GGA ACT TCA TTC ATC GCA ATG AAA
leu val leu glu ile met gly leu leu gly leu ile gly thr ser phe ile ala met lys
3481 / 1161
AGA AGA AAA TCA
arg arg lys ser
```

FIG.9G

NON-IGA FC BINDING FORMS OF THE GROUP B STREPTOCOCCAL β ANTIGENS

This application claims benefit to Provisional Application No. 60/024,707 filed Sep.. 6, 1996.

BACKGROUND OF THE INVENTION

1. Field of the Invention

The present invention concerns the construction of a protein having a reduced or eliminated ability to bind human IgA, but that retains the immunological properties useful for formulating a conjugate vaccine against Group B streptococci.

2. Related Art

Streptococci are a large and varied set of gram-positive bacteria which have been ordered into several groups based on the antigenicity and structure of their cell wall polysaccharide (Lancefield, R. C., *J. Exp. Med.* 57:571–595 (1933); Lancefield, R. C., *Proc. Soc. Exp. Biol. and Med.* 38:473–478 (1938)). Two of these groups have been associated with serious human infections. Those that have been classified into Group A streptococci are the bacteria that people are most familiar and are the organisms which cause "strep throat." Organisms of Group A streptococci also are associated with the more serious infections of rheumatic fever, streptococcal impetigo, and sepsis.

Group B streptococci were not known as a human pathogen in standard medical textbooks until the early 1970's. Since that time, studies have shown that Group B streptococci are an important perinatal pathogen in both the United States as well as the developing countries (Smith, A. L. and J. Haas, *Infections of the Central Nervous System,* Raven Press, Ltd., New York. (1991) p. 313–333). Systemic Group B streptococcal infections during the first two months of life affect approximately three out of every 1000 births (Dillon, H. C., Jr., et al., *J Pediat.* 110:31–36 (1987)), resulting in 11,000 cases annually in the United States. These infections cause symptoms of congenital pneumonia, sepsis, and meningitis. A substantial number of these infants die or have permanent neurological sequelae. Furthermore, these Group B streptococcal infections may be implicated in the high pregnancy-related morbidity which occurs in nearly 50,000 women annually. Others who are at risk from Group B streptococcal infections include those who either congenitally, chemotherapeutically, or by other means, have an altered immune response.

Group B streptococci can be further classified into several different types based on the bacteria's capsular polysaccharide. The most pathogenically important of these different types are streptococci having types Ia, Ib, II, or III capsular polysaccharides. Group B streptococci of these four types represent over 90% of all reported cases. The structure of each of these various polysaccharide types has been elucidated and characterized (Jennings, H. J., et al., *Biochemistry* 22:1258–1263 (1983); Jennings, H. J., et al., *Can. J. Biochem.* 58:112–120(1980); Jennings, H. J., et al., *Proc. Nat. Acad. Sci. USA.* 77:2931–2935 (1980); Jennings, H. J., et al., *J. Biol. Chem.* 258:1793–1798 (1983); Wessels, M. R., et al., *J. Biol. Chem.* 262:8262–8267 (1987)). As is found with many other human bacterial pathogens, it has been ascertained that the capsular polysaccharides of Group B streptococci, when used as vaccines, provide very effective, efficacious protection against infections with these bacteria. This was first noted by Lancefield (Lancefield, R. C., et al., *J. Exp. Med.* 142:165–179 (1975)) and more recently in the numerous studies of Kasper and coworkers (Baker, C. J., et al., *N. Engl. J. Med.* 319:1180–1185 (1988); Baltimore, R. S., et al., *J. Infect. Dis.* 140:81–86 (1979); Kasper, D. L., et al., *J. Exp. Med.* 149:327–339 (1979); Madoff, L. C., et al., *J. Clin. Invest.* 94:286–292 (1994); Marques, M. B., et al., *Infect. Immun.* 62:1593–1599 (1994); Wessels, M. R., et al., *J. Clin. Invest.* 86:1428–1433 (1990); Wessels, M. R., et al., *Infect. Immun.* 61:4760–4766 (1993); Wyle, S. A., et al., *J. Infect. Dis.* 126:514–522 (1972)). However, much like many other capsular polysaccharide vaccines (Anderson, P., et al., *J. Clin. Invest.* 51:39–44 (1972); Gold, R., et al., *J. Clin. Invest.* 56:1536–1547 (1975); Gold, R., et al., *J. Infect. Dis.* 136S:S31–S35 (1977); Gold, R. M., et al., *J. Infect. Dis.* 138:731–735 (1978); Mäkelä, P. R. H., et al., *J. Infect. Dis.* 136:S43–50 (1977); Peltola, A., et al., *Pediatrics* 60:730–737 (1977); Peltola, H., et al. *N. Engl. J. Med.* 297:686–691 (1977)), vaccines formulated from pure type Ia, Ib, II, and III capsular carbohydrates are relatively poor immunogens and have very little efficacy in children under the age of 18 months (Baker, C. J. and D. L. Kasper. *Rev. Inf. Dis.* 7:458–467 (1985); Baker, C. J., et al., *N. Engl. J. Med.* 319:1180–1185 (1988); Baker, C. J., et al., *New Engl. J. Med.* 322:1857–1860 (1990)). These pure polysaccharides are classified as T cell independent antigens because they induce a similar immunological response in animals devoid of T lymphocytes (Howard, J. G., et al., *Cell. Immunol.* 2:614–626 (1971)). It is thought that these polysaccharides do not evoke a secondary booster response because they do not interact with T cells, and therefore fail to provoke a subsequent "helper response" via the secretion of various cytokines. For this reason, each consecutive administration of the polysaccharide as a vaccine results in the release of a constant amount of antibodies, while a T cell dependent antigen would elicit an ever increasing concentration of antibodies each time it was administered.

Goebel and Avery found in 1931 that by covalently linking a pure polysaccharide to a protein that they could evoke an immune response to the polysaccharide which could not be accomplished using the polysaccharide alone (Avery, O. T. and W. F. Goebel, *J. Exp. Med.* 54:437–447 (1931); Goebel, W. F. and O. T. Avery, *J. Exp. Med.* 54:431–436 (1931)). These observations initiated and formed the basis of the current conjugate vaccine technology. Numerous studies have followed and show that when polysaccharides are coupled to proteins prior to their administration as vaccines, the immune response to the polysaccharides changes from a T independent response to a T dependent response (see Dick, W. E., Jr. and M. Beurret, Glycoconjugates of bacterial carbohydrate antigens In: *Contributions to Microbiology and Immunology.* Cruse et al., eds., (1989) p. 48–114; Jennings, H. J. and R. K. Sood, *Neoglycoconjugates: Preparation and Applications.* Y. C. Lee and R. T. Lee, eds., Academic Press, New York. (1994) p. 325–371; Robbins, J. B. and R. Schneerson, *J. Infect. Dis.* 161:821–832 (1990)for reviews). Currently, most of these polysaccharide-protein conjugate vaccines are formulated with well known proteins such as tetanus toxoid and diphtheria toxoid or mutants thereof. These proteins were originally used because they were already licensed for human use and were well characterized. However, as more and more polysaccharides were coupled to these proteins and used as vaccines, interference between the various vaccines which used the same protein became apparent. For example, if several different polysaccharides were linked to tetanus toxoid and given sequentially, the immune response to the first administered polysaccharide conjugate would be much larger than the last. If, however, each of the polysaccharides were coupled to a different protein and administered sequentially, the immune response to each of the polysaccharides would be the same. Carrier suppression is the term used to describe this observed phenomenon. One approach to overcome this problem is to match the protein and polysaccharide so that they are derived from the same organism.

Among the various antigens used to classify and subgroup Group B streptococci, one was a protein known as the Ibc antigen. This protein antigen was first described by Wilkinson and Eagon in 1971 (Wilkinson, H. W. and R. G. Eagon, *Infect. Immun.* 4:596–604 (1971)) and was known to be made up of two distinct proteins designated as alpha and beta. Later, the Ibc antigen was shown to be effective when used as a vaccine antigen in a mouse model of infection by Lancefield and co-workers (Lancefield, R. C., et al., *J. Exp. Med.* 142:165–179 (1975)). The isolation, purification and functional characterization of the beta antigen (Cβ) protein of Group B streptococci was accomplished by Russell-Jones, et al. (Russell-Jones, G. J. and E. C. Gotschlich, *J. Exp. Med.* 160:1476–1484 (1984); Russell-Jones, G. J., et al., *J. Exp. Med.* 160:1467–1475 (1984))(see U.S. Pat. No. 4,757,134)). They could demonstrate that one of the properties of the Cβ protein was to bind specifically to human IgA immunoglobulin. The binding site on the IgA molecule was localized to the Fc portion of the heavy chain of this immunoglobulin. They further showed that the Cβ protein consisted of a single polypeptide having an estimated molecular weight of 130,000 daltons. The gene responsible for the expression of the Cβ protein was cloned (Cleat, P. H. and K. N. Timmis, *Infect. Immun.* 55:1151–1155 (1987)) and sequenced (Jerlström, P. G., et al., *Molec. Microbiol.* 5:843–849 (1991)) by a group led by Timmis. His later study demonstrated that the IgA binding activity could be assigned to a 746 bp DNA fragment of the gene defined by a leading BglII restriction endonuclease cleavage site and ending with a HpaI restriction endonuclease cleavage site.

As stated previously, the 1975 Lancefield study showed that the Ibc antigen was an effective vaccine antigen in a mouse model of Group B streptococcal infection (Lancefield, R. C., et al., *J. Exp. Med.* 142:165–179 (1975)). It was not clear at the time whether the alpha or beta protein component of the Ibc antigen was responsible for this protection. Madoff et al., began to shed light on this question and demonstrated that the purified Cβ protein used as a vaccine could protect infant mice from experimental infection with Group B streptococci expressing this protein (Madoff, L. C., et al., *Infect. Immun.* 60:4989–4994 (1992)). Madoff et al., then went on to show that when they coupled a Type III streptococcal capsular polysaccharide to the Cβ protein, producing a conjugate vaccine, this vaccine would protect infant mice against infection with either a Type III Group B streptococci (expressing no Cβ) or a Type Ib Group B streptococci (expressing Cβ but lacking a Type III capsular polysaccharide) (Madoff, L. C., et al., *J. Clin. Invest.* 94:286–292 (1994)). Thus, such a Cβ protein conjugate vaccine served several functions: the polysaccharide elicited protective antibodies to the polysaccharide capsule and the Cβ protein evoked protective antibodies to the protein as well as modified the immune response to the polysaccharide from a T independent response to a T dependent response.

This polysaccharide-Cβ protein conjugate strategy works well in mice. But clearly, the goal is to protect humans against Group B streptococcal infections. The only caveat with using the same strategy in humans is that the Cβ protein binds human IgA immunoglobulins non-specifically (Cβ does not bind mouse IgA). This human IgA binding activity of Cβ could diminish the efficacy of a polysaccharide-Cβ protein conjugate vaccine for humans, as antigens bound to IgA can be cleared from the system so rapidly that an antigen-specific antibody response is not produced. Furthermore, potentially protective epitopes on the Cβ protein could be hidden when the human IgA binds to the Cβ molecule. Thus, it would be advantageous to obtain a mutant Cβ protein which lacks the IgA binding capacity but retains as much of the native structure as possible.

With this goal in mind, several groups have attempted to determine the IgA binding region of the Cβ protein. Jerlström et al. (*Molec. Microbiol.* 5:843–849 (1991)) used experiments wherein subfragments of the Cβ protein were expressed as fusion proteins to identify two regions of the Cβ protein capable of binding IgA. These experiments localized the IgA binding domains to a 747 bp BglII-HpaI fragment and a 1461 bp HpaI-HindIII fragment of the Cβ protein. Furthermore, International Patent Application No. PCT/US/06111 describes the isolation of a Cβ protein bearing a deletion of a region that binds IgA.

SUMMARY OF THE INVENTION

The invention relates to a mutant Cβ protein, wherein the IgA binding by the Cβ protein is reduced or eliminated, while the antigenicity of the protein when administered either alone or as part of a polysaccharide-protein conjugate is substantially retained.

In particular, the invention relates to a mutant Cβ protein comprising the amino acid sequence $A\text{-}X_1X_2X_3X_4X_5X_6X_7X_8X_9X_{10}X_{11}X_{12}\text{-}B$, wherein A comprises amino acids 1–164 of the sequence shown in FIG. 1 (SEQ ID NO: 2), B represents a sequence starting from amino acid 177 and terminating at an amino acid between residue 1094 and 1127, inclusive, of the sequence shown in FIG. 1 (SEQ ID NO: 2), and $X_1$–$X_{12}$ are each selected independently from the group consisting of Ala, Val, Leu, Ile, Pro, Met, Phe, Trp, a bond, and the wild type amino acid found at the corresponding position of the sequence shown in FIG. 1 (SEQ ID NO: 2), wherein said amino acid positions are numbered from the first amino acid of the native amino acid sequence encoding said protein, with the proviso that at least one of $X_1$ through $X_{12}$, inclusive, is other than the wild type amino acid.

The invention also relates to a polynucleotide molecule encoding a mutant Cβ protein, as well as vectors comprising such polynucleotide molecules, and host cells transformed therewith.

The invention also relates to a conjugate comprising the mutant Cβ protein covalently conjugated to a capsular polysaccharide.

The invention also relates to a vaccine comprising the mutant Cβ protein of the invention and a pharmaceutically acceptable carrier.

The invention also relates to a method of inducing an immune response in an animal, comprising administering the vaccine of the invention to an animal in an effective amount.

BRIEF DESCRIPTION OF THE FIGURES

FIG. 1 (SEQ ID NOS: 1 and 2) shows the DNA sequence and deduced amino acid sequence of wild type Cβ1 (Jerlström, P. G., et al., *Molec. Microbiol.* 5:843–849 (1991)). The BglII and PstI sites shown in FIGS. 2, 3 and 4 are identified.

FIG. 3 is a map of the region of the Cβ gene which encodes the IgA binding site of the Cβ protein; 2 amino acid substitutions are indicated, generating mutant nv34qp (SEQ ID NO: 21)(see Table 1).

FIGS. 6A, 6B–6G (SEQ ID NOS: 3 and 4) show the complete DNA sequence of the gene encoding Cβ mutant dgb2 (see Table 1), as well as the deduced amino acid sequence of this mutant. The mutations are underlined.

FIGS. 7A, 7B–7F (SEQ ID NOS: 5 and 6) show the complete DNA sequence of the gene encoding Cβ mutant nv34qp (see Table 1), as well as the deduced amino acid sequence of this mutant. The mutations are underlined.

FIGS. 8A, 8B–8G (SEQ ID NOS: 7 and 8) show the complete DNA sequence of the gene encoding Cβ mutant dgb1 (see Table 1), as well as the deduced amino acid sequence of this mutant.

FIGS. 9A, 9B–9G (SEQ ID NOS: 9 and 10) show the complete DNA sequence of the gene encoding Cβ mutant pnv231 (see Table 1), as well as the deduced amino acid sequence of this mutant. The mutations are underlined.

DETAILED DESCRIPTION OF THE PREFERRED EMBODIMENTS

Figure 2:
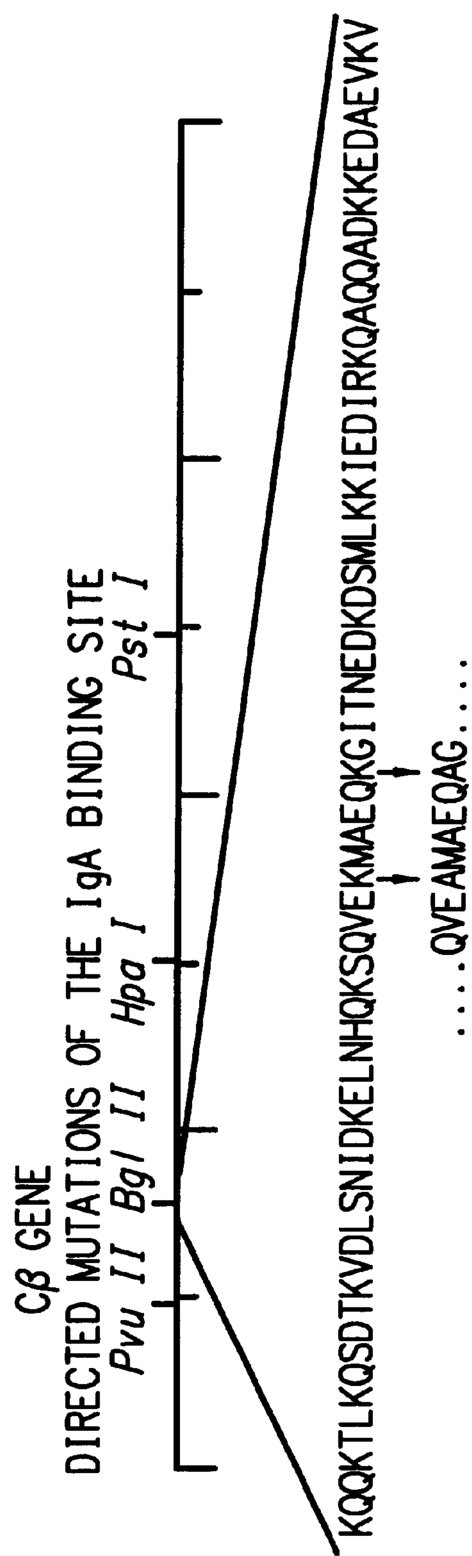
FIG. 2 is a map of the region of the Cβ gene which encodes the IgA binding site of the Cβ protein; 2 amino acid substitutions are indicated, generating mutant dgb2 (SEQ ID NO: 22)(see Table 1).

The invention relates to a mutant Cβ protein of the group B streptococcal (GBS) beta antigen, wherein IgA binding by the Cβ protein is reduced or eliminated and wherein at least a majority of the antigenicity of the protein is retained.

It has been discovered that mutation of a region of the Cβ protein located between about amino acid residues 163 and 176 of the wildtype Cβ sequence shown in FIG. 1 (SEQ ID NO:2) results in a Cβ protein which has reduced or eliminated IgA binding properties, but which retains enough of its tertiary structure to maintain the majority of its antigenicity (see Examples 4 and 5).

As the region of the Cβ polypeptide has been found which is responsible for IgA binding, and as it has been demonstrated in the Examples below that amino acid substitutions or deletions in this region reduce or eliminate IgA binding while maintaining antigenicity of the protein, those of ordinary skill in the art will understand how to alter the amino acid sequence of the Cβ polypeptide so as to achieve the objects of the invention. Appropriate amino acid substitutions which eliminate IgA binding will include replacement of one or more residues with an amino acid having different properties. For example, a strongly hydrophilic amino acid can be replaced with a strongly hydrophobic amino acid. Amino acids which can be grouped together include the aliphatic amino acids Ala, Val, Leu and Ile, the hydroxyl residues Ser and Thr, the acidic residues Asp and Glu, the amide residues Asn and Gln, the basic residues Lys and Arg and the aromatic residues Phe and Tyr. Thus, those of ordinary skill in the art will understand how to determine suitable amino acid substitutions or deletions in the region between about residues 163 and 176 in the Cβ protein in order to reduce or eliminate IgA binding.

Further guidance concerning which amino acid changes are likely to have a significant deleterious effect on a function can be found in Bowie, J. U., et al., "Deciphering the Message in Protein Sequences: Tolerance to Amino Acid Substitutions," *Science* 247:1306–1310 (1990).

Thus, in particular, the invention relates to a mutant group B streptococcal (GBS) beta antigen, Cβ, comprising the amino acid sequence $A\text{-}X_1X_2X_3X_4X_5X_6X_7X_8X_9X_{10}X_{11}X_{12}\text{-}B$, wherein A comprises amino acids 1–164 of the sequence shown in FIG. 1 (SEQ ID NO: 2), B represents a sequence starting from amino acid 177 and terminating at an amino acid between residue 1094 and 1127, inclusive, of the sequence shown in FIG. 1 (SEQ ID NO: 2), and $X_1$–$X_{12}$ are each selected independently from the group consisting of Ala, Arg, Asp, Val, Leu, Ile, Pro, Met, Phe, Trp, a bond, and the wild type amino acid found at the corresponding position of the sequence shown in FIG. 1 (SEQ ID NO: 2), wherein said amino acid positions are numbered from the first amino acid of the native amino acid sequence encoding said protein, with the proviso that at least one of $X_1$ through $X_{12}$, inclusive, is other than the wild type amino acid. In a particularly preferred mutant Cβ protein, amino acids $X_7$ and $X_{12}$ are Ala. In another preferred mutant, amino acids $X_4$ and $X_{11}$ are Pro. In another preferred mutant, amino acid $X_7$ is Thr and amino acid $X_{12}$ is Leu. In a more preferred mutant, amino acids $X_5$, $X_7$, $X_8$, $X_{10}$, $X_{11}$ and $X_{12}$ are each replaced with a bond.

As the Cβ protein is, in its wild type state, membrane bound, it is possible to improve purification of the above-mentioned Cβ mutants by eliminating the hydrophobic residues of the transmembrane domain of the Cβ protein (the transmembrane domain corresponds to residues 1095–1127 of the sequence shown in FIG. 1 (SEQ ID NO: 2)). This can be accomplished by substitution of non-hydrophobic residues for the hydrophobic residues (residues 1108–1116 of the sequence shown in FIG. 1 (SEQ ID NO: 2)) or by deletion of the hydrophobic residues. While purification of membrane-bound Cβ requires the use of detergent, a mutant Cβ which lacks the hydrophobic membrane spanning region can be purified without using detergent. Thus, the invention also relates to a mutant Cβ wherein the nine hydrophobic residues making up the transmembrane domain are deleted or replaced by non-hydrophobic amino acids.

It has been discovered that the IgA-binding ability of Cβ may require dimerization of Cβ. Thus, even where the IgA-binding region of Cβ is not mutated as described above, mutation of the region of Cβ which is believed to be required for dimerization can result in a form of Cβ that cannot bind IgA. Deletion of a portion of Cβ from residue 729 to the C-terminus of the sequence shown in FIG. 1 (SEQ ID NO: 2) eliminates dimerization Cβ. The results of experiments supporting this finding may be found in Table 1. (IgAbs+ (SEQ ID NO: 11); dgb6 (SEQ ID NO: 12); dgb6p (SEQ ID NO: 13); dgb7 (SEQ ID NO: 14); dgb7p (SEQ ID NO: 15); dgb8 (SEQ ID NO: 16); dgb8p (SEQ ID NO: 17); dgb10 (SEQ ID NO: 18); dgb12 (SEQ ID NO: 19); dgb11 (SEQ ID NO: 20); nv34qp (SEQ ID NO: 21); dgb2 (SEQ ID NO: 22); dgb1 (SEQ ID NO: 23); and pnv231 (SEQ ID NO: 24)). Several fragments of Cβ were inserted into each of two different vectors. Where sequences shown in the table are preceded or followed by an outward facing bracket, this indicates that the Cβ sequence does not extend further on that end of the fragment, i.e. that the nucleotide sequence inserted into the vector encodes only those amino acids shown, and no more of the Cβ sequence. Where sequences shown in the table are preceded or followed by ellipses, this indicates that the remainder of the Cβ sequence at that end of the fragment is also included in the vector. Nucleotide sequences encoding the peptides shown in the upper part of the table were inserted into either the vector pTOPE or the vector pET17b. Both of these vectors allow expression of inserted fragments from the T7 promoter, and both produce fusion proteins containing a fragment of the ϕ10 capsid protein N terminal to the amino acid sequence encoded by the insert. However, while pET17b encodes only 8 amino acids of the ϕ10 protein, pTOPE encodes a 288 amino acid fragment of the ϕ10 protein.

As shown in Table 1 (SEQ ID NOS: 11–24), certain fragments of Cβ produced from pET17b exhibit reduced IgA-binding, while the same fragment produced by pTOPE is capable of binding IgA. The fragments tested lack the region of Cβ predicted to be involved in dimerization, but do not contain any mutations in the putative IgA binding domain (note that the Cβ fragments inserted into vector pET24b, shown at the bottom of Table 1, contain the putative dimerization region but nonetheless exhibit reduced IgA binding due to mutations in the IgA binding domain, as described above). It is postulated that these Cβ fragments bind DNA when produced from pTOPE because the 288 amino acid fragment of the ϕ10 protein allows dimerization of the Cβ fragment. This may be due to the fact that the ϕ10 capsid protein normally forms oligomers; the region responsible for oligomerization may thus allow dimerization of the inserted Cβ fragments, and thus IgA-binding. Thus, the invention also relates to a mutant Cβ protein having a mutation in the dimerization domain of Cβ, wherein the mutant Cβ protein is incapable of binding IgA. Of course, in the interest of producing a non-IgA binding Cβ protein retaining as much of the antigenicity of the wild type Cβ protein as possible, dimerization of Cβ should not be interrupted.

It has also been discovered that production of Cβ protein from *E. coli* can be problematic because the protein is cleaved at a specific region, presumably by an *E. coli* signal peptidase. This cleavage results in a truncated protein, which obviously is not ideal for a vaccine, as it lacks many antigenic epitopes of the wildtype Cβ protein. The cleavage site has been predicted by sequence analysis and by matrix assisted laser desorption initiated time of flight (MALDI-TOF) mass spectrometry (von Heijne, *Nucleic Acids Res.* 14: 4683–4690 (1986)). The cleavage site is between amino acid residues 538 and 539 (after alanine and before glutamine) of the amino acid sequence shown in FIG. 1 (SEQ ID NO:2). The signal peptidase recognition site is located within a 20 amino acid stretch located between residues 521 and 541 of the amino acid sequence shown in FIG. 1 (SEQ ID NO:2). Therefore, by deleting this region, the Cβ protein or a non-IgA binding mutant thereof can successfully be produced in *E coli.* Furthermore, as signal peptidases have very strict sequence specificity, alteration of the signal peptidase recognition sequence, including even a single, conservative amino acid substitution in this region, may eliminate cleavage of Cβ by *E. coli.* The recognition sequence required for cleavage by this signal peptidase is believed to be GluLeuIleLysSerAlaGlnGlnGlu (SEQ ID NO:25), corresponding to amino acid residues 533–541 of the sequence shown in FIG. 1 (SEQ ID NO:2). Alteration of either the serine or the alanine residue of this sequence by either deletion or non-conservative substitution is expected to eliminate cleavage by the signal peptidase. Of course, ideally, the mutagenesis of Cβ will be kept to a minimum so as to retain the tertiary structure of the wildtype antigen for the purposes of eliciting an immunogenic response.

Thus, the invention also relates to a mutant Cβ protein of the group B streptococcal (GBS) beta antigen, wherein IgA binding by the Cβ protein is reduced or eliminated by any of the mutations described above, and wherein at least one of amino acid residues 521–541 of the amino acid sequence shown in FIG. 1 (SEQ ID NO:2) is either (a) deleted or (b) altered, so that the protein is not cleaved in this region when Cβ is produced in *E. coli.* In a preferred embodiment, at least one of amino acid residues 533–541 of the sequence shown in FIG. 1 (SEQ ID NO:2) is either (a) deleted or (b) altered. In a more preferred embodiment, at least one of amino acid residues 537 and 538 is either (a) deleted or (b) altered. Of course, one of ordinary skill will be able to determine other suitable amino acid substitutions by routine experimentation, and by reference to the article by von Heijne (*Nucleic Acids Res.* 14: 4683–4690 (1986)).

The invention also relates to polynucleotide molecules encoding the mutant proteins of the invention, vectors comprising those polynucleotide molecules, and host cells transformed therewith.

The invention also relates to the expression of novel mutant Cβ polypeptides, wherein IgA binding by the Cβ protein is reduced or eliminated, in a cellular host.

Prokaryotic hosts that may be used for cloning and expressing the polypeptides of the invention are well known in the art. Vectors which replicate in such host cells are also well known.

Preferred prokaryotic hosts include, but are not limited to, bacteria of the genus Escherichia, Bacillus, Streptomyces, Pseudomonas, Salmonella, Serratia, Xanthomonas, etc. Two such prokaryotic hosts are *E. coli* DH10B and DH5αF'IQ (available from LTI, Gaithersburg, Md.). The most preferred host for cloning and expressing the polypeptides of the invention is *E. coli* BL21 (Novagen, Wis.), which is lysogenic for DE3 phage.

The present invention also relates to vectors which include the isolated DNA molecules of the present invention, host cells which are genetically engineered with the recombinant vectors, and the production of the polypeptides of the invention by recombinant techniques.

Host cells can be genetically engineered to incorporate nucleic acid molecules and express polypeptides of the present invention. For instance, recombinant constructs may be introduced into host cells using well known techniques of infection, transduction, transfection, and transformation. The polynucleotides may be introduced alone or with other polynucleotides. Such other polynucleotides may be introduced independently, co-introduced or introduced joined to the polynucleotides of the invention.

Thus, for instance, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. cited above, which is illustrative of the many laboratory manuals that detail these techniques.

In accordance with this aspect of the invention the vector may be, for example, a plasmid vector, a single or double-stranded phage vector, a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsulated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate transacting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art (see U.S. Pat. No. 5,464,758).

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain or propagate, polynucleotides, or to express a polypeptide, in a host may be used for expression in this regard.

The appropriate DNA molecule may be inserted into the vector by any of a variety of well-known and routine techniques. In general, a DNA molecule for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill in the art. Suitable procedures in this regard, and for constructing expression vectors using alternative techniques, which also are well known and routine to those skill, are set forth in great detail in Sambrook et al. cited above.

The DNA molecule inserted in the expression vector is operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. It will be understood that numerous promoters not mentioned are suitable for use in this aspect of the invention are well known and readily may be employed by those of skill in the art in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing *E. coli* and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as *E. coli,* Streptomyces and *Salmonella typhimurium* cells. Hosts for a great variety of expression constructs are well known, and those of skill will be enabled by the present disclosure readily to select a host for expressing a polypeptides in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

As the invention concerns the construction of a protein having a reduced or eliminated ability to bind human IgA, the invention thus relates to using in vitro mutagenesis methods to generate the mutant Cβ proteins of the invention. A number of in vitro mutagenesis methods are well known to those of skill in the art; several are provided here as examples.

One such method introduces deletions or insertions into a polynucleotide molecule inserted into a plasmid by either partially or completely digesting the plasmid with an appropriate restriction enzyme, and then ligating the ends to again generate a plasmid. Very short deletions can be made by first cutting a plasmid at a restriction site, and then subjecting the linear DNA to controlled nuclease digestion to remove small groups of bases at each end. Precise insertions may also be made by ligating double stranded oligonucleotide linkers to a plasmid cut at a single restriction site.

Chemical methods can also be used to introduce mutations to a single stranded polynucleotide molecule. For example, single base pair changes at cytosine residues can be created using chemicals such as bisulfite, which deaminates cytosine to uracil, thus converting GC base pairs to AT base pairs.

Preferably, oligonucleotide directed mutagenesis will be used so that all possible classes of base pair changes at any determined site along a DNA molecule can be made. In general, this technique involves annealing a oligonucleotide complementary (except for one or more mismatches) to a single stranded nucleotide sequence of interest. The mismatched oligonucleotide is then extended by DNA polymerase, generating a double stranded DNA molecule which contains the desired change in sequence on one strand. The changes in sequence can of course result in the deletion, substitution, or insertion of an amino acid if the change is made in the coding region of a gene. The double stranded polynucleotide can then be inserted into an appropriate expression vector, and a mutant polypeptide can thus be produced. The above-described oligonucleotide directed mutagenesis can of course be carried out via PCR. An example of such a system is the Ex-Site™ PCR site-directed mutagenesis technique (Stratagene, Calif.) used in Example 4.

Using the Ex-Site™ PCR site-directed mutagenesis technique, several different oligonucleotides were made to induce different changes in the DNA sequence in the region of interest. In one particular example, overlapping primers were obtained, wherein both primers contained the sequence required to change lysine to alanine at amino acids 170 and 175 in the sequence shown in FIG. 1 (SEQ ID NO: 2) (see FIG. 2 and Table 1). The forward primer, designated Cβ 613, had the sequence (SEQ ID NO:.26) 5'-GTT GAA GCA ATG GCA GAG CAA GCG GGA ATC ACA AAT GAA G-3' and the reverse primer, designated Cβ 642R had the sequence (SEQ ID NO:27) 5'-GAT TCC CGC TTG CTC TGC CAT TGC TTC AAC TTG ACT TTT TTG-3' (the substitutions are noted in BOLD). These oligonucleotides were combined with pNV222 template, which consists of the Cβ gene inserted into the pSP76 vector. PCR was performed, and the products were ligated and introduced into *E. coli* strain DH5α, thus generating clones containing the mutant Cβ gene.

The following vectors, which are commercially available, may be used in the practice of the invention. Among vectors preferred for use in bacteria are pQE70, pQE60 and pQE-9, available from Qiagen; pBS vectors, Phagescript vectors, Bluescript® vectors, pNH8A, pNH16a, pNH18A, and pNH46A, available from Stratagene; ptrc99a, pKK223-3, pKK233-3, pDR540, and pRIT5 available from Pharmacia; pUC18, pUC19 and pPROEX-1, available from LTI, and pTOPE, pET17b, and pET24a (Novagen Inc., Madison, Wis.). These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of restriction site or sites for introducing a candidate promoter fragment; i.e., a fragment that may contain a promoter. As is well known, introduction into the vector of a promoter-containing fragment at the restriction site upstream of the CAT gene engenders production of CAT activity, which can be detected by standard CAT assays. Vectors suitable to this end are well known and readily available. Two such vectors are pKK232-8 and pCM7. Thus, promoters for expression of polynucleotides of the present invention include not only well known and readily available promoters, but also promoters that readily may be obtained by the foregoing technique, using a reporter gene.

Among known bacterial promoters suitable for expression of polynucleotides and polypeptides in accordance with the present invention are the *E. coli* lacI and lacZ and promoters, the T3 and T7 promoters, the gpt promoter, the lambda PR, PL promoters and the trp promoter.

Selection of appropriate vectors and promoters for expression in a host cell is a well known procedure and the requisite techniques for expression vector construction, introduction of the vector into the host and expression in the host are routine skills in the art.

The present invention also relates to host cells containing the constructs discussed above. The host cell can be a prokaryotic cell, such as a bacterial cell.

Constructs in host cells can be used in a conventional manner to produce the gene product encoded by the recombinant sequence. Alternatively, the polypeptides of the invention can be synthetically produced by conventional peptide synthesizers.

Following transformation of a suitable host strain and growth of the host strain to an appropriate cell density, where the selected promoter is inducible, it is induced by appropriate means (e.g., temperature shift or exposure to chemical inducer) and cells are cultured for an additional period.

Cells typically are then harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents; such methods are well know to those skilled in the art.

The invention also relates to a vaccine comprising a mutant Cβ protein, wherein IgA binding by the Cβ protein is reduced or eliminated as described herein, together with a pharmaceutically acceptable carrier. In a preferred embodiment, the protein is conjugated to a polysaccharide.

The conjugates of the invention may be formed by reacting the reducing end groups of the polysaccharide to primary amino groups (that is, lysine residues) of the Cβ protein by reductive amination. The polysaccharide may be conjugated to any or all of the primary amino groups of the protein. The reducing groups may be formed by selective hydrolysis or specific oxidative cleavage, or a combination of both. Preferably, the Cβ protein is conjugated to the polysaccharide by the method of Jennings et al., U.S. Pat. No. 4,356,170, which involves controlled oxidation of the polysaccharide with periodate followed by reductive amination with the Cβ protein of the invention.

In a preferred embodiment, the polysaccharide is one of the Group B streptococcal capsular polysaccharides selected from types Ia, II, III and V. See Baker, C. J. and D. L. Kasper, *Rev. Inf. Dis.* 7:458–467 (1985); Baker, C. J., et al., *N. Engl. J. Med.* 319:1180–1185 (1988); Baker, C. J., et al., *New Engl. J. Med.* 322:1857–1860 (1990). The vaccine may also be a combination vaccine comprising one or more of the Cβ protein-polysaccharide conjugates selected from the group consisting of Cβ conjugated to Group B capsular polysaccharide type Ia (Cβ-Ia); Cβ conjugated to Group B capsular polysaccharide type II (Cβ-II); Cβ conjugated to Group B capsular polysaccharide type III (Cβ-III); and Cβ conjugated to Group B capsular polysaccharide type V (Cβ-V). Most preferably, the vaccine is a combination vaccine comprising Cβ-Ia, Cβ-II, Cβ-III and Cβ-V. Such a combination vaccine will elicit antibodies to Group B streptococci of Types Ia, II, III, V, and Ib (as Type Ib Group B streptococci also express Cβ). Furthermore, the immune response to the polysaccharides of the combination vaccine will be a T dependent response.

The vaccine of the present invention comprises one or more of the Cβ protein vaccines or conjugate vaccines in amounts effective depending on the route of administration. Although subcutaneous or intramuscular routes of administration are preferred, the vaccine of the present invention can also be administered by an intraperitoneal or intravenous route. One skilled in the art will appreciate that the amounts to be administered for any particular treatment protocol can be readily determined without undue experimentation. With respect to each conjugate, suitable amounts are expected to fall within the range of 2 micrograms of the protein per kg body weight to 100 micrograms per kg body weight. In a preferred embodiment, the vaccine comprises about 2 μg of the Cβ protein or an equivalent amount of the protein-polysaccharide conjugate. In another preferred embodiment, the vaccine comprises about 5 μg of the Cβ protein or an equivalent amount of the protein-polysaccharide conjugate.

The vaccine of the present invention may be employed in such forms as capsules, liquid solutions, suspensions or elixirs for oral administration, or sterile liquid forms such as solutions or suspensions. Any inert carrier is preferably used, such as saline, phosphate-buffered saline, or any such carrier in which the non-IgA Fc binding group B streptococcal Cβ protein or conjugate vaccine have suitable solubility properties. The vaccines may be in the form of single dose preparations or in multi-dose flasks which can be used for mass vaccination programs. Reference is made to Remington's *Pharmaceutical Sciences,* Mack Publishing Co., Easton, Pa., Osol (ed.) (1980); and *New Trends and Developments in Vaccines,* Voller et al. (eds.), University Park Press, Baltimore, Md. (1978), for methods of preparing and using vaccines.

The vaccines of the present invention may further comprise adjuvants which enhance production of Cβ-specific antibodies. Such adjuvants include, but are not limited to, various oil formulations such as Freund's complete adjuvant (CFA), stearyl tyrosine (ST, see U.S. Pat. No. 4,258,029), the dipeptide known as MDP, saponin (see U.S. Pat. No. 5,057,540), aluminum hydroxide, and lymphatic cytokine.

Freund's adjuvant is an emulsion of mineral oil and water which is mixed with the immunogenic substance. Although Freund's adjuvant is powerful, it is usually not administered to humans. Instead, the adjuvant alum (aluminum hydroxide) or ST may be used for administration to a human. The Cβ protein vaccine or a conjugate vaccine thereof may be absorbed onto the aluminum hydroxide from which it is slowly released after injection. The vaccine may also be encapsulated within liposomes according to Fullerton, U.S. Pat. No. 4,235,877.

In another preferred embodiment, the present invention relates to a method of inducing an immune response in an animal comprising administering to the animal the vaccine of the invention, produced according to methods described, in an amount effective to induce an immune response.

Having now generally described the invention, the same will be more readily understood through reference to the following Examples which are provided by way of illustration, and are not intended to be limiting of the present invention, unless specified.

EXAMPLES

Example 1

Cloning and Expression of the Gene Encoding Cβ

To locate the IgA binding site on the Cβ protein, two oligonucleotides were synthesized. The first oligonucleotide, oligo 1, corresponds to the 5' end of the mature protein, and has the sequence (SEQ ID NO: 28) 5'-AAGGATCCAAGTGAGCTTGTAAAGGACGAT-3', which includes a BamHI site. The second oligonucleotide falls just short of the 3' end of the gene, and has the sequence (SEQ ID NO:29) 5'-AAAACTCGAGTTTCTTTTCCGTTGTTGATGTA-3', and includes a XhoI site. The oligonucleotide for the 3' end of the gene was chosen to eliminate the LPXTG motif found in most gram positive cell wall proteins. This sequence motif has been shown to be involved in the processing of these cell wall proteins and is the part of these proteins which eventually becomes covalently bound to peptidoglycan (Navarre, W. W. and O. Schneewind, *Molec. Microbiol.* 14:115–121 (1994); Schneewind, O., et al., *Science* 268:103–106 (1995)). Using chromosomal DNA from Strain A909 Group B streptococci containing the gene for the Cβ protein as a template, and standard PCR procedures, a product of approximately 3.2 kb was produced as observed when electrophoresed on a 1% agarose gel. The PCR product containing the Cβ protein gene was cleaved with the endonuclease restriction enzymes BamHI and XhoI. This BamHI-XhoI DNA fragment contained the sequence for the entire Cβ protein except for the last 33 amino acids at the carboxyl terminus, including the putative IgA binding site. The DNA fragment was then ligated into the appropriately restricted T7 expression plasmid pET17b (Novagen Inc., Madison, Wis.) using a standard T4 ligase procedure. The plasmid was then transformed into the *E. coli* strain BL21 (DE3) using the manufacturer's suggested protocols (Novagen Inc.). *E. coli* cells containing the plasmid were selected on LB plates containing 50 μg/ml carbenicillin. These plates were incubated overnight at 37° C. The transformant colonies were carefully lifted onto nitrocellulose filters saturated with IPTG. After 30 min, the bacteria were lysed by placing the filters into a chloroform vapor chamber for 15 min at room temperature.

After the filters were removed from the chamber, they were placed, colony-side up, onto a Whatman® 3 MM filter which had been previously saturated with 20 mM Tris®-HCl, pH 7.9, 6 M urea, and 0.5 M NaCl. After 15 min, the filters were washed three times in PBS and incubated for 1 hr with purified human IgA in PBS-Tween®. The filters were then rewashed in the PBS-Tween® and developed by standard procedures (Blake, M. S., et al., *Analyt. Biochem.*

136:175–17 (1984)) using a goat antihuman IgA-alkaline phosphatase conjugate (Cappel Research Products, West Chester, Pa.). Several colonies demonstrating high IgA binding activity were selected and grown overnight in 1 ml LB broth containing carbenicillin at 30° C. These cultures were then diluted 1 to 100 with fresh LB-carbenicillin broth and incubated at 30° C. for an addition 6 hr. Expression was then induced by the addition of IPTG and the culture continued for an addition 2 hr at 30° C. The cells were collected by centrifugation, resuspended in water and subjected to several freeze-thaw cycles. The cells were once again collected by centrifugation and the supernatants saved for examination of their IgA binding activity.

Example 2

Identification of the IgA Binding Domain of Cβ

Once certain a stable plasmid producing a recombinant Cβ protein had been achieved and that the expressed protein bound human IgA, a strategy similar to that of the Novatope® System (Novagen, Inc.) was utilized to locate the IgA binding region of Cβ. This procedure was performed according to the manufacturer's instructions. Briefly, the purified plasmid containing the Cβ gene was randomly digested with DNase I and electrophoresed in a 2% low melting point agarose gel. Fragments of the DNA corresponding to sizes between 100 to 300 base pairs were excised from the gel, purified, and resuspended in TE buffer. A single dA was added to the fragments using the recommended reaction mixture and the fragments ligated into the pETOPET vector which contained single dT ends. After the standard ligation procedure, the plasmids were transformed into competent NovaBlue (DE3) cells (Novagen, Inc.) and plated on LB plates containing 50 μg/ml carbenicillin. These plates were incubated overnight at 37° C. The transformant colonies were tested for IgA binding activity as described in Example 1. Several clones were selected on the bases of their binding to the IgA. The bacteria from each of these clones were inoculated separately onto fresh LB plates and retested for their IgA binding ability as before. Plasmid preparations were made from each by standard means and sequenced.

The nucleotide sequences of the cloned Cβ protein gene fragments were determined by the dideoxy method using denatured double-stranded plasmid DNA template as described (Current Protocols in Molecular Biology, John Wiley & Sons, New York, N.Y. (1993)). Sequenase® II kits (United States Biochemical Corp., Cleveland, Ohio) were used in accordance with the manufacturer's instructions. The smallest fragment of DNA obtained that included part of the Cβ gene is shown in FIG. 1. The translation of this sequence corresponds to amino acid 101 to 230 of the mature Cβ protein shown in FIG. 1 (SEQ ID NO: 2). Attempts to further shorten this DNA fragment failed to give any IgA binding activity.

Example 3

ELISA Inhibition Assays: Peptide Binding Studies

Several synthetic peptides were made corresponding to the amino acid sequence contained within this region of the Cβ protein. Peptides were synthesized using NMP t-butoxycarbonyl chemistry on an ABI 430A peptide synthesizer (Applied Biosystems, Foster City, Calif.) and were deprotected. Peptides from a sample of the resin were removed from the resin by treatment with HF in the presence of anisole (0° C./1 h). Preparative purification of these peptides were performed using a C18 column (2.14 ID×30 cm)(Dynamax-Rainin, Woburn, Mass.). The peptides were quantitated by PTC amino acid analysis using Waters Pico-tag system (Waters, Milford, Mass.). The synthesized peptides eluted from the C18 column as a major peak consisting of usually 75–85% of the total elution profile. The amino acid composition of the purified peptides were in good agreement with the sequence which was used to synthesize the peptides. These peptides were used in ELISA inhibition assays to block the binding of human IgA to the purified Cβ protein as follows. Microtiter plates (Nunc-Immuno Plate IIF, Vangard International, Neptune, N.J.) were sensitized by adding 0.1 ml per well of purified Cβ at a concentration of 2.0 μg/ml in 0.1 M carbonate buffer, pH 9.6 with 0.02% azide. The plates were incubated overnight at room temperature. The plates were washed five times with 0.9% NaCl, 0.05% Brij® 35, 10 mM sodium acetate pH 7.0, 0.02% azide. A purified human IgA myeloma protein was purchased from Cappel Laboratories, was diluted in PBS with 0.5% Brij® 35 and added to the plate and incubated for 1 hr at room temperature. The plates were again washed as before and the secondary antibody, alkaline phosphatase conjugated goat anti-human IgA (Tago Inc., Burlingame, Calif.), was diluted in PBS-Brij®, added to the plates and incubated for 1 h at room temperature. The plates were washed as before and p-nitrophenyl phosphate (Sigma 104® phosphatase substrate) (1 mg/ml) in 0.1 M diethanolamine, 1 mM $MgCl_2$, 0.1 mM $ZnCl_2$, 0.02% azide, pH 9.8 added. The plates were incubated at 37° C. for 1 h and the absorbance at 405 nm determined using an Elida-5 microtiter plate reader (Physica, New York, N.Y.). Control wells lacked either the primary and/or secondary antibody. This was done to obtain a titer of the human IgA myeloma protein which would give a half-maximal reading in the ELISA assay. This titer would be used in the inhibition ELISA. The microtiter plate were sensitize and washed as before. Purified synthetic peptides were added and diluted in PBS-Brij®. The dilution of the human IgA myeloma protein which gave the half maximal reading was then added. The mixture was then incubated for 1 hr at room temperature. The plates were rewashed and the conjugated second antibody added as stated. The plates were then processed and read as described. The percentage of inhibition would be calculated as follows:

1-(ELISA value with the peptide added)/(ELISA value without the peptide added).

The peptide which inhibited in this ELISA assay contained the sequence Asn-His-Gln-Lys-Ser-Gln-Val-Glu-Lys-Met-Ala-Glu-Gln-Lys-Gly (SEQ ID NO:30). This suggested that at least part of the IgA binding domain of the Cβ was comprised within the region of the protein containing this sequence.

Example 4

Oligonucleotide Directed Mutagenesis of the Gene Encoding Cβ

In order to confirm the importance of this region in the Cβ protein for IgA binding activity and to begin to generate the mutant proteins that in the end would be used in the vaccine formulation, a modification of the Ex-Site™ PCR site-directed mutagenesis protocol was employed as developed by Stratagene (Stratagene, Calif.). The template used was a plasmid called pNV222 which consisted of the Cβ gene inserted into the pSP76 vector (Promega,Madison). DNA oligonucleotides were synthesized on an Applied Biosystems model 292 DNA Synthesizer (Foster City, Calif.). The oligonucleotides were manually cleaved from the column by treatment with 1.5 ml of ammonium hydroxide for 2 hours with gentle mixing every 15 minutes. They were deprotected at 55° C. for 16–18 hours. After deprotection they were dried down and used directly or purified using oligonucleotide purification columns (Applied Biosystems, Foster City Calif.). Several different oligonucleotides were made to induce different changes in the DNA sequence in the region of interest. An example of which is the following. The primers, in this particular example, were overlapping primers, both containing the sequence required to change lysine to alanine at amino acids 170 and 175 in the sequence shown in FIG. 1 (SEQ ID NO: 2) The forward primer, designated Cβ 613, had the sequence (SEQ ID NO: 26) 5'-GTT GAA GCA ATG GCA GAG CAA GCG GGA ATC ACA AAT GAA G-3' and the reverse primer, designated Cβ 642R had the sequence (SEQ ID NO: 27) 5'-GAT TCC CGC TTG CTC TGC CAT TGC TTC AAC TTG ACT TTT TTG-3' (the substitutions are noted in BOLD). The reaction conditions were as follows: 10 ng pNV222 template, 15 pmol. of each primer, 1 mM of each dNTP, 1X Vent® Polymerase Buffer (20 mM Tris®-HCl, pH 7.5; 10 mM KCl; 10 mM $(NH_4)_2$ $SO_4$; 2 mM $MgSO_4$ 0.1% (v/v) Triton® X-100; 0.1 mg/ml bovine serum albumin (BSA)), 10 units of Vent® Polymerase, and $H_2O$ to 100 μl. The reactions were prepared with PCR Gem 10 wax beads as per the Hot Start Protocol (Perkin Elmer, Foster City, Calif.). The reactions were run in a Perkin Elmer® Thermocycler (Perkin Elmer, Foster City, Calif.) under the following conditions: 1 cycle of 94° C. for 5 minutes; 10 cycles of 94° C. for 30 seconds, 37° C. for 2 minutes, 72° C. for 10 minutes; 30 cycles of 94° C. for 30 seconds, 55° C. for 2 minutes, 72° C. for 10 minutes; and 1 cycle of 72° C. for 12 minutes. The reaction was treated with 10 units of DpnI at 37° C. for 30 minutes to destroy the template DNA, followed by a 60 minute treatment at 72° C. with PfuI polymerase to fill in any remaining overhangs. The reaction was diluted 1:4.6 in 1 X Vent® Buffer plus 0.38 mM dATP. The diluted reaction was ligated for 24 hours at 25° C. and transformed into competent DH5α cells (Gibco/BRL, Gaithersburg, Md.). Selected colonies were grown in 3 ml of LB plus kanamycin (50 mg/ml) at 37° C. for 16–18 hours. DNA was prepared using QIAspin™ columns (Qiagen, Chatsworth, Calif.). The clones were analyzed for insert size on 0.8% agarose gels and then sequenced. Selected clones were then grown in 100 ml LB plus kanamycin (50 mg/ml) at 37° C. for 16–18 hours. DNA was prepared using the Qiagen®-tip 100 (Qiagen, Chatsworth, Calif.). They were then digested with NdeI and PstI and run on 0.8% agarose gels to separate the mutated region. The 2300 bp fragment was isolated and purified from the gel using the Gene-Clean Spin Kit™ (Bio 101, Vista, Calif.). A clone named pNV34 which consisted of the expression vector pET 24a (Novagen Inc.) and the native Cβ gene, was also digested with NdeI and PstI and run on a 0.8% agarose gel. The large band (6300 bp) containing the pET vector and the remainder of the Cβ gene was isolated and purified from the gel using the Gene-Clean Spin Kit™ (Bio 101). These two fragments were ligated at 4° C. for 24 hours and transformed into competant BL21 (DE3) cells. Selected colonies were grown in 3 ml of LB plus kanamycin (50 mg/ml) at 37° C. for 16–18 hours. DNA was prepared using QIAspin™ columns (Qiagen) and the clones were analyzed for insert size on 0.8% agarose gels.

Figure 3:
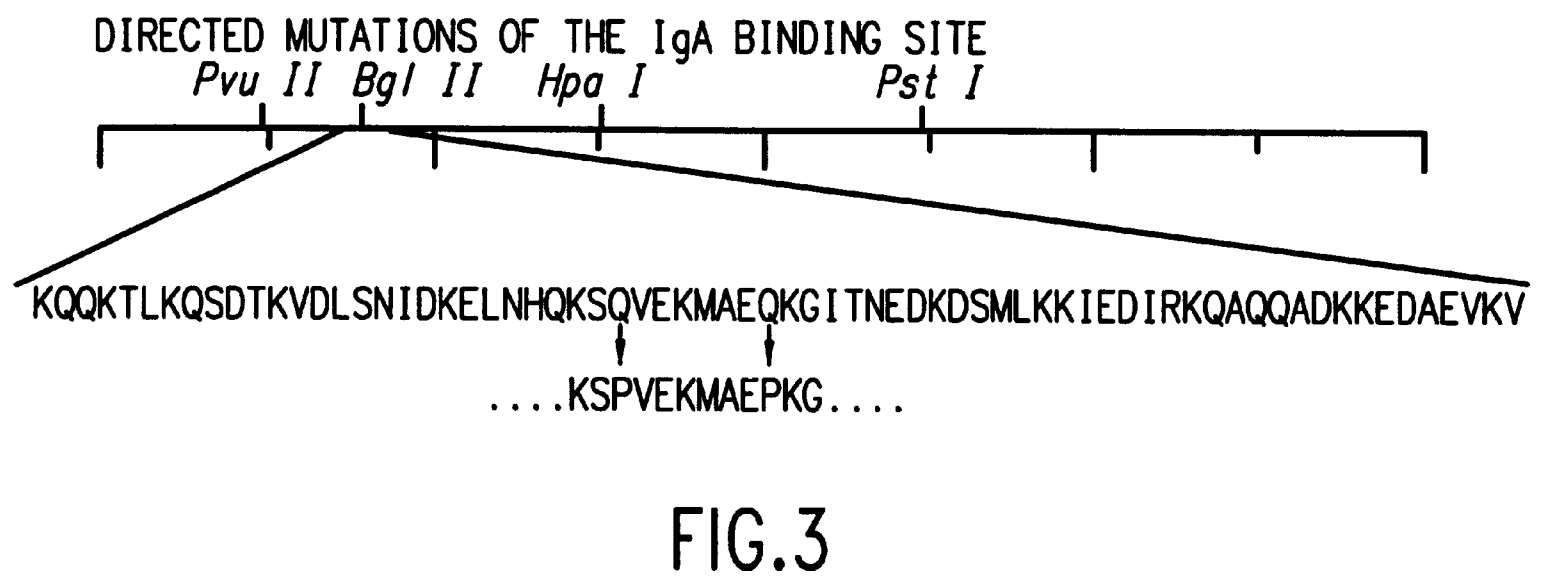
Figure 4:
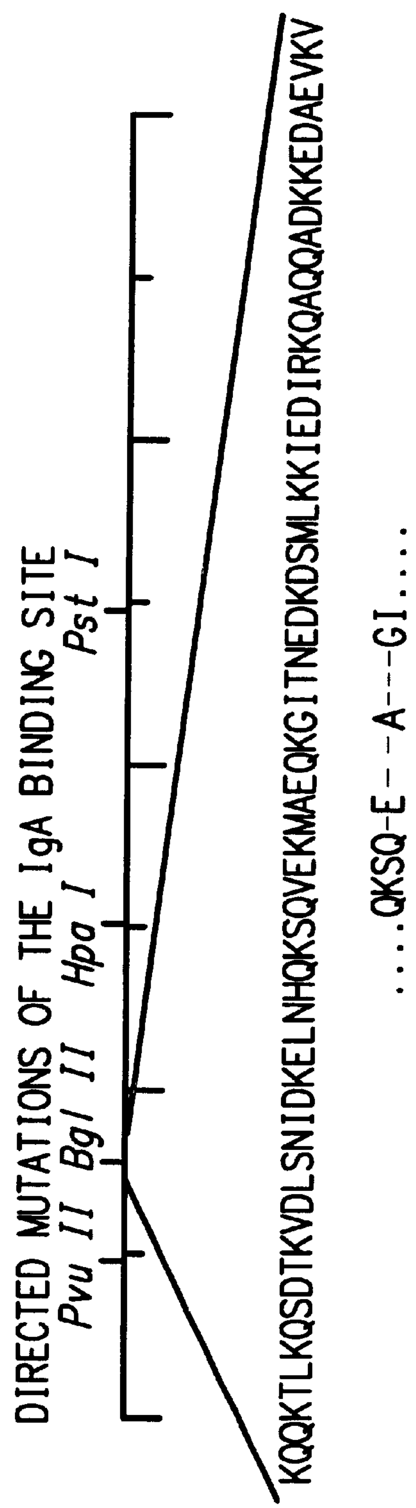
FIG. 4 is a map of the region of the Cβ gene which encodes the IgA binding site of the Cβ protein; 6 amino acids have been deleted from this region in the mutant protein, generating mutant dgb1 (SEQ ID NO: 23)(see Table 1).

Also constructed were clones encoding mutant Cβ proteins wherein two glutaminyl residues are replaced by prolinyl residues (FIG. 3 and SEQ ID NO:6), and wherein a deletion in the Cβ gene had occurred resulting in a 6 amino acid deletion in the region of interest (FIG. 4 and SEQ ID NO:8).

Clones expressing a Cβ protein which lacked or had reduced IgA binding activity but still reacted with the anti-βag antiserum were selected (see Example 5) and grown in 100 ml LB plus kanamycin (50 mg/ml) at 37° C. for 16–18 hours. Plasmid DNA from these clones was prepared using Qiagen® tip 100 (Qiagen) and the mutated Cβ gene entirely sequenced.

Example 5

Western Blot and ELISA Analysis of IgA Binding by Cβ Mutants

The proteins encoded by the mutated genes were expressed and subjected to SDS-PAGE and western blot analysis in order to determine if mutations in the gene encoding the Cβ protein reduced or eliminated IgA binding, while retaining Cβ antigenicity. Two western blots were made for each sample and reacted with either the purified human IgA myeloma protein or hyperimmune rabbit anti-βag protein antiserum. The clone expressing a Cβ protein wherein lysine is changed to alanine at amino acids 170 and 175 in the sequence shown in FIG. 1 (SEQ ID NO:2) demonstrated almost no IgA binding activity, but the ability of the protein to react with anti-Cβ antiserum remained high. IgA binding activity was also substantially eliminated in the clone expressing a Cβ protein wherein two glutaminyl residues are replaced by prolinyl residues (FIG. 3 and SEQ ID NO:6) and in the clone encoding a Cβ protein having a six amino acid deletion (FIG. 4 and SEQ ID NO:8), while reactivity with the anti-Cβ antiserum was maintained for both. The data for the clone having a six amino acid deletion suggested that the residues responsible for the IgA binding activity of the Cβ protein were located within this region of the protein, and that other possible mutations within this area would effect the IgA binding activity.

A competitive inhibition ELISA was used to more precisely determine the amount of antigenic and/or structure change the sequence modifications had on the Cβ protein. Microtiter plates (Nunc-Immuno Plate IIF, Vangard International, Neptune, N.J.) were sensitized by adding 0.1 ml per well of purified Cβ at a concentration of 2.0 μg/ml in 0.1M carbonate buffer, pH 9.6 with 0.02% azide. The plates were incubated overnight at room temperature. The plates were washed five times with 0.9% NaCl, 0.05% Brij® 35, 10 mM sodium acetate pH 7.0, 0.02% azide. Hyperimmune rabbit antiserum to the Cβ protein was diluted in PBS with 0.5% Brij® 35 and added to the plate and incubated for 1 hr at room temperature. The plates were again washed as before and the secondary antibody, alkaline phosphatase conjugated goat anti-rabbit IgG (Tago Inc., Burlingame, Calif.), was diluted in PBS-Brij®, added to the plates and incubated for 1 h at room temperature. The plates were washed as before and p-nitrophenyl phosphate (Sigma 104® Phosphatase Substrate 104) (1 mg/ml) in 0.1M diethanolamine, 1 mM $MgCl_2$, 0.1 mM $ZnCl_2$, 0.02% azide, pH 9.8, was added. The plates were incubated at 37° C. for 1 h and the absorbance at 405 nm determined using an Elida-5 microtiter plate reader (Physica, New York, N.Y.). Control wells lacked either the primary and/or secondary antibody. This was done to obtain a titer of the rabbit anti-Cβ protein which would give a half-maximal reading in the ELISA assay. This titer would be used in the inhibition ELISA. The microtiter plate were sensitized and washed as before. Purified Cβ protein or mutations of the Cβ protein were added and diluted in PBS-Brij®. The dilution of the rabbit anti-Cβ protein which gave the half maximal reading was then added. The mixture was then incubated for 1 hr at room temperature. The plates were rewashed and the conjugated second antibody added as stated. The plates were then processed and read as described. The percentage of inhibition would be calculated as follows:

1-(ELISA value with the protein added)/(ELISA value without the proteins added).

Figure 5:
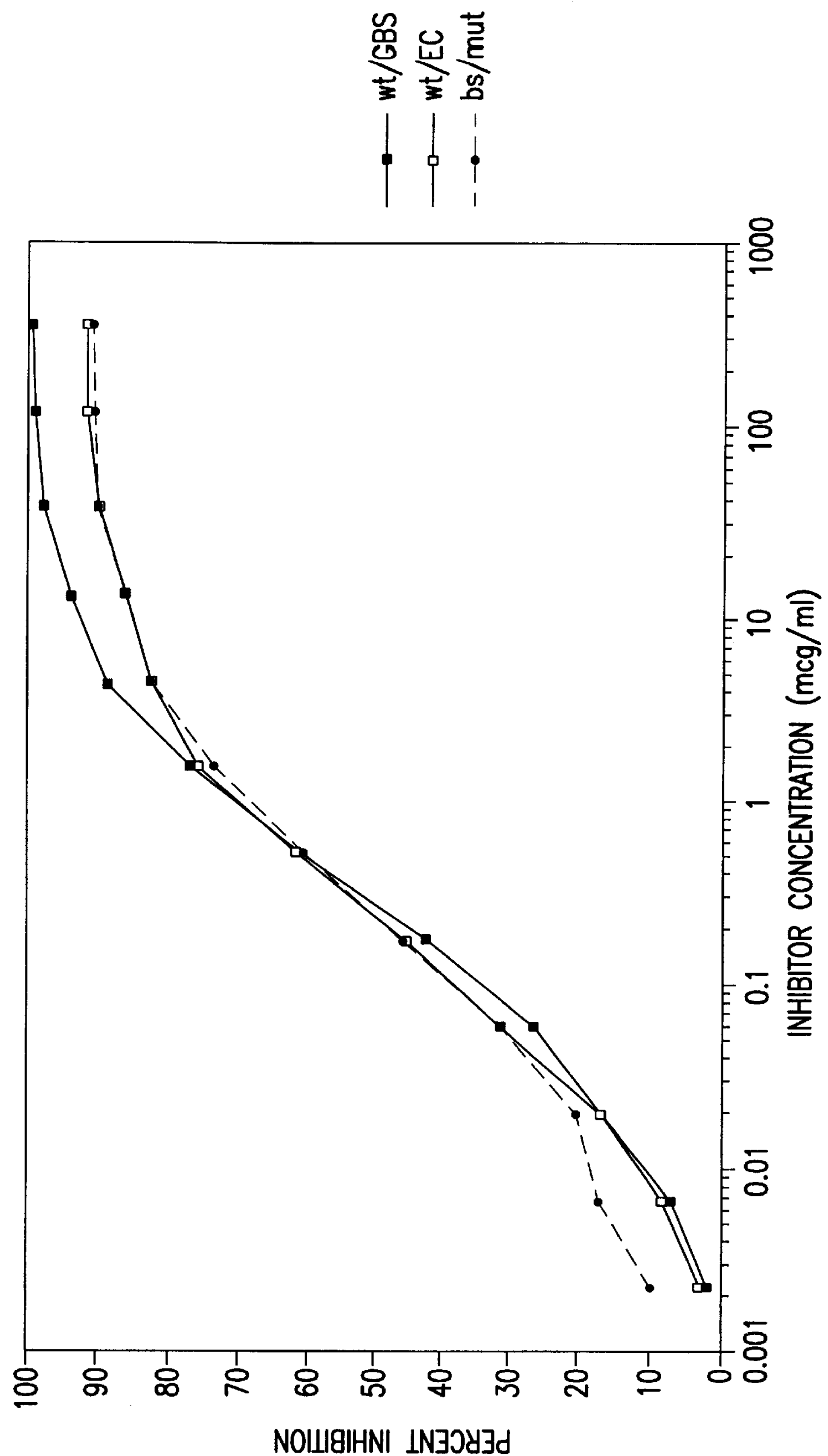
FIG. 5 is a graph showing the competitive inhibition of ELISA reactivity by Cβ proteins.

FIG. 5, shows the results of one of these inhibition ELISA assays. In this assay the inhibition of the wildtype Cβ protein from streptococci is compared with the recombinant Cβ protein and the glutaminyl to prolinyl mutants, both expressed in *E. coli*. As can be seen from the figure, this assay is sensitive enough to detect the absence of the membrane spanning region in the recombinants of the Cβ proteins. However, when the recombinant Cβ protein containing the wildtype sequence is compared to the substitution mutant lacking IgA binding activity, the antigenic differences are minimal. This would suggest that such substitution mutants maintain most of the antigenic character of the Cβ protein but lack the unwanted IgA binding activity.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following Claims. All patents and publications cited herein are incorporated by reference herein in their entirety.

| Name | Sequence | Vector | % wild-type |
|---|---|---|---|
| IgAbs+ | ]LLHIKQHEEVEKDKKAKQQKTLKQSDTKVDLSNIDKELNHQKSQVEKMAEQKGITNEDKDSMLKKIEDIRKQAQQADKKEDAEVKVREELGKLFS-<br>STKAGLDQEIQ[ | pTOPE | 100 |
| dgb6 | ]DSDALLELENQFNETNRLLHIKQHEEVEKDKKAKQQKTLKQSDTKVDLSNIDKELNHQKSQVEKMAEQKGITNEDKDSMLKKIEDIRKQAQQADKKEDAEVKVREELGKLFS-<br>STKAGLDQEIQEHVKKETSSEENTQKVDEHYANSL[ | 17b | 20 |
| dgb6p | ]DSDALLELENQFNETNRLLHIKQHEEVEKDKKAKQQKTLKQSDTKVDLSNIDKELNHQKSQVEKMAEQKGITNEDKDSMLKKIEDIRKQAQQADKKEDAEVKVREELGKLFS-<br>STKAGLDQEIQEHVKKETSSEENTQKVDEHYANSL[ | pTOPE | 100 |
| dgb7 | ]VDLSNIDKELNHQKSQVEKMAEQKGITNEDKDSMLKKIEDIRKQAQQADKKEDAEVKVREELGKLFS-<br>STKAGLDQEIQEHVKKETSSEENTQKVDEHYANSLQNLAQKSLE[ | 17b | 0 |
| dgb7p | ]VDLSNIDKELNHQKSQVEKMAEQKGITNEDKDSMLKKIEDIRKQAQQADKKEDAEVKVREELGKLFS-<br>STKAGLDQEIQEHVKKETSSEENTQKVDEHYANSLQNLAQKSLE[ | pTOPE | 100 |
| dgb8 | ]VDLSNIDKELNHQKSQVEKMAEQKGITNEDKDSMLKKIEDIRKQAQQADKKEDAEVKVREELGKLFS-<br>STKAGLDQEIQEHVKKETSSEENTQKVDEHYANSLQNLAQKSLEELDKATTNE[ | 17b | 0 |
| dgb8p | ]VDLSNIDKELNHQKSQVEKMAEQKGITNEDKDSMLKKIEDIRKQAQQADKKEDAEVKVREELGKLFS-<br>STKAGLDQEIQEHVKKETSSEENTQKVDEHYANSLQNLAQKSLEELDKATTNE[ | pTOPE | 100 |
| dgb10 | ]VDLSNIDKELNHQKSQVEKMAEQKGITNEDKDSMLKKIEDIRKQAQQADKKEDAEVKV[ | 17b | 10 |
| dgb12 | ....VDLSNIDKELNHQKSQVEKMAEQKGITNEDKDSMLKKIEDIRKQAQQADKKEDAEVKV[ | 17b | 20 |
| dgb11 | ....VDLSNIDKELNHQKSQVEKMAEQKGITNEDKDSMLKKIEDIRKQAQQADKKEDAEVKVREELGKLFS-<br>STKAGLDQEIQEHVKKETSSEENTQKVDEHYANSL[ | 17b | 20 |
| nv34qp | ....VDLSNIDKELNHQKSPVEKMAEPKGITNEDKDSMLKKIEDIRKQAQQADKKEDAEVKVREELGKLFS-<br>STKAGLDQEIQ... | 24a | 10 |
| dgb2 | ....VDLSNIDKELNHQKSQVEAMAEQAGITNEDKDSMLKKIEDIRKQAQQADKKEDAEVKVREELGKLFS-<br>STKAGLDQEIQ... | 24a | 60 |
| dgb1 | ....VDLSNIDKELNHQKSQE{—Δ—}AGITNEDKDSMLKKIEDIRKQAQQADKKEDAEVKVREELGKLFS-<br>STKAGLDQEIQ... | 24a | 0 |
| pnv231 | ....VDLSNIDKELNHQKSQVETMAEQLGITNEDKDSMLKKIEDIRKQAQQADKKEDAEVKVREELGKLFS-<br>STKAGLDQEIQ... | 24a | 60 |

What is claimed is:

1. A polysaccharide-protein conjugate comprising a mutant Cβ protein conjugated to a streptococcal capsular polysaccharide, wherein the mutant Cβ protein comprises an amino acid sequence A-$X_{202}X_{203}X_{204}X_{205}X_{206}X_{207}X_{208}X_{209}X_{210}X_{211}X_{212}X_{213}$-B, wherein A comprises in sequence amino acid residues 38–201 of SEQ ID NO: 2, B represents a sequence starting from amino acid 214 of SEQ ID NO: 2 and terminating at an amino acid between residues 1131 and 1164, inclusive, of SEQ ID NO: 2, and $X_{202}$ through $X_{213}$ are each selected independently from the group consisting of Ala, Val, Leu, Ile, Pro, Met, Phe, Trp, a bond, and a wild-type amino acid as found at a corresponding position of residues 202–213 of SEQ ID NO: 2, with the proviso that at least one of $X_{202}$ through $X_{213}$, inclusive, is other than the wild type amino acid found at the corresponding position of SEQ ID NO: 2, wherein said mutant Cβ protein exhibits reduced or no IgA binding activity in comparison to native Cβ protein which comprises the amino acid sequence of residue 38 through at least residue 1131 of SEQ ID NO: 2, and wherein antigenicity of the mutant Cβ protein in comparison to the native protein is substantially retained.

2. The polysaccharide-protein conjugate of claim 1, wherein a LPXTG motif in the sequence of said mutant Cβ protein located at amino acid residues corresponding to residues 1132–1136 of SEQ ID NO: 2 has been deleted.

3. A vaccine comprising at least one conjugate comprising a mutant Cβ protein conjugated to a polysaccharide, and a pharmaceutically acceptable carrier, wherein the mutant Cβ protein comprises an amino acid sequence A-$X_{202}X_{203}X_{204}X_{205}X_{206}X_{207}X_{208}X_{209}X_{210}X_{211}X_{212}X_{213}$-B, wherein A comprises in sequence amino acid residues 38–201 of SEQ ID NO: 2, B represents a sequence starting from amino acid 214 of SEQ ID NO: 2 and terminating at an amino acid between residues 1131 and 1164, inclusive, of SEQ ID NO: 2, and $X_{202}$ through $X_{213}$ are each selected independently from the group consisting of Ala, Val, Leu, Ile, Pro, Met, Phe, Trp, a bond, and a wild-type amino acid as found at a corresponding position of residues 202–213 of SEQ ID NO: 2, with the proviso that at least one of $X_{202}$ through $X_{213}$, inclusive, is other than the wild type amino acid found at the corresponding position of SEQ ID NO: 2, wherein said mutant Cβ protein exhibits reduced or no IgA binding activity in comparison to native Cβ protein which comprises the amino acid sequence of residue 38 through at least residue 1131 of SEQ ID NO: 2, and wherein antigenicity of the mutant Cβ protein in comparison to the native protein is substantially retained.

4. The vaccine of claim 3, wherein a LPXTG motif in the sequence of said mutant Cβ protein located at amino acid residues corresponding to residues 1132–1136 of SEQ ID NO: 2 has been deleted.

5. The vaccine of claim 3, wherein said polysaccharide to which said mutant Cβ protein is conjugated is selected from the group consisting of Group B streptococcal capsular polysaccharide types Ia, II, III and V.

6. The vaccine of claim 5, wherein a LPXTG motif in the sequence of said mutant Cβ protein located at amino acid residues corresponding to residues 1132–1136 of SEQ ID NO: 2 has been deleted.

7. The vaccine of claim 5 comprising at least two conjugates wherein each conjugate comprises a different one of said Group B streptococcal polysaccharide types conjugated to said mutant Cβ protein and wherein the amino acid sequences of mutant Cβ proteins of the at least two conjugates compared to each other are the same or different.

8. The vaccine of claim 7, wherein a LPXTG motif in the sequence of at least one said mutant Cβ proteins located at amino acid residues corresponding to residues 1132–1136 of SEQ ID NO: 2 has been deleted.

9. The vaccine of claim 5 comprising four conjugates wherein each conjugate comprises a different one of said Group B streptococcal polysaccharide types conjugated to said mutant Cβ protein and wherein the amino acid sequences of mutant Cβ proteins of the four conjugates compared to each other are the same or different.

10. The vaccine of claim 9, wherein a LPXTG motif in the sequence of at least one said mutant Cβ proteins located at amino acid residues corresponding to residues 1132–1136 of SEQ ID NO: 2 has been deleted.

11. A method of inducing an immune response in a mammal comprising administering the vaccine as claimed in any one of claims 3–9 or 10 to the mammal in an amount sufficient to induce an immune response in the mammal.

12. The method of claim 11, wherein said mammal is a human.

* * * * *

SEQUENCE LISTING

```
(1) GENERAL INFORMATION:

   (iii) NUMBER OF SEQUENCES: 34


(2) INFORMATION FOR SEQ ID NO: 1:

     (i) SEQUENCE CHARACTERISTICS:
          (A) LENGTH: 4200 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 320..3811

    (xi) SEQUENCE DESCRIPTION: SEQ ID NO: 1:

AAGCTTATGC TTGTCAATAA TCACAAATTT GTAGATCACT TCCTTTTTAG GACTGTAAAG     60

CATCCTAATT ACTTTTTAAA TATATTACCA GAACTAGTTG GTTTGGCCCT GGTGAGTCAT    120

GCTTATGTGA CATTCATCTT TATTTTTCCT GTCTATGCGG TTATTCTTTA TCAAAGAATA    180

GCAGAGGAAG AAAAATTATT GCAGGAAGTT ATTATTCCGA ATGGAAGAAT GAAAGGTTAA    240

AAATAATATA CCCAATTTAA TATGCAGTTC ATATTGGAAG GGTATACTGT AGATAAATAA    300

AATATTGGAG GATATCGAT ATG TTT AAA TCT AAT TAT GAA AGA AAA ATG CGT     352
                     Met Phe Lys Ser Asn Tyr Glu Arg Lys Met Arg
                       1               5                  10

TAT TCC ATT CGT AAA TTT AGT GTA GGA GTA GCT AGT GTA GCG GTA GCT      400
Tyr Ser Ile Arg Lys Phe Ser Val Gly Val Ala Ser Val Ala Val Ala
            15                  20                  25

AGT TTG TTC ATG GGA AGC GTT GCT CAT GCA AGT GAG CTT GTA AAG GAC      448
Ser Leu Phe Met Gly Ser Val Ala His Ala Ser Glu Leu Val Lys Asp
        30                  35                  40

GAT AGT GTG AAG ACT ACC GAG GTT GCA GCT AAG CCC TAT CCA AGT ATG      496
Asp Ser Val Lys Thr Thr Glu Val Ala Ala Lys Pro Tyr Pro Ser Met
    45                  50                  55

GCT CAA ACA GAT CAA GGA AAT AAT TCA TCA TCC TCG GAA CTT GAG ACA      544
Ala Gln Thr Asp Gln Gly Asn Asn Ser Ser Ser Ser Glu Leu Glu Thr
 60                  65                  70                  75

ACA AAG ATG GAA ATT CCT ACA ACA GAC ATA AAA AAA GCT GTT GAA CCG      592
Thr Lys Met Glu Ile Pro Thr Thr Asp Ile Lys Lys Ala Val Glu Pro
                 80                  85                  90

GTC GAG AAA ACA GCT GGG GAA ACA TCT GCC ACT GAT ACT GGA AAA CGA      640
Val Glu Lys Thr Ala Gly Glu Thr Ser Ala Thr Asp Thr Gly Lys Arg
            95                 100                 105

GAG AAA CAA TTA CAA CAA TGG AAA AAT AAT CTA AAA AAT GAT GTG GAT      688
Glu Lys Gln Leu Gln Gln Trp Lys Asn Asn Leu Lys Asn Asp Val Asp
        110                 115                 120

AAC ACA ATT CTA TCT CAT GAA CAG AAA AAT GAG TTT AAA ACA AAA ATT      736
Asn Thr Ile Leu Ser His Glu Gln Lys Asn Glu Phe Lys Thr Lys Ile
    125                 130                 135

GAT GAA ACA AAT GAT TCT GAT GCA TTA TTA GAA TTA GAA AAT CAA TTT      784
Asp Glu Thr Asn Asp Ser Asp Ala Leu Leu Glu Leu Glu Asn Gln Phe
140                 145                 150                 155

AAC GAA ACT AAT AGA CTG TTA CAC ATC AAA CAA CAT GAA GAA GTT GAG      832
Asn Glu Thr Asn Arg Leu Leu His Ile Lys Gln His Glu Glu Val Glu
                160                 165                 170

AAA GAT AAG AAA GCT AAG CAA CAG AAA ACT CTG AAA CAG TCA GAT ACG      880
```

-continued

```
Lys Asp Lys Lys Ala Lys Gln Gln Lys Thr Leu Lys Gln Ser Asp Thr
            175                 180                 185

AAA GTA GAT CTA AGC AAT ATT GAC AAA GAG CTT AAT CAT CAA AAA AGT      928
Lys Val Asp Leu Ser Asn Ile Asp Lys Glu Leu Asn His Gln Lys Ser
        190                 195                 200

CAA GTT GAA AAA ATG GCA GAG CAA AAG GGA ATC ACA AAT GAA GAT AAA      976
Gln Val Glu Lys Met Ala Glu Gln Lys Gly Ile Thr Asn Glu Asp Lys
    205                 210                 215

GAT TCT ATG CTG AAA AAA ATC GAA GAT ATT CGT AAA CAA GCT CAA CAA     1024
Asp Ser Met Leu Lys Lys Ile Glu Asp Ile Arg Lys Gln Ala Gln Gln
220                 225                 230                 235

GCA GAT AAA AAA GAA GAT GCC GAA GTA AAG GTT CGT GAA GAA CTA GGT     1072
Ala Asp Lys Lys Glu Asp Ala Glu Val Lys Val Arg Glu Glu Leu Gly
                240                 245                 250

AAA CTC TTT AGT TCA ACT AAA GCT GGT CTG GAT CAA GAA ATT CAA GAG     1120
Lys Leu Phe Ser Ser Thr Lys Ala Gly Leu Asp Gln Glu Ile Gln Glu
            255                 260                 265

CAT GTG AAG AAA GAA ACG AGT AGT GAG GAA AAT ACT CAG AAA GTT GAT     1168
His Val Lys Lys Glu Thr Ser Ser Glu Glu Asn Thr Gln Lys Val Asp
        270                 275                 280

GAA CAC TAT GCT AAT AGC CTT CAG AAC CTT GCT CAA AAA TCT CTT GAA     1216
Glu His Tyr Ala Asn Ser Leu Gln Asn Leu Ala Gln Lys Ser Leu Glu
    285                 290                 295

GAA CTA GAT AAG GCA ACT ACC AAT GAA CAA GCT ACA CAA GTT AAA AAT     1264
Glu Leu Asp Lys Ala Thr Thr Asn Glu Gln Ala Thr Gln Val Lys Asn
300                 305                 310                 315

CAA TTC TTA GAA AAC GCT CAA AAG CTC AAA GAA ATA CAA CCT CTT ATC     1312
Gln Phe Leu Glu Asn Ala Gln Lys Leu Lys Glu Ile Gln Pro Leu Ile
                320                 325                 330

AAA GAA ACG AAT GTG AAA TTG TAT AAG GCT ATG AGT GAG AGC TTG GAG     1360
Lys Glu Thr Asn Val Lys Leu Tyr Lys Ala Met Ser Glu Ser Leu Glu
            335                 340                 345

CAG GTT GAG AAG GAA TTA AAA CAT AAT TCG GAA GCT AAT TTA GAA GAT     1408
Gln Val Glu Lys Glu Leu Lys His Asn Ser Glu Ala Asn Leu Glu Asp
        350                 355                 360

TTG GTT GCG AAA TCT AAA GAA ATC GTA AGA GAA TAC GAA GGA AAA CTT     1456
Leu Val Ala Lys Ser Lys Glu Ile Val Arg Glu Tyr Glu Gly Lys Leu
    365                 370                 375

AAT CAA TCT AAA AAT CTT CCA GAA TTA AAG CAA CTA GAA GAG GAA GCT     1504
Asn Gln Ser Lys Asn Leu Pro Glu Leu Lys Gln Leu Glu Glu Glu Ala
380                 385                 390                 395

CAT TCG AAG TTG AAA CAA GTT GTG GAG GAT TTT AGA AAA AAA TTT AAA     1552
His Ser Lys Leu Lys Gln Val Val Glu Asp Phe Arg Lys Lys Phe Lys
                400                 405                 410

ACG TCA GAG CAA GTG ACA CCA AAA AAA CGT GTC AAA CGA GAT TTA GCT     1600
Thr Ser Glu Gln Val Thr Pro Lys Lys Arg Val Lys Arg Asp Leu Ala
            415                 420                 425

GCT AAT GAA AAT AAT CAA CAA AAG ATT GAG TTA ACA GTT TCA CCA GAG     1648
Ala Asn Glu Asn Asn Gln Gln Lys Ile Glu Leu Thr Val Ser Pro Glu
        430                 435                 440

AAT ATC ACT GTA TAT GAA GGT GAA GAC GTG AAA TTT ACA GTC ACA GCT     1696
Asn Ile Thr Val Tyr Glu Gly Glu Asp Val Lys Phe Thr Val Thr Ala
    445                 450                 455

AAA AGT GAT TCG AAG ACG ACG TTG GAC TTC AGT GAT CTT TTA ACA AAA     1744
Lys Ser Asp Ser Lys Thr Thr Leu Asp Phe Ser Asp Leu Leu Thr Lys
460                 465                 470                 475

TAT AAT CCG TCT GTA TCA GAT AGA ATT AGT ACA AAT TAT AAG ACT AAC     1792
Tyr Asn Pro Ser Val Ser Asp Arg Ile Ser Thr Asn Tyr Lys Thr Asn
                480                 485                 490
```

-continued

```
ACG GAT AAT CAT AAG ATT GCC GAA ATC ACT ATC AAG AAT TTG AAG CTA     1840
Thr Asp Asn His Lys Ile Ala Glu Ile Thr Ile Lys Asn Leu Lys Leu
            495                 500                 505

AAT GAA AGT CAA ACA GTG ACT CTA AAA GCT AAA GAT GAT TCT GGC AAT     1888
Asn Glu Ser Gln Thr Val Thr Leu Lys Ala Lys Asp Asp Ser Gly Asn
        510                 515                 520

GTA GTT GAA AAA ACA TTC ACT ATT ACA GTG CAA AAG AAA GAG GAG AAA     1936
Val Val Glu Lys Thr Phe Thr Ile Thr Val Gln Lys Lys Glu Glu Lys
    525                 530                 535

CAA GTT CCT AAA ACA CCA GAG CAG AAA GAT TCT AAA ACG GAA GAA AAG     1984
Gln Val Pro Lys Thr Pro Glu Gln Lys Asp Ser Lys Thr Glu Glu Lys
540                 545                 550                 555

GTT CCT CAA GAA CCA AAA TCA AAT GAC AAG AAT CAA TTA CAA GAG TTG     2032
Val Pro Gln Glu Pro Lys Ser Asn Asp Lys Asn Gln Leu Gln Glu Leu
                560                 565                 570

ATT AAA TCA GCT CAA CAA GAA CTG GAA AAG TTA GAA AAA GCA ATA AAA     2080
Ile Lys Ser Ala Gln Gln Glu Leu Glu Lys Leu Glu Lys Ala Ile Lys
            575                 580                 585

GAA TTA ATG GAG CAA CCA GAG ATT CCA TCC AAT CCA GAG TAT GGT ATT     2128
Glu Leu Met Glu Gln Pro Glu Ile Pro Ser Asn Pro Glu Tyr Gly Ile
        590                 595                 600

CAA AAA TCT ATT TGG GAG TCA CAA AAA GAG CCT ATC CAG GAA GCC ATA     2176
Gln Lys Ser Ile Trp Glu Ser Gln Lys Glu Pro Ile Gln Glu Ala Ile
    605                 610                 615

ACA AGT TTT AAG AAG ATT ATT GGT GAT TCA TCT TCA AAA TAC TAC ACA     2224
Thr Ser Phe Lys Lys Ile Ile Gly Asp Ser Ser Ser Lys Tyr Tyr Thr
620                 625                 630                 635

GAG CAC TAT TTT AAC AAA TAT AAA TCT GAT TTT ATG AAT TAT CAA CTT     2272
Glu His Tyr Phe Asn Lys Tyr Lys Ser Asp Phe Met Asn Tyr Gln Leu
                640                 645                 650

CAT GCA CAA ATG GAG ATG CTG ACT AGA AAA GTG GTT CAG TAT ATG AAC     2320
His Ala Gln Met Glu Met Leu Thr Arg Lys Val Val Gln Tyr Met Asn
            655                 660                 665

AAA TAT CCT GAT AAT GCA GAA ATT AAA AAG ATA TTT GAG TCA GAT ATG     2368
Lys Tyr Pro Asp Asn Ala Glu Ile Lys Lys Ile Phe Glu Ser Asp Met
        670                 675                 680

AAG AGA ACG AAA GAA GAT AAT TAC GGA AGT TTA GAA AAT GAT GCT TTG     2416
Lys Arg Thr Lys Glu Asp Asn Tyr Gly Ser Leu Glu Asn Asp Ala Leu
    685                 690                 695

AAA GGC TAT TTT GAG AAA TAT TTC CTT ACA CCA TTT AAT AAA ATT AAG     2464
Lys Gly Tyr Phe Glu Lys Tyr Phe Leu Thr Pro Phe Asn Lys Ile Lys
700                 705                 710                 715

CAG ATT GTA GAT GAT TTG GAT AAA AAA GTA GAA CAA GAT CAG CCA GCA     2512
Gln Ile Val Asp Asp Leu Asp Lys Lys Val Glu Gln Asp Gln Pro Ala
                720                 725                 730

CCA ATT CCG GAA AAT TCA GAA ATG GAT CAG GCT AAG GAA AAG GCT AAG     2560
Pro Ile Pro Glu Asn Ser Glu Met Asp Gln Ala Lys Glu Lys Ala Lys
            735                 740                 745

ATT GCT GTA TCG AAG TAT ATG AGT AAG GTT TTA GAT GGA GTT CAT CAA     2608
Ile Ala Val Ser Lys Tyr Met Ser Lys Val Leu Asp Gly Val His Gln
        750                 755                 760

CAT CTG CAG AAG AAA AAT AAC AGT AAA ATT GTT GAT CTT TTT AAG GAA     2656
His Leu Gln Lys Lys Asn Asn Ser Lys Ile Val Asp Leu Phe Lys Glu
    765                 770                 775

CTT GAA GCG ATT AAA CAA CAA ACT ATT TTT GAT ATT GAC AAT GCA AAG     2704
Leu Glu Ala Ile Lys Gln Gln Thr Ile Phe Asp Ile Asp Asn Ala Lys
780                 785                 790                 795

ACT GAA GTA GAG ATT GAT AAC TTA GTA CAC GAT GCA TTC TCA AAA ATG     2752
Thr Glu Val Glu Ile Asp Asn Leu Val His Asp Ala Phe Ser Lys Met
                800                 805                 810
```

-continued

```
AAT GCT ACT GTT GCT AAA TTT CAA AAA GGT CTA GAG ACA AAT ACG CCA     2800
Asn Ala Thr Val Ala Lys Phe Gln Lys Gly Leu Glu Thr Asn Thr Pro
            815                 820                 825

GAA ACT CCA GAT ACA CCG AAG ATT CCA GAG CTA CCT CAA GCC CCA GAT     2848
Glu Thr Pro Asp Thr Pro Lys Ile Pro Glu Leu Pro Gln Ala Pro Asp
        830                 835                 840

ACA CCG CAG GCT CCA GAC ACA CCG CAT GTT CCG GAA TCA CCA AAG GCC     2896
Thr Pro Gln Ala Pro Asp Thr Pro His Val Pro Glu Ser Pro Lys Ala
    845                 850                 855

CCA GAA GCA CCG CGT GTT CCG GAA TCA CCA AAG ACT CCA GAA GCA CCG     2944
Pro Glu Ala Pro Arg Val Pro Glu Ser Pro Lys Thr Pro Glu Ala Pro
860                 865                 870                 875

CAT GTT CCG GAA TCA CCA AAG GCC CCA GAA GCA CCG CGT GTT CCG GAA     2992
His Val Pro Glu Ser Pro Lys Ala Pro Glu Ala Pro Arg Val Pro Glu
                880                 885                 890

TCA CCA AAG ACT CCA GAA GCA CCG CAT GTT CCG GAA TCA CCA AAG ACT     3040
Ser Pro Lys Thr Pro Glu Ala Pro His Val Pro Glu Ser Pro Lys Thr
            895                 900                 905

CCA GAA GCA CCA AAG ATT CCG AAA CCC CCT AAG ACT CCA GAC GTC CCT     3088
Pro Glu Ala Pro Lys Ile Pro Lys Pro Pro Lys Thr Pro Asp Val Pro
        910                 915                 920

AAG CTT CCA GAC GTC CCT AAG CTT CCA GAC GTC CCT AAG CTT CCA GAT     3136
Lys Leu Pro Asp Val Pro Lys Leu Pro Asp Val Pro Lys Leu Pro Asp
    925                 930                 935

GCA CCG AAG TTA CCA GAT GGG TTA AAT AAA GTT GGA CAA GCA GTA TTT     3184
Ala Pro Lys Leu Pro Asp Gly Leu Asn Lys Val Gly Gln Ala Val Phe
940                 945                 950                 955

ACA TCA ACT GAT GGA AAT ACT AAG GTT ACG GTT GTA TTT GAT AAA CCT     3232
Thr Ser Thr Asp Gly Asn Thr Lys Val Thr Val Val Phe Asp Lys Pro
                960                 965                 970

ACA GAT GCT GAT AAG TTA CAT CTC AAG GAA GTA ACG ACG AAA GAG TTG     3280
Thr Asp Ala Asp Lys Leu His Leu Lys Glu Val Thr Thr Lys Glu Leu
            975                 980                 985

GCT GAT AAA ATT GCT CAT AAA ACA GGA GGA GGA ACA GTT CGT GTG TTT     3328
Ala Asp Lys Ile Ala His Lys Thr Gly Gly Gly Thr Val Arg Val Phe
        990                 995                 1000

GAC TTA TCT CTT TCT AAA GGA GGC AAG GAA ACA CAT GTC AAT GGA GAA     3376
Asp Leu Ser Leu Ser Lys Gly Gly Lys Glu Thr His Val Asn Gly Glu
    1005                1010                1015

CGA ACT GTT CGG CTC GCG CTT GGG CAG ACT GGC TCA GAT GTT CAC GTC     3424
Arg Thr Val Arg Leu Ala Leu Gly Gln Thr Gly Ser Asp Val His Val
1020                1025                1030                1035

TAT CAC GTA AAG GAA AAT GGC GAC CTT GAG CGT ATT CCT TCT AAA GTT     3472
Tyr His Val Lys Glu Asn Gly Asp Leu Glu Arg Ile Pro Ser Lys Val
                1040                1045                1050

GAA AAT GGG CAA GTT GTT TTT AAA ACG AAC CAC TTC AGT TTG TTT GCG     3520
Glu Asn Gly Gln Val Val Phe Lys Thr Asn His Phe Ser Leu Phe Ala
            1055                1060                1065

ATT AAG ACA CTT TCT AAG GAT CAA AAT GTT ACT CCA CCG AAG CAG ACT     3568
Ile Lys Thr Leu Ser Lys Asp Gln Asn Val Thr Pro Pro Lys Gln Thr
        1070                1075                1080

AAA CCT TCT ACC CAA GGC AGT CAA GTA GAG ATT GCA GAG AGT CAA ACT     3616
Lys Pro Ser Thr Gln Gly Ser Gln Val Glu Ile Ala Glu Ser Gln Thr
    1085                1090                1095

GGA AAA TTC CAG AGT AAA GCA GCT AAT CAT AAA GCA CTG GCT ACT GGA     3664
Gly Lys Phe Gln Ser Lys Ala Ala Asn His Lys Ala Leu Ala Thr Gly
1100                1105                1110                1115

AAT GAA ACA GTG GCA AAA GGA AAT CCT ACA TCA ACA ACG GAA AAG AAA     3712
Asn Glu Thr Val Ala Lys Gly Asn Pro Thr Ser Thr Thr Glu Lys Lys
```

-continued

```
              1120                1125                1130

TTG CCA TAT ACA GGA GTG GCA TCT AAT CTA GTT CTT GAA ATT ATG GGT     3760
Leu Pro Tyr Thr Gly Val Ala Ser Asn Leu Val Leu Glu Ile Met Gly
            1135                1140                1145

CTC CTT GGT TTG ATT GGA ACT TCA TTC ATC GCA ATG AAA AGA AGA AAA     3808
Leu Leu Gly Leu Ile Gly Thr Ser Phe Ile Ala Met Lys Arg Arg Lys
        1150                1155                1160

TCA TGATTCAGTT TTTTAAAAAT ATCCACTTTC GATATCTAGC ATTTGATTGG          3861
Ser

TTATCTGTGG ATGATTCTAA AGATGTTACC TATCGTTGGT ATGTAACAAT TATAAGTCAT   3921

TTCATATAAA AGAGGCTCTT TGTCAACTGT AGTTGGTTGA AACAAGGCTA CAAACTAGAA   3981

AGGACGCATT TTGTCCTTTC TTTTTGATGT TGAGGGCAAT GAAAATACGC TTTTTGAAGT   4041

TTTCAAAATT CCGAAAACTA AAGATATTGT ATTTGAAAAG TTTAATGAGA TGATTAGTTG   4101

CTTCCAATTT TGCGTTGGAG TAGGTTTACT GAAGGACGTT GACGATATTC TCTTTGCTTT   4161

TGAGAATGAT TTTAAAGATA GTCTGAAAAA GAGGATGAA                          4200


(2) INFORMATION FOR SEQ ID NO: 2:

     (i) SEQUENCE CHARACTERISTICS:
          (A) LENGTH: 1164 amino acids
          (B) TYPE: amino acid
          (D) TOPOLOGY: linear

    (ii) MOLECULE TYPE: protein

    (xi) SEQUENCE DESCRIPTION: SEQ ID NO: 2:

Met Phe Lys Ser Asn Tyr Glu Arg Lys Met Arg Tyr Ser Ile Arg Lys
  1               5                  10                  15

Phe Ser Val Gly Val Ala Ser Val Ala Val Ala Ser Leu Phe Met Gly
            20                  25                  30

Ser Val Ala His Ala Ser Glu Leu Val Lys Asp Asp Ser Val Lys Thr
        35                  40                  45

Thr Glu Val Ala Ala Lys Pro Tyr Pro Ser Met Ala Gln Thr Asp Gln
    50                  55                  60

Gly Asn Asn Ser Ser Ser Ser Glu Leu Glu Thr Thr Lys Met Glu Ile
 65                  70                  75                  80

Pro Thr Thr Asp Ile Lys Lys Ala Val Glu Pro Val Glu Lys Thr Ala
                85                  90                  95

Gly Glu Thr Ser Ala Thr Asp Thr Gly Lys Arg Glu Lys Gln Leu Gln
            100                 105                 110

Gln Trp Lys Asn Asn Leu Lys Asn Asp Val Asp Asn Thr Ile Leu Ser
        115                 120                 125

His Glu Gln Lys Asn Glu Phe Lys Thr Lys Ile Asp Glu Thr Asn Asp
    130                 135                 140

Ser Asp Ala Leu Leu Glu Leu Glu Asn Gln Phe Asn Glu Thr Asn Arg
145                 150                 155                 160

Leu Leu His Ile Lys Gln His Glu Glu Val Glu Lys Asp Lys Lys Ala
                165                 170                 175

Lys Gln Gln Lys Thr Leu Lys Gln Ser Asp Thr Lys Val Asp Leu Ser
            180                 185                 190

Asn Ile Asp Lys Glu Leu Asn His Gln Lys Ser Gln Val Glu Lys Met
        195                 200                 205

Ala Glu Gln Lys Gly Ile Thr Asn Glu Asp Lys Asp Ser Met Leu Lys
    210                 215                 220
```

-continued

```
Lys Ile Glu Asp Ile Arg Lys Gln Ala Gln Gln Ala Asp Lys Lys Glu
225                 230                 235                 240

Asp Ala Glu Val Lys Val Arg Glu Glu Leu Gly Lys Leu Phe Ser Ser
                245                 250                 255

Thr Lys Ala Gly Leu Asp Gln Glu Ile Gln Glu His Val Lys Lys Glu
            260                 265                 270

Thr Ser Ser Glu Glu Asn Thr Gln Lys Val Asp Glu His Tyr Ala Asn
        275                 280                 285

Ser Leu Gln Asn Leu Ala Gln Lys Ser Leu Glu Glu Leu Asp Lys Ala
    290                 295                 300

Thr Thr Asn Glu Gln Ala Thr Gln Val Lys Asn Gln Phe Leu Glu Asn
305                 310                 315                 320

Ala Gln Lys Leu Lys Glu Ile Gln Pro Leu Ile Lys Glu Thr Asn Val
                325                 330                 335

Lys Leu Tyr Lys Ala Met Ser Glu Ser Leu Glu Gln Val Glu Lys Glu
            340                 345                 350

Leu Lys His Asn Ser Glu Ala Asn Leu Glu Asp Leu Val Ala Lys Ser
        355                 360                 365

Lys Glu Ile Val Arg Glu Tyr Glu Gly Lys Leu Asn Gln Ser Lys Asn
    370                 375                 380

Leu Pro Glu Leu Lys Gln Leu Glu Glu Glu Ala His Ser Lys Leu Lys
385                 390                 395                 400

Gln Val Val Glu Asp Phe Arg Lys Lys Phe Lys Thr Ser Glu Gln Val
                405                 410                 415

Thr Pro Lys Lys Arg Val Lys Arg Asp Leu Ala Ala Asn Glu Asn Asn
            420                 425                 430

Gln Gln Lys Ile Glu Leu Thr Val Ser Pro Glu Asn Ile Thr Val Tyr
        435                 440                 445

Glu Gly Glu Asp Val Lys Phe Thr Val Thr Ala Lys Ser Asp Ser Lys
    450                 455                 460

Thr Thr Leu Asp Phe Ser Asp Leu Leu Thr Lys Tyr Asn Pro Ser Val
465                 470                 475                 480

Ser Asp Arg Ile Ser Thr Asn Tyr Lys Thr Asn Thr Asp Asn His Lys
                485                 490                 495

Ile Ala Glu Ile Thr Ile Lys Asn Leu Lys Leu Asn Glu Ser Gln Thr
            500                 505                 510

Val Thr Leu Lys Ala Lys Asp Asp Ser Gly Asn Val Val Glu Lys Thr
        515                 520                 525

Phe Thr Ile Thr Val Gln Lys Lys Glu Glu Lys Gln Val Pro Lys Thr
    530                 535                 540

Pro Glu Gln Lys Asp Ser Lys Thr Glu Glu Lys Val Pro Gln Glu Pro
545                 550                 555                 560

Lys Ser Asn Asp Lys Asn Gln Leu Gln Glu Leu Ile Lys Ser Ala Gln
                565                 570                 575

Gln Glu Leu Glu Lys Leu Glu Lys Ala Ile Lys Glu Leu Met Glu Gln
            580                 585                 590

Pro Glu Ile Pro Ser Asn Pro Glu Tyr Gly Ile Gln Lys Ser Ile Trp
        595                 600                 605

Glu Ser Gln Lys Glu Pro Ile Gln Glu Ala Ile Thr Ser Phe Lys Lys
    610                 615                 620

Ile Ile Gly Asp Ser Ser Ser Lys Tyr Tyr Thr Glu His Tyr Phe Asn
625                 630                 635                 640

Lys Tyr Lys Ser Asp Phe Met Asn Tyr Gln Leu His Ala Gln Met Glu
```

-continued

```
            645                 650                 655

Met Leu Thr Arg Lys Val Val Gln Tyr Met Asn Lys Tyr Pro Asp Asn
        660                 665                 670

Ala Glu Ile Lys Lys Ile Phe Glu Ser Asp Met Lys Arg Thr Lys Glu
    675                 680                 685

Asp Asn Tyr Gly Ser Leu Glu Asn Asp Ala Leu Lys Gly Tyr Phe Glu
    690                 695                 700

Lys Tyr Phe Leu Thr Pro Phe Asn Lys Ile Lys Gln Ile Val Asp Asp
705                 710                 715                 720

Leu Asp Lys Lys Val Glu Gln Asp Gln Pro Ala Pro Ile Pro Glu Asn
            725                 730                 735

Ser Glu Met Asp Gln Ala Lys Glu Lys Ala Lys Ile Ala Val Ser Lys
        740                 745                 750

Tyr Met Ser Lys Val Leu Asp Gly Val His Gln His Leu Gln Lys Lys
    755                 760                 765

Asn Asn Ser Lys Ile Val Asp Leu Phe Lys Glu Leu Glu Ala Ile Lys
    770                 775                 780

Gln Gln Thr Ile Phe Asp Ile Asp Asn Ala Lys Thr Glu Val Glu Ile
785                 790                 795                 800

Asp Asn Leu Val His Asp Ala Phe Ser Lys Met Asn Ala Thr Val Ala
            805                 810                 815

Lys Phe Gln Lys Gly Leu Glu Thr Asn Thr Pro Glu Thr Pro Asp Thr
        820                 825                 830

Pro Lys Ile Pro Glu Leu Pro Gln Ala Pro Asp Thr Pro Gln Ala Pro
    835                 840                 845

Asp Thr Pro His Val Pro Glu Ser Pro Lys Ala Pro Glu Ala Pro Arg
    850                 855                 860

Val Pro Glu Ser Pro Lys Thr Pro Glu Ala Pro His Val Pro Glu Ser
865                 870                 875                 880

Pro Lys Ala Pro Glu Ala Pro Arg Val Pro Glu Ser Pro Lys Thr Pro
            885                 890                 895

Glu Ala Pro His Val Pro Glu Ser Pro Lys Thr Pro Glu Ala Pro Lys
        900                 905                 910

Ile Pro Lys Pro Pro Lys Thr Pro Asp Val Pro Lys Leu Pro Asp Val
    915                 920                 925

Pro Lys Leu Pro Asp Val Pro Lys Leu Pro Asp Ala Pro Lys Leu Pro
    930                 935                 940

Asp Gly Leu Asn Lys Val Gly Gln Ala Val Phe Thr Ser Thr Asp Gly
945                 950                 955                 960

Asn Thr Lys Val Thr Val Val Phe Asp Lys Pro Thr Asp Ala Asp Lys
            965                 970                 975

Leu His Leu Lys Glu Val Thr Thr Lys Glu Leu Ala Asp Lys Ile Ala
        980                 985                 990

His Lys Thr Gly Gly Gly Thr Val Arg Val Phe Asp Leu Ser Leu Ser
    995                 1000                1005

Lys Gly Gly Lys Glu Thr His Val Asn Gly Glu Arg Thr Val Arg Leu
    1010                1015                1020

Ala Leu Gly Gln Thr Gly Ser Asp Val His Val Tyr His Val Lys Glu
1025                1030                1035                1040

Asn Gly Asp Leu Glu Arg Ile Pro Ser Lys Val Glu Asn Gly Gln Val
            1045                1050                1055

Val Phe Lys Thr Asn His Phe Ser Leu Phe Ala Ile Lys Thr Leu Ser
        1060                1065                1070
```

-continued

```
Lys Asp Gln Asn Val Thr Pro Pro Lys Gln Thr Lys Pro Ser Thr Gln
        1075                1080                1085

Gly Ser Gln Val Glu Ile Ala Glu Ser Gln Thr Gly Lys Phe Gln Ser
    1090                1095                1100

Lys Ala Ala Asn His Lys Ala Leu Ala Thr Gly Asn Glu Thr Val Ala
1105                1110                1115                1120

Lys Gly Asn Pro Thr Ser Thr Thr Glu Lys Lys Leu Pro Tyr Thr Gly
                1125                1130                1135

Val Ala Ser Asn Leu Val Leu Glu Ile Met Gly Leu Leu Gly Leu Ile
            1140                1145                1150

Gly Thr Ser Phe Ile Ala Met Lys Arg Arg Lys Ser
        1155                1160
```

(2) INFORMATION FOR SEQ ID NO: 3:

(i) SEQUENCE CHARACTERISTICS:
(A) LENGTH: 3312 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 1..3312

(xi) SEQUENCE DESCRIPTION: SEQ ID NO: 3:

```
GAA GGA GAT ATA CAT ATG AGT GAG CTT GTA AAG GAC GAT AGT GTG AAG       48
Glu Gly Asp Ile His Met Ser Glu Leu Val Lys Asp Asp Ser Val Lys
  1               5                  10                  15

ACT ACC GAG GTT GCA GCT AAG CCC TAT CCA AGT ATG GCT CAA ACA GAT       96
Thr Thr Glu Val Ala Ala Lys Pro Tyr Pro Ser Met Ala Gln Thr Asp
            20                  25                  30

CAA GGA AAT AAT TCA TCA TCC TCG GAA CTT GAG ACA ACA AGG ATG GAA      144
Gln Gly Asn Asn Ser Ser Ser Ser Glu Leu Glu Thr Thr Arg Met Glu
        35                  40                  45

ATT CCT ACA ACA CAC ATA AAA AAA GCT GTT GAA CCG GTC GAG AAA ACA      192
Ile Pro Thr Thr His Ile Lys Lys Ala Val Glu Pro Val Glu Lys Thr
     50                  55                  60

GCT GGG GAA ACA TCT GCC ACT GAT ACT GGA AAA CGA GAG AAA CAA TTA      240
Ala Gly Glu Thr Ser Ala Thr Asp Thr Gly Lys Arg Glu Lys Gln Leu
 65                  70                  75                  80

CAA CAA TGG AAA AAT AAT CTA AAA AAT GAT GTG GAT AAC ACA ATT CTA      288
Gln Gln Trp Lys Asn Asn Leu Lys Asn Asp Val Asp Asn Thr Ile Leu
                 85                  90                  95

TCT CAT GAA CAG AAA AAT GAG TTT AAA ACA AAA ATT GAT GAA ACA AAT      336
Ser His Glu Gln Lys Asn Glu Phe Lys Thr Lys Ile Asp Glu Thr Asn
            100                 105                 110

GAT TCT GAT GCA TTA TTA GAA TTA GAA AAT CAA TTT AAC GAA ACT AAT      384
Asp Ser Asp Ala Leu Leu Glu Leu Glu Asn Gln Phe Asn Glu Thr Asn
        115                 120                 125

AGA CTG TTA CAC ATC AAA CAA CAT GAA GAA GTT GAG AAA CAT AAC AAA      432
Arg Leu Leu His Ile Lys Gln His Glu Glu Val Glu Lys His Asn Lys
    130                 135                 140

CCT AAC CAA CAG AAA ACT CTG AAA CAG TCA GAT ACG AAA GTA GAT CTA      480
Pro Asn Gln Gln Lys Thr Leu Lys Gln Ser Asp Thr Lys Val Asp Leu
145                 150                 155                 160

AGC AAT ATT GAC AAA GAG CTT AAT CAT CAA AAA AGT CAA GTT GAA GCA      528
Ser Asn Ile Asp Lys Glu Leu Asn His Gln Lys Ser Gln Val Glu Ala
                165                 170                 175
```

-continued

```
ATG GCA GAG CAA GCG GGA ATC ACA AAT GAA GAT AAA GAT TCT ATG CTG      576
Met Ala Glu Gln Ala Gly Ile Thr Asn Glu Asp Lys Asp Ser Met Leu
            180                 185                 190

AAA AAA ATC GAA GAT ATT CGT AAA CAA GCT CAA CAA GCA GAT AAA AAA      624
Lys Lys Ile Glu Asp Ile Arg Lys Gln Ala Gln Gln Ala Asp Lys Lys
        195                 200                 205

GAA GAT GCC GAA GTA AAG GTT CGT GAA GAA CTA GGT AAA CTC TTT AGT      672
Glu Asp Ala Glu Val Lys Val Arg Glu Glu Leu Gly Lys Leu Phe Ser
    210                 215                 220

TCA ACT AAA GCT GGT CTG GAT CAA CAA ATT CAA GAG CAT GTG AAG AAA      720
Ser Thr Lys Ala Gly Leu Asp Gln Gln Ile Gln Glu His Val Lys Lys
225                 230                 235                 240

GAA ACG AGT AGT GAG GAA AAT ACT CAG AAA GTT GAT GAA CAC TAT GCT      768
Glu Thr Ser Ser Glu Glu Asn Thr Gln Lys Val Asp Glu His Tyr Ala
                245                 250                 255

AAT AGC CTT CAG AAC CTT GCT CAA AAA TCT CTT GAA GAA CTA GAT AAG      816
Asn Ser Leu Gln Asn Leu Ala Gln Lys Ser Leu Glu Glu Leu Asp Lys
            260                 265                 270

GCA ACT ACC AAT GAA CAA GCT ACA CAA GTT AAA AAT CAA TTC TTA GAA      864
Ala Thr Thr Asn Glu Gln Ala Thr Gln Val Lys Asn Gln Phe Leu Glu
        275                 280                 285

AAC GCT CAA AAG CTC AAA GAA ATA CAA CCT CTT ATC AAA GAA ACG AAT      912
Asn Ala Gln Lys Leu Lys Glu Ile Gln Pro Leu Ile Lys Glu Thr Asn
    290                 295                 300

GTG AAA TTG TAT AAG GCT ATG AGT GAG AGC TTG GAG CAG GTT GAG AAG      960
Val Lys Leu Tyr Lys Ala Met Ser Glu Ser Leu Glu Gln Val Glu Lys
305                 310                 315                 320

GAA TTA AAA CAT AAT TCG GAA GCT AAT TTA CAA GAT TTG GTT GCG AAA     1008
Glu Leu Lys His Asn Ser Glu Ala Asn Leu Gln Asp Leu Val Ala Lys
                325                 330                 335

TCT AAA GAA ATC GTA AGA GAA TAC GAA GGA AAA CTT AAT CAA TCT AAA     1056
Ser Lys Glu Ile Val Arg Glu Tyr Glu Gly Lys Leu Asn Gln Ser Lys
            340                 345                 350

AAT CTT CCA GAA TTA AAG CAA CTA GAA GAG GAA GCT CAT TCG AAG TTG     1104
Asn Leu Pro Glu Leu Lys Gln Leu Glu Glu Glu Ala His Ser Lys Leu
        355                 360                 365

AAA CAA GTT GTG GAG CAT TTT AGA AAA AAA TTT AAA ACG TCA GAG CAA     1152
Lys Gln Val Val Glu His Phe Arg Lys Lys Phe Lys Thr Ser Glu Gln
    370                 375                 380

GTG ACA CCA AAA AAA CGT GTC AAA CGA GAT TTA GCT GCT AAT GAA AAT     1200
Val Thr Pro Lys Lys Arg Val Lys Arg Asp Leu Ala Ala Asn Glu Asn
385                 390                 395                 400

AAT CAA CAA AAG ATT GAG TTA ACA GTT TCA CCA GAG AAT ATC ACT GTA     1248
Asn Gln Gln Lys Ile Glu Leu Thr Val Ser Pro Glu Asn Ile Thr Val
                405                 410                 415

TAT GAA GGT GAA GAC GTG AAA TTT ACA GTC ACA GCT AAA AGT GAT TCG     1296
Tyr Glu Gly Glu Asp Val Lys Phe Thr Val Thr Ala Lys Ser Asp Ser
            420                 425                 430

AAG ACG ACG TTG GAC TTC AGT GAT CTT TTA ACA AAA TAT AAT CCG TCT     1344
Lys Thr Thr Leu Asp Phe Ser Asp Leu Leu Thr Lys Tyr Asn Pro Ser
        435                 440                 445

GTA TCA GAT AGA ATT AGT ACA AAT TAT AAG ACT AAC ACG GAT AAT CAT     1392
Val Ser Asp Arg Ile Ser Thr Asn Tyr Lys Thr Asn Thr Asp Asn His
    450                 455                 460

AAG ATT GCC GAA ATC ACT ATC AAG AAT TTG AAG CTA AAT CAA AGT CAA     1440
Lys Ile Ala Glu Ile Thr Ile Lys Asn Leu Lys Leu Asn Gln Ser Gln
465                 470                 475                 480

ACA GTG ACT CTA AAA GCT AAA GAT GAT TCT GGC AAT GTA GTT GAA AAA     1488
Thr Val Thr Leu Lys Ala Lys Asp Asp Ser Gly Asn Val Val Glu Lys
```

-continued

```
                485                 490                 495

ACA TTC ACT ATT ACA GTC CAA AAG AAA GAG GAG AAA CAA GTT CCT AAA     1536
Thr Phe Thr Ile Thr Val Gln Lys Lys Glu Glu Lys Gln Val Pro Lys
            500                 505                 510

ACA CCA GAG CAG AAA CAT TCT AAA ACG GAA CAA AAC GTT CCT CAA GAA     1584
Thr Pro Glu Gln Lys His Ser Lys Thr Glu Gln Asn Val Pro Gln Glu
        515                 520                 525

CCA AAA TCA AAT GAC AAG AAT CAA TTA CAA GAG TTG ATT AAA TCA GCT     1632
Pro Lys Ser Asn Asp Lys Asn Gln Leu Gln Glu Leu Ile Lys Ser Ala
    530                 535                 540

CAA CAA GAA CTC GAA AAG TTA GAA AAA GCA ATA AAA GAA TTA ATG GAG     1680
Gln Gln Glu Leu Glu Lys Leu Glu Lys Ala Ile Lys Glu Leu Met Glu
545                 550                 555                 560

CAA CCA GAG ATT CCA TCC AAT CCA GAG TAT GGT ATT CAA AAA TCT ATT     1728
Gln Pro Glu Ile Pro Ser Asn Pro Glu Tyr Gly Ile Gln Lys Ser Ile
                565                 570                 575

TGG GAG TCA CAA AAA GAG CCT ATC CAG GAA GCC ATA ACA AGT TTT AAC     1776
Trp Glu Ser Gln Lys Glu Pro Ile Gln Glu Ala Ile Thr Ser Phe Asn
            580                 585                 590

AAG ATT ATT GGT GAT TCA TCT TCA AAA TAC TAC ACA GAG CAC TAT TTT     1824
Lys Ile Ile Gly Asp Ser Ser Ser Lys Tyr Tyr Thr Glu His Tyr Phe
        595                 600                 605

AAC AAA TAT AAA TCT CAT TTT ATG AAT TAT CAA CTT CAT GCA CAA ATG     1872
Asn Lys Tyr Lys Ser His Phe Met Asn Tyr Gln Leu His Ala Gln Met
    610                 615                 620

GAG ATC CTG ACT AGA AAA GTG GTT CAG TAT ATG AAC AAA TAT CCT GAT     1920
Glu Ile Leu Thr Arg Lys Val Val Gln Tyr Met Asn Lys Tyr Pro Asp
625                 630                 635                 640

AAT GCA GAA ATT AAA AAG ATA TTT GAG TCA GAT ATG AAG AGA ACG AAA     1968
Asn Ala Glu Ile Lys Lys Ile Phe Glu Ser Asp Met Lys Arg Thr Lys
                645                 650                 655

GAA GAT AAT TAC GGA AGT TTA GAA AAT GAT GCT TTG AAA GGC TAT TTT     2016
Glu Asp Asn Tyr Gly Ser Leu Glu Asn Asp Ala Leu Lys Gly Tyr Phe
            660                 665                 670

GAG AAA TAT TTC CTT ACA CCA TTT AAT AAA ATT AAG CAG ATT GTA GAT     2064
Glu Lys Tyr Phe Leu Thr Pro Phe Asn Lys Ile Lys Gln Ile Val Asp
        675                 680                 685

GAT TTG GAT AAA AAA GTA GAA CAA GAT CAG CCA GCA CCA ATT CCG GAA     2112
Asp Leu Asp Lys Lys Val Glu Gln Asp Gln Pro Ala Pro Ile Pro Glu
    690                 695                 700

AAT TCA GAA ATG GAT CAG GCT AAG GAA AAG GCT AAG ATT GCT GTA TCG     2160
Asn Ser Glu Met Asp Gln Ala Lys Glu Lys Ala Lys Ile Ala Val Ser
705                 710                 715                 720

AAG TAT ATG AGT AAG GTT TTA GAT GGA GTT CAT CAA CAT CTG CAG AAG     2208
Lys Tyr Met Ser Lys Val Leu Asp Gly Val His Gln His Leu Gln Lys
                725                 730                 735

AAA AAT CAC AGT AAA ATT GTT GAT CTT TTT AAG GAA CTT GAA GCG ATT     2256
Lys Asn His Ser Lys Ile Val Asp Leu Phe Lys Glu Leu Glu Ala Ile
            740                 745                 750

AAA CAA CAA ACT ATT TTT GAT ATT GAC AAT GCA AAG ACT GAA GTA GAG     2304
Lys Gln Gln Thr Ile Phe Asp Ile Asp Asn Ala Lys Thr Glu Val Glu
        755                 760                 765

ATT GAT AAC TTA GTA CAC GAT GCA TTC TCA AAA ATG AAT GCT ACT GTT     2352
Ile Asp Asn Leu Val His Asp Ala Phe Ser Lys Met Asn Ala Thr Val
    770                 775                 780

GCT AAA TTT CAA AAA GGT CTA GAG ACA AAT ACG CCA GAA ACT CCA GAT     2400
Ala Lys Phe Gln Lys Gly Leu Glu Thr Asn Thr Pro Glu Thr Pro Asp
785                 790                 795                 800

ACA CCG AAG ATT CCA GAG CTA CCT CAA GCC CCA GAT ACA CCG CAG GCT     2448
```

-continued

```
Thr Pro Lys Ile Pro Glu Leu Pro Gln Ala Pro Asp Thr Pro Gln Ala
                805                 810                 815

CCA GAC ACA CCG CAT GTT CCG GAA TCA CCA AAG GCC CCA GAA GCA CCG     2496
Pro Asp Thr Pro His Val Pro Glu Ser Pro Lys Ala Pro Glu Ala Pro
            820                 825                 830

CGT GTT CCG GAA TCA CCA AAC ACT CCA GAA GCA CCG CAT GTT CCG GAA     2544
Arg Val Pro Glu Ser Pro Asn Thr Pro Glu Ala Pro His Val Pro Glu
        835                 840                 845

TCA CCA AAG GCC CCA GAA CCA CCG CGT GTT CCG GAA TCA CCA AAC ACT     2592
Ser Pro Lys Ala Pro Glu Pro Pro Arg Val Pro Glu Ser Pro Asn Thr
    850                 855                 860

CCA GAA GCA CCG CAT GTT CCG GAA TCA CCA AAG ACT CCA GAA GCA CCA     2640
Pro Glu Ala Pro His Val Pro Glu Ser Pro Lys Thr Pro Glu Ala Pro
865                 870                 875                 880

AAG ATT CCG GAA CCC CCT AAG ACT CCA GAC GTC CCT AAG CTT CCA GAC     2688
Lys Ile Pro Glu Pro Pro Lys Thr Pro Asp Val Pro Lys Leu Pro Asp
                885                 890                 895

GTC CCT AAG CTT CCA CAC GTC CCT AAG CTT CCA GAT GCA CCG AAG TTA     2736
Val Pro Lys Leu Pro His Val Pro Lys Leu Pro Asp Ala Pro Lys Leu
            900                 905                 910

CCA GAT GGG TTA AAT AAA GTT GGA CAA GCA GTA TTT ACA TCA ACT GAT     2784
Pro Asp Gly Leu Asn Lys Val Gly Gln Ala Val Phe Thr Ser Thr Asp
        915                 920                 925

GGA AAT ACT AAG GTT ACG GTT GTA TTT GAT AAA CCT ACA GAT GCT GAT     2832
Gly Asn Thr Lys Val Thr Val Val Phe Asp Lys Pro Thr Asp Ala Asp
    930                 935                 940

AAG TTA CAT CTC AAG GAA CTA ACG ACG AAA GAG TTG GCT GAT AAA ATT     2880
Lys Leu His Leu Lys Glu Leu Thr Thr Lys Glu Leu Ala Asp Lys Ile
945                 950                 955                 960

GCT CAT AAA ACA GGA GGA GGA ACA GTT CGT GTG TTT GAC TTA TCT CTT     2928
Ala His Lys Thr Gly Gly Gly Thr Val Arg Val Phe Asp Leu Ser Leu
                965                 970                 975

TCT AAA GGA GGC AAG GAA ACA CAT GTC AAT GGA GAA CGA ACT GTT CGG     2976
Ser Lys Gly Gly Lys Glu Thr His Val Asn Gly Glu Arg Thr Val Arg
            980                 985                 990

CTC GCG CTT GGG CAG ACT GGC TCA GAT GTT CAC GTC TAT CAC GTA AAG     3024
Leu Ala Leu Gly Gln Thr Gly Ser Asp Val His Val Tyr His Val Lys
        995                 1000                1005

GAA AAT GGC GAC CTT GAG CGT ATT CCT TCT AAA GTT GAA AAT GGG CAA     3072
Glu Asn Gly Asp Leu Glu Arg Ile Pro Ser Lys Val Glu Asn Gly Gln
    1010                1015                1020

GTT GTT TTT AAA ACG AAC CAC TTC AGT TTG TTT GCG ATT AAG ACA CTT     3120
Val Val Phe Lys Thr Asn His Phe Ser Leu Phe Ala Ile Lys Thr Leu
1025                1030                1035                1040

TCT AAG GAT CAA AAT GTT ACT CCA CCG AAG CAG ACT AAA CCT TCT ACC     3168
Ser Lys Asp Gln Asn Val Thr Pro Pro Lys Gln Thr Lys Pro Ser Thr
                1045                1050                1055

CAA GGC AGT CAA GTA GAG ATT GCA GAG AGT CAA ACT GGA AAA TTC CAG     3216
Gln Gly Ser Gln Val Glu Ile Ala Glu Ser Gln Thr Gly Lys Phe Gln
            1060                1065                1070

AGT AAA GCA GCT AAT CAT AAA GCA CTG GCT ACT GGA AAT GAA ACA GTG     3264
Ser Lys Ala Ala Asn His Lys Ala Leu Ala Thr Gly Asn Glu Thr Val
        1075                1080                1085

GCA AAA GGA AAT CCT ACA TCA ACA ACG GAA AAG AAA CTC GAG CAC CAC     3312
Ala Lys Gly Asn Pro Thr Ser Thr Thr Glu Lys Lys Leu Glu His His
    1090                1095                1100
```

(2) INFORMATION FOR SEQ ID NO: 4:

(i) SEQUENCE CHARACTERISTICS:

-continued

```
        (A) LENGTH: 1104 amino acids
        (B) TYPE: amino acid
        (D) TOPOLOGY: linear

    (ii) MOLECULE TYPE: protein

    (xi) SEQUENCE DESCRIPTION: SEQ ID NO: 4:

Glu Gly Asp Ile His Met Ser Glu Leu Val Lys Asp Asp Ser Val Lys
  1               5                  10                  15

Thr Thr Glu Val Ala Ala Lys Pro Tyr Pro Ser Met Ala Gln Thr Asp
             20                  25                  30

Gln Gly Asn Asn Ser Ser Ser Ser Glu Leu Glu Thr Thr Arg Met Glu
         35                  40                  45

Ile Pro Thr Thr His Ile Lys Lys Ala Val Glu Pro Val Glu Lys Thr
     50                  55                  60

Ala Gly Glu Thr Ser Ala Thr Asp Thr Gly Lys Arg Glu Lys Gln Leu
 65                  70                  75                  80

Gln Gln Trp Lys Asn Asn Leu Lys Asn Asp Val Asp Asn Thr Ile Leu
                 85                  90                  95

Ser His Glu Gln Lys Asn Glu Phe Lys Thr Lys Ile Asp Glu Thr Asn
            100                 105                 110

Asp Ser Asp Ala Leu Leu Glu Leu Glu Asn Gln Phe Asn Glu Thr Asn
        115                 120                 125

Arg Leu Leu His Ile Lys Gln His Glu Glu Val Glu Lys His Asn Lys
    130                 135                 140

Pro Asn Gln Gln Lys Thr Leu Lys Gln Ser Asp Thr Lys Val Asp Leu
145                 150                 155                 160

Ser Asn Ile Asp Lys Glu Leu Asn His Gln Lys Ser Gln Val Glu Ala
                165                 170                 175

Met Ala Glu Gln Ala Gly Ile Thr Asn Glu Asp Lys Asp Ser Met Leu
            180                 185                 190

Lys Lys Ile Glu Asp Ile Arg Lys Gln Ala Gln Gln Ala Asp Lys Lys
        195                 200                 205

Glu Asp Ala Glu Val Lys Val Arg Glu Glu Leu Gly Lys Leu Phe Ser
    210                 215                 220

Ser Thr Lys Ala Gly Leu Asp Gln Gln Ile Gln Glu His Val Lys Lys
225                 230                 235                 240

Glu Thr Ser Ser Glu Glu Asn Thr Gln Lys Val Asp Glu His Tyr Ala
                245                 250                 255

Asn Ser Leu Gln Asn Leu Ala Gln Lys Ser Leu Glu Glu Leu Asp Lys
            260                 265                 270

Ala Thr Thr Asn Glu Gln Ala Thr Gln Val Lys Asn Gln Phe Leu Glu
        275                 280                 285

Asn Ala Gln Lys Leu Lys Glu Ile Gln Pro Leu Ile Lys Glu Thr Asn
    290                 295                 300

Val Lys Leu Tyr Lys Ala Met Ser Glu Ser Leu Glu Gln Val Glu Lys
305                 310                 315                 320

Glu Leu Lys His Asn Ser Glu Ala Asn Leu Gln Asp Leu Val Ala Lys
                325                 330                 335

Ser Lys Glu Ile Val Arg Glu Tyr Glu Gly Lys Leu Asn Gln Ser Lys
            340                 345                 350

Asn Leu Pro Glu Leu Lys Gln Leu Glu Glu Glu Ala His Ser Lys Leu
        355                 360                 365

Lys Gln Val Val Glu His Phe Arg Lys Lys Phe Lys Thr Ser Glu Gln
    370                 375                 380
```

-continued

```
Val Thr Pro Lys Lys Arg Val Lys Arg Asp Leu Ala Ala Asn Glu Asn
385                 390                 395                 400

Asn Gln Gln Lys Ile Glu Leu Thr Val Ser Pro Glu Asn Ile Thr Val
                405                 410                 415

Tyr Glu Gly Glu Asp Val Lys Phe Thr Val Thr Ala Lys Ser Asp Ser
            420                 425                 430

Lys Thr Thr Leu Asp Phe Ser Asp Leu Leu Thr Lys Tyr Asn Pro Ser
        435                 440                 445

Val Ser Asp Arg Ile Ser Thr Asn Tyr Lys Thr Asn Thr Asp Asn His
    450                 455                 460

Lys Ile Ala Glu Ile Thr Ile Lys Asn Leu Lys Leu Asn Gln Ser Gln
465                 470                 475                 480

Thr Val Thr Leu Lys Ala Lys Asp Asp Ser Gly Asn Val Val Glu Lys
                485                 490                 495

Thr Phe Thr Ile Thr Val Gln Lys Lys Glu Glu Lys Gln Val Pro Lys
            500                 505                 510

Thr Pro Glu Gln Lys His Ser Lys Thr Glu Gln Asn Val Pro Gln Glu
        515                 520                 525

Pro Lys Ser Asn Asp Lys Asn Gln Leu Gln Glu Leu Ile Lys Ser Ala
    530                 535                 540

Gln Gln Glu Leu Glu Lys Leu Glu Lys Ala Ile Lys Glu Leu Met Glu
545                 550                 555                 560

Gln Pro Glu Ile Pro Ser Asn Pro Glu Tyr Gly Ile Gln Lys Ser Ile
                565                 570                 575

Trp Glu Ser Gln Lys Glu Pro Ile Gln Glu Ala Ile Thr Ser Phe Asn
            580                 585                 590

Lys Ile Ile Gly Asp Ser Ser Ser Lys Tyr Tyr Thr Glu His Tyr Phe
        595                 600                 605

Asn Lys Tyr Lys Ser His Phe Met Asn Tyr Gln Leu His Ala Gln Met
    610                 615                 620

Glu Ile Leu Thr Arg Lys Val Val Gln Tyr Met Asn Lys Tyr Pro Asp
625                 630                 635                 640

Asn Ala Glu Ile Lys Lys Ile Phe Glu Ser Asp Met Lys Arg Thr Lys
                645                 650                 655

Glu Asp Asn Tyr Gly Ser Leu Glu Asn Asp Ala Leu Lys Gly Tyr Phe
            660                 665                 670

Glu Lys Tyr Phe Leu Thr Pro Phe Asn Lys Ile Lys Gln Ile Val Asp
        675                 680                 685

Asp Leu Asp Lys Lys Val Glu Gln Asp Gln Pro Ala Pro Ile Pro Glu
    690                 695                 700

Asn Ser Glu Met Asp Gln Ala Lys Glu Lys Ala Lys Ile Ala Val Ser
705                 710                 715                 720

Lys Tyr Met Ser Lys Val Leu Asp Gly Val His Gln His Leu Gln Lys
                725                 730                 735

Lys Asn His Ser Lys Ile Val Asp Leu Phe Lys Glu Leu Glu Ala Ile
            740                 745                 750

Lys Gln Gln Thr Ile Phe Asp Ile Asp Asn Ala Lys Thr Glu Val Glu
        755                 760                 765

Ile Asp Asn Leu Val His Asp Ala Phe Ser Lys Met Asn Ala Thr Val
    770                 775                 780

Ala Lys Phe Gln Lys Gly Leu Glu Thr Asn Thr Pro Glu Thr Pro Asp
785                 790                 795                 800
```

-continued

```
Thr Pro Lys Ile Pro Glu Leu Pro Gln Ala Pro Asp Thr Pro Gln Ala
                805                 810                 815

Pro Asp Thr Pro His Val Pro Glu Ser Pro Lys Ala Pro Glu Ala Pro
            820                 825                 830

Arg Val Pro Glu Ser Pro Asn Thr Pro Glu Ala Pro His Val Pro Glu
        835                 840                 845

Ser Pro Lys Ala Pro Glu Pro Pro Arg Val Pro Glu Ser Pro Asn Thr
    850                 855                 860

Pro Glu Ala Pro His Val Pro Glu Ser Pro Lys Thr Pro Glu Ala Pro
865                 870                 875                 880

Lys Ile Pro Glu Pro Pro Lys Thr Pro Asp Val Pro Lys Leu Pro Asp
                885                 890                 895

Val Pro Lys Leu Pro His Val Pro Lys Leu Pro Asp Ala Pro Lys Leu
            900                 905                 910

Pro Asp Gly Leu Asn Lys Val Gly Gln Ala Val Phe Thr Ser Thr Asp
        915                 920                 925

Gly Asn Thr Lys Val Thr Val Val Phe Asp Lys Pro Thr Asp Ala Asp
    930                 935                 940

Lys Leu His Leu Lys Glu Leu Thr Thr Lys Glu Leu Ala Asp Lys Ile
945                 950                 955                 960

Ala His Lys Thr Gly Gly Gly Thr Val Arg Val Phe Asp Leu Ser Leu
                965                 970                 975

Ser Lys Gly Gly Lys Glu Thr His Val Asn Gly Glu Arg Thr Val Arg
            980                 985                 990

Leu Ala Leu Gly Gln Thr Gly Ser Asp Val His Val Tyr His Val Lys
        995                 1000                1005

Glu Asn Gly Asp Leu Glu Arg Ile Pro Ser Lys Val Glu Asn Gly Gln
    1010                1015                1020

Val Val Phe Lys Thr Asn His Phe Ser Leu Phe Ala Ile Lys Thr Leu
1025                1030                1035                1040

Ser Lys Asp Gln Asn Val Thr Pro Pro Lys Gln Thr Lys Pro Ser Thr
                1045                1050                1055

Gln Gly Ser Gln Val Glu Ile Ala Glu Ser Gln Thr Gly Lys Phe Gln
            1060                1065                1070

Ser Lys Ala Ala Asn His Lys Ala Leu Ala Thr Gly Asn Glu Thr Val
        1075                1080                1085

Ala Lys Gly Asn Pro Thr Ser Thr Thr Glu Lys Lys Leu Glu His His
    1090                1095                1100
```

(2) INFORMATION FOR SEQ ID NO: 5:

(i) SEQUENCE CHARACTERISTICS:
(A) LENGTH: 3384 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..3384

(xi) SEQUENCE DESCRIPTION: SEQ ID NO: 5:

```
ATG AGT GAG CTT GTA AAG GAC GAT AGT GTG AAG ACT ACC GAG GTT GCA       48
Met Ser Glu Leu Val Lys Asp Asp Ser Val Lys Thr Thr Glu Val Ala
  1               5                  10                  15

GCT AAG CCC TAT CCA AGT ATG GCT CAA ACA GAT CAA GGA AAT AAT TCA       96
```

-continued

```
Ala Lys Pro Tyr Pro Ser Met Ala Gln Thr Asp Gln Gly Asn Asn Ser
            20                  25                  30

TCA TCC TCG GAA CTT GAG ACA ACA AGG ATG GAA ATT CCT ACA ACA GAC      144
Ser Ser Ser Glu Leu Glu Thr Thr Arg Met Glu Ile Pro Thr Thr Asp
        35                  40                  45

ATA AAA AAA GCT GTT GAA CCG GTC GAG AAA ACA GCT GGG GAA ACA TCT      192
Ile Lys Lys Ala Val Glu Pro Val Glu Lys Thr Ala Gly Glu Thr Ser
    50                  55                  60

GCC ACT GAT ACT GGA AAA CGA GAG AAA CAA TTA CAA CAA TGG AAA AAT      240
Ala Thr Asp Thr Gly Lys Arg Glu Lys Gln Leu Gln Gln Trp Lys Asn
 65                  70                  75                  80

AAT CTA AAA AAT GAT GTG GAT AAC ACA ATT CTA TCT CAT GAA CAG AAA      288
Asn Leu Lys Asn Asp Val Asp Asn Thr Ile Leu Ser His Glu Gln Lys
                85                  90                  95

AAT GAG TTT AAA ACA AAA ATT GAT GAA ACA AAT GAT TCT GAT GCA TTA      336
Asn Glu Phe Lys Thr Lys Ile Asp Glu Thr Asn Asp Ser Asp Ala Leu
            100                 105                 110

TTA GAA TTA GAA AAT CAA TTT AAC GAA ACT AAT AGA CTG TTA CAC ATC      384
Leu Glu Leu Glu Asn Gln Phe Asn Glu Thr Asn Arg Leu Leu His Ile
        115                 120                 125

AAA CAA CAT GAA GAA GTT GAG AAA GAT AAG AAA GCT AAG CAA CAG AAA      432
Lys Gln His Glu Glu Val Glu Lys Asp Lys Lys Ala Lys Gln Gln Lys
    130                 135                 140

ACT CTG AAA CAG TCA GAT ACG AAA GTA GAT CTA AGC AAT ATT GAC AAA      480
Thr Leu Lys Gln Ser Asp Thr Lys Val Asp Leu Ser Asn Ile Asp Lys
145                 150                 155                 160

GAG CTT AAT CAT CAA AAA AGT CCA GTT GAA AAA ATG GCA GAG CCA AAG      528
Glu Leu Asn His Gln Lys Ser Pro Val Glu Lys Met Ala Glu Pro Lys
                165                 170                 175

GGA ATC ACA AAT GAA GAT AAA GAT TCT ATG CTG AAA AAA ATC GAA GAT      576
Gly Ile Thr Asn Glu Asp Lys Asp Ser Met Leu Lys Lys Ile Glu Asp
            180                 185                 190

ATT CGT AAA CAA GCT CAA CAA GCA GAT AAA AAA GAA GAT GCC GAA GTA      624
Ile Arg Lys Gln Ala Gln Gln Ala Asp Lys Lys Glu Asp Ala Glu Val
        195                 200                 205

AAG GTT CGT GAA GAA CTA GGT AAA CTC TTT AGT TCA ACT AAA GCT GGT      672
Lys Val Arg Glu Glu Leu Gly Lys Leu Phe Ser Ser Thr Lys Ala Gly
    210                 215                 220

CTG GAT CAA GAA ATT CAT GAG CAT GTG AAG AAA GAA ACG AGT AGT GAG      720
Leu Asp Gln Glu Ile His Glu His Val Lys Lys Glu Thr Ser Ser Glu
225                 230                 235                 240

GAA AAT ACT CAG AAA GTT GAT GAA CAC TAT GCT AAT AGC CTT CAG AAC      768
Glu Asn Thr Gln Lys Val Asp Glu His Tyr Ala Asn Ser Leu Gln Asn
                245                 250                 255

CTT GCT CAA AAA TCT CTT GAA GAA CTA GAT AAG GCA ACT ACC AAT GAA      816
Leu Ala Gln Lys Ser Leu Glu Glu Leu Asp Lys Ala Thr Thr Asn Glu
            260                 265                 270

CAA GCT ACA CAA GTT AAA AAT CAA TTC TTA GAA AAC GCT CAA AAG CTC      864
Gln Ala Thr Gln Val Lys Asn Gln Phe Leu Glu Asn Ala Gln Lys Leu
        275                 280                 285

AAA GAA ATG CAA CCT CTT ATC AAA GAA ACG AAT GTG AAA TTG TAT AAG      912
Lys Glu Met Gln Pro Leu Ile Lys Glu Thr Asn Val Lys Leu Tyr Lys
    290                 295                 300

GCT ATG AGT GAG AGC TTG GAG CAG GTT GAG AAG GAA TTA AAA CAT AAT      960
Ala Met Ser Glu Ser Leu Glu Gln Val Glu Lys Glu Leu Lys His Asn
305                 310                 315                 320

TCG GAA GCT AAT TTA GAA GAT TTG GTT GCG AAA TCT AAA GAA ATC GTA     1008
Ser Glu Ala Asn Leu Glu Asp Leu Val Ala Lys Ser Lys Glu Ile Val
                325                 330                 335
```

-continued

```
AGA GAA TAC GAA GGA AAA CTT AAT CAA TCT AAA AAT CTT CCA GAA TTA      1056
Arg Glu Tyr Glu Gly Lys Leu Asn Gln Ser Lys Asn Leu Pro Glu Leu
            340                 345                 350

AAG CAA CTA GAA GAG GAA GCT CAT TCG AAG TTG AAA CAA GTT GTG GAG      1104
Lys Gln Leu Glu Glu Glu Ala His Ser Lys Leu Lys Gln Val Val Glu
        355                 360                 365

GAT TTT AGA AAA AAA TTT AAA ACG TCA GAG CAA GTG ACA CCA AAA AAA      1152
Asp Phe Arg Lys Lys Phe Lys Thr Ser Glu Gln Val Thr Pro Lys Lys
    370                 375                 380

CGT GTC AAA CGA GAT TTA GCT GCT AAT GAA AAT AAT CAA CAA AAG ATT      1200
Arg Val Lys Arg Asp Leu Ala Ala Asn Glu Asn Asn Gln Gln Lys Ile
385                 390                 395                 400

GAG TTA ACA GTT TCA CCA GAG AAT ATC ACT GTA TAT GAA GGT GAA GAC      1248
Glu Leu Thr Val Ser Pro Glu Asn Ile Thr Val Tyr Glu Gly Glu Asp
                405                 410                 415

GTG AAA TTT ACA GTC ACA GCT AAA AGT GAT TCG AAG ACG ACG TTG GAC      1296
Val Lys Phe Thr Val Thr Ala Lys Ser Asp Ser Lys Thr Thr Leu Asp
            420                 425                 430

TTC AGT GAT CTT TTA ACA AAA TAT AAT CCG TCT GTA TCA GAT AGA ATT      1344
Phe Ser Asp Leu Leu Thr Lys Tyr Asn Pro Ser Val Ser Asp Arg Ile
        435                 440                 445

AGT ACA AAT TAT AAG ACT AAC ACG GAT AAT CAT AAG ATT GCC GAA ATC      1392
Ser Thr Asn Tyr Lys Thr Asn Thr Asp Asn His Lys Ile Ala Glu Ile
    450                 455                 460

ACT ATC AAG AAT TTG AAG CTA AAT GAA AGT CAA ACA GTG ACT CTA AAA      1440
Thr Ile Lys Asn Leu Lys Leu Asn Glu Ser Gln Thr Val Thr Leu Lys
465                 470                 475                 480

GCT AAA GAT GAT TCT GGC AAT GTA GTT GAA AAA ACA TTC ACT ATT ACA      1488
Ala Lys Asp Asp Ser Gly Asn Val Val Glu Lys Thr Phe Thr Ile Thr
                485                 490                 495

GTG CAA AAG AAA GAG GAG AAA CAA GTT CCT AAA ACA CCA GAG CAG AAA      1536
Val Gln Lys Lys Glu Glu Lys Gln Val Pro Lys Thr Pro Glu Gln Lys
            500                 505                 510

GAT TCT AAA ACG GAA GAA AAG GTT CCT CAA GAA CCA AAA TCA AAT GAC      1584
Asp Ser Lys Thr Glu Glu Lys Val Pro Gln Glu Pro Lys Ser Asn Asp
        515                 520                 525

AAG AAT CAA TTA CAA GAG TTG ATT AAA TCA GCT CAA CAA GAA CTG GAA      1632
Lys Asn Gln Leu Gln Glu Leu Ile Lys Ser Ala Gln Gln Glu Leu Glu
    530                 535                 540

AAG TTA GAA AAA GCA ATA AAA GAA TTA ATG GAG CAA CCA GAG ATT CCA      1680
Lys Leu Glu Lys Ala Ile Lys Glu Leu Met Glu Gln Pro Glu Ile Pro
545                 550                 555                 560

TCC AAT CCA GAG TAT GGT ATT CAA AAA TCT ATT TGG GAG TCA CAA AAA      1728
Ser Asn Pro Glu Tyr Gly Ile Gln Lys Ser Ile Trp Glu Ser Gln Lys
                565                 570                 575

GAG CCT ATC CAG GAA GCC ATA ACA AGT TTT AAG AAG ATT ATT GGT GAT      1776
Glu Pro Ile Gln Glu Ala Ile Thr Ser Phe Lys Lys Ile Ile Gly Asp
            580                 585                 590

TCA TCT TCA AAA TAC TAC ACA GAG CAC TAT TTT AAC AAA TAT AAA TCT      1824
Ser Ser Ser Lys Tyr Tyr Thr Glu His Tyr Phe Asn Lys Tyr Lys Ser
        595                 600                 605

GAT TTT ATG AAT TAT CAA CTT CAT GCA CAA ATG GAG ATG CTG ACT AGA      1872
Asp Phe Met Asn Tyr Gln Leu His Ala Gln Met Glu Met Leu Thr Arg
    610                 615                 620

AAA GTG GTT CAG TAT ATG AAC AAA TAT CCT GAT AAT GCA GAA ATT AAA      1920
Lys Val Val Gln Tyr Met Asn Lys Tyr Pro Asp Asn Ala Glu Ile Lys
625                 630                 635                 640

AAG ATA TTT GAG TCA GAT ATG AAG AGA ACG AAA GAA GAT AAT TAC GGA      1968
Lys Ile Phe Glu Ser Asp Met Lys Arg Thr Lys Glu Asp Asn Tyr Gly
                645                 650                 655
```

-continued

```
AGT TTA GAA AAT GAT GCT TTG AAA GGC TAT TTT GAG AAA TAT TTC CTT     2016
Ser Leu Glu Asn Asp Ala Leu Lys Gly Tyr Phe Glu Lys Tyr Phe Leu
            660                 665                 670

ACA CCA TTT AAT AAA ATT AAG CAG ATT GTA GAT GAT TTG GAT AAA AAA     2064
Thr Pro Phe Asn Lys Ile Lys Gln Ile Val Asp Asp Leu Asp Lys Lys
        675                 680                 685

GTA GAA CAA GAT CAG CCA GCA CCA ATT CCG GAA AAT TCA GAA ATG GAT     2112
Val Glu Gln Asp Gln Pro Ala Pro Ile Pro Glu Asn Ser Glu Met Asp
    690                 695                 700

CAG GCT AAG GAA AAG GCT AAG ATT GCT GTA TCG AAG TAT ATG AGT AAG     2160
Gln Ala Lys Glu Lys Ala Lys Ile Ala Val Ser Lys Tyr Met Ser Lys
705                 710                 715                 720

GTT TTA GAT GGA GTT CAT CAA CAT CTG CAG AAG AAA AAT CAC AGT AAA     2208
Val Leu Asp Gly Val His Gln His Leu Gln Lys Lys Asn His Ser Lys
                725                 730                 735

ATT GTT GAT CTT TTT AAG GAA CTT GAA GCG ATT AAA CAA CAA ACT ATT     2256
Ile Val Asp Leu Phe Lys Glu Leu Glu Ala Ile Lys Gln Gln Thr Ile
            740                 745                 750

TTT GAT ATT GAC AAT GCA AAG ACT GAA GTA GAG ATT GAT AAC TTA GTA     2304
Phe Asp Ile Asp Asn Ala Lys Thr Glu Val Glu Ile Asp Asn Leu Val
        755                 760                 765

CAC GAT GCA TTC TCA AAA ATG AAT GCT ACT GTT GCT AAA TTT CAA AAA     2352
His Asp Ala Phe Ser Lys Met Asn Ala Thr Val Ala Lys Phe Gln Lys
    770                 775                 780

GGT CTA GAG ACA AAT ACG CCA GAA ACT CCA GAT ACA CCG AAG ATT CCA     2400
Gly Leu Glu Thr Asn Thr Pro Glu Thr Pro Asp Thr Pro Lys Ile Pro
785                 790                 795                 800

GAG CTA CCT CAA GCC CCA GAT ACA CCG CAG GCT CCA GAC ACA CCG CAT     2448
Glu Leu Pro Gln Ala Pro Asp Thr Pro Gln Ala Pro Asp Thr Pro His
                805                 810                 815

GTT CCG GAA TCA CCA AAG GCC CCA GAA GCA CCG CGT GTT CCG GAA TCA     2496
Val Pro Glu Ser Pro Lys Ala Pro Glu Ala Pro Arg Val Pro Glu Ser
            820                 825                 830

CCA AAG ACT CCA GAA GCA CCG CAT GTT CCG GAA TCA CCA AAG GCC CCA     2544
Pro Lys Thr Pro Glu Ala Pro His Val Pro Glu Ser Pro Lys Ala Pro
        835                 840                 845

GAA GCA CCG CGT GTT CCG GAA TCA CCA AAG ACT CCA GAA GCA CCG CAT     2592
Glu Ala Pro Arg Val Pro Glu Ser Pro Lys Thr Pro Glu Ala Pro His
    850                 855                 860

GTT CCG GAA TCA CCA AAG ACT CCA GAA GCA CCA AAG ATT CCG GAA CCC     2640
Val Pro Glu Ser Pro Lys Thr Pro Glu Ala Pro Lys Ile Pro Glu Pro
865                 870                 875                 880

CCT AAG ACT CCG GAC GTC CCT AAG CTT CCA GAC GTC CCT AAG CTT CCA     2688
Pro Lys Thr Pro Asp Val Pro Lys Leu Pro Asp Val Pro Lys Leu Pro
                885                 890                 895

GAC GTC CCT AAG CTT CCA GAT GCA CCG AAG TTA CCA GAT GGG TTA AAT     2736
Asp Val Pro Lys Leu Pro Asp Ala Pro Lys Leu Pro Asp Gly Leu Asn
            900                 905                 910

AAA GTT GGA CAA GCA GTA TTT ACA TCA ACT GAT GGA AAT ACT AAG GTT     2784
Lys Val Gly Gln Ala Val Phe Thr Ser Thr Asp Gly Asn Thr Lys Val
        915                 920                 925

ACG GTT GTA TTT GAT AAA CCT ACA GAT GCT GAT AAG TTA CAT CTC AAG     2832
Thr Val Val Phe Asp Lys Pro Thr Asp Ala Asp Lys Leu His Leu Lys
    930                 935                 940

GAA GTA ACG ACG AAA GAG TTG GCT GAT AAA ATT GCT CAT AAA ACA GGA     2880
Glu Val Thr Thr Lys Glu Leu Ala Asp Lys Ile Ala His Lys Thr Gly
945                 950                 955                 960

GGA GGA ACA GTT CGT GTG TTT GAC TTA TCT CTT TCT AAA GGA GGC AAG     2928
Gly Gly Thr Val Arg Val Phe Asp Leu Ser Leu Ser Lys Gly Gly Lys
```

-continued

```
                965                 970                 975

GAA ACA CAT GTC AAT GGA GAA CGA ACT GTT CGG CTC GCG CTT GGG CAG      2976
Glu Thr His Val Asn Gly Glu Arg Thr Val Arg Leu Ala Leu Gly Gln
            980                 985                 990

ACT GGC TCA GAT GTT CAC GTC TAT CAC GTA AAG GAA AAT GGC GAC CTT      3024
Thr Gly Ser Asp Val His Val Tyr His Val Lys Glu Asn Gly Asp Leu
        995                1000                1005

GAG CGT ATT CCT TCT AAA GTT GAA AAT GGG CAA GTT GTT TTT AAA ACG      3072
Glu Arg Ile Pro Ser Lys Val Glu Asn Gly Gln Val Val Phe Lys Thr
    1010                1015                1020

AAC CAC TTC AGT TTG TTT GCG ATT AAG ACA CTT TCT AAG GAT CAA AAT      3120
Asn His Phe Ser Leu Phe Ala Ile Lys Thr Leu Ser Lys Asp Gln Asn
1025                1030                1035                1040

GTT ACT CCA CCG AAG CAG ACT AAA CCT TCT ACC CAA GGC AGT CAA GTA      3168
Val Thr Pro Pro Lys Gln Thr Lys Pro Ser Thr Gln Gly Ser Gln Val
                1045                1050                1055

GAG ATT GCA GAG AGT CAA ACT GGA AAA TTC CAG AGT AAA GCA GCT AAT      3216
Glu Ile Ala Glu Ser Gln Thr Gly Lys Phe Gln Ser Lys Ala Ala Asn
            1060                1065                1070

CAT AAA GCA CTG GCT ACT GGA AAT GAA ACA GTG GCA AAA GGA AAT CCT      3264
His Lys Ala Leu Ala Thr Gly Asn Glu Thr Val Ala Lys Gly Asn Pro
        1075                1080                1085

ACA TCA ACA ACG GAA AAG AAA TTG CCA TAT ACA GGA GTG GCA TCT AAT      3312
Thr Ser Thr Thr Glu Lys Lys Leu Pro Tyr Thr Gly Val Ala Ser Asn
    1090                1095                1100

CTA GTT CTT GAA ATT ATG GGT CTC CTT GGT TTG ATT GGA ACT TCA TTC      3360
Leu Val Leu Glu Ile Met Gly Leu Leu Gly Leu Ile Gly Thr Ser Phe
1105                1110                1115                1120

ATC GCA ATG AAA AGA AGA AAA TCA                                      3384
Ile Ala Met Lys Arg Arg Lys Ser
                1125
```

(2) INFORMATION FOR SEQ ID NO: 6:

(i) SEQUENCE CHARACTERISTICS:
(A) LENGTH: 1128 amino acids
(B) TYPE: amino acid
(D) TOPOLOGY: linear (ii) MOLECULE TYPE: protein (xi) SEQUENCE DESCRIPTION: SEQ ID NO: 6:

```
Met Ser Glu Leu Val Lys Asp Asp Ser Val Lys Thr Thr Glu Val Ala
  1               5                  10                  15

Ala Lys Pro Tyr Pro Ser Met Ala Gln Thr Asp Gln Gly Asn Asn Ser
            20                  25                  30

Ser Ser Ser Glu Leu Glu Thr Thr Arg Met Glu Ile Pro Thr Thr Asp
        35                  40                  45

Ile Lys Lys Ala Val Glu Pro Val Glu Lys Thr Ala Gly Glu Thr Ser
     50                  55                  60

Ala Thr Asp Thr Gly Lys Arg Glu Lys Gln Leu Gln Gln Trp Lys Asn
 65                  70                  75                  80

Asn Leu Lys Asn Asp Val Asp Asn Thr Ile Leu Ser His Glu Gln Lys
                 85                  90                  95

Asn Glu Phe Lys Thr Lys Ile Asp Glu Thr Asn Asp Ser Asp Ala Leu
            100                 105                 110

Leu Glu Leu Glu Asn Gln Phe Asn Glu Thr Asn Arg Leu Leu His Ile
        115                 120                 125

Lys Gln His Glu Glu Val Glu Lys Asp Lys Lys Ala Lys Gln Gln Lys
```

-continued

```
    130                 135                 140

Thr Leu Lys Gln Ser Asp Thr Lys Val Asp Leu Ser Asn Ile Asp Lys
145                 150                 155                 160

Glu Leu Asn His Gln Lys Ser Pro Val Glu Lys Met Ala Glu Pro Lys
                165                 170                 175

Gly Ile Thr Asn Glu Asp Lys Asp Ser Met Leu Lys Lys Ile Glu Asp
            180                 185                 190

Ile Arg Lys Gln Ala Gln Gln Ala Asp Lys Lys Glu Asp Ala Glu Val
        195                 200                 205

Lys Val Arg Glu Glu Leu Gly Lys Leu Phe Ser Ser Thr Lys Ala Gly
    210                 215                 220

Leu Asp Gln Glu Ile His Glu His Val Lys Lys Glu Thr Ser Ser Glu
225                 230                 235                 240

Glu Asn Thr Gln Lys Val Asp Glu His Tyr Ala Asn Ser Leu Gln Asn
                245                 250                 255

Leu Ala Gln Lys Ser Leu Glu Glu Leu Asp Lys Ala Thr Thr Asn Glu
            260                 265                 270

Gln Ala Thr Gln Val Lys Asn Gln Phe Leu Glu Asn Ala Gln Lys Leu
        275                 280                 285

Lys Glu Met Gln Pro Leu Ile Lys Glu Thr Asn Val Lys Leu Tyr Lys
    290                 295                 300

Ala Met Ser Glu Ser Leu Glu Gln Val Glu Lys Glu Leu Lys His Asn
305                 310                 315                 320

Ser Glu Ala Asn Leu Glu Asp Leu Val Ala Lys Ser Lys Glu Ile Val
                325                 330                 335

Arg Glu Tyr Glu Gly Lys Leu Asn Gln Ser Lys Asn Leu Pro Glu Leu
            340                 345                 350

Lys Gln Leu Glu Glu Glu Ala His Ser Lys Leu Lys Gln Val Val Glu
        355                 360                 365

Asp Phe Arg Lys Lys Phe Lys Thr Ser Glu Gln Val Thr Pro Lys Lys
    370                 375                 380

Arg Val Lys Arg Asp Leu Ala Ala Asn Glu Asn Asn Gln Gln Lys Ile
385                 390                 395                 400

Glu Leu Thr Val Ser Pro Glu Asn Ile Thr Val Tyr Glu Gly Glu Asp
                405                 410                 415

Val Lys Phe Thr Val Thr Ala Lys Ser Asp Ser Lys Thr Thr Leu Asp
            420                 425                 430

Phe Ser Asp Leu Leu Thr Lys Tyr Asn Pro Ser Val Ser Asp Arg Ile
        435                 440                 445

Ser Thr Asn Tyr Lys Thr Asn Thr Asp Asn His Lys Ile Ala Glu Ile
    450                 455                 460

Thr Ile Lys Asn Leu Lys Leu Asn Glu Ser Gln Thr Val Thr Leu Lys
465                 470                 475                 480

Ala Lys Asp Asp Ser Gly Asn Val Val Glu Lys Thr Phe Thr Ile Thr
                485                 490                 495

Val Gln Lys Lys Glu Glu Lys Gln Val Pro Lys Thr Pro Glu Gln Lys
            500                 505                 510

Asp Ser Lys Thr Glu Glu Lys Val Pro Gln Glu Pro Lys Ser Asn Asp
        515                 520                 525

Lys Asn Gln Leu Gln Glu Leu Ile Lys Ser Ala Gln Gln Glu Leu Glu
    530                 535                 540

Lys Leu Glu Lys Ala Ile Lys Glu Leu Met Glu Gln Pro Glu Ile Pro
545                 550                 555                 560
```

-continued

```
Ser Asn Pro Glu Tyr Gly Ile Gln Lys Ser Ile Trp Glu Ser Gln Lys
            565                 570                 575

Glu Pro Ile Gln Glu Ala Ile Thr Ser Phe Lys Lys Ile Ile Gly Asp
        580                 585                 590

Ser Ser Ser Lys Tyr Tyr Thr Glu His Tyr Phe Asn Lys Tyr Lys Ser
    595                 600                 605

Asp Phe Met Asn Tyr Gln Leu His Ala Gln Met Glu Met Leu Thr Arg
    610                 615                 620

Lys Val Val Gln Tyr Met Asn Lys Tyr Pro Asp Asn Ala Glu Ile Lys
625                 630                 635                 640

Lys Ile Phe Glu Ser Asp Met Lys Arg Thr Lys Glu Asp Asn Tyr Gly
            645                 650                 655

Ser Leu Glu Asn Asp Ala Leu Lys Gly Tyr Phe Glu Lys Tyr Phe Leu
        660                 665                 670

Thr Pro Phe Asn Lys Ile Lys Gln Ile Val Asp Asp Leu Asp Lys Lys
    675                 680                 685

Val Glu Gln Asp Gln Pro Ala Pro Ile Pro Glu Asn Ser Glu Met Asp
    690                 695                 700

Gln Ala Lys Glu Lys Ala Lys Ile Ala Val Ser Lys Tyr Met Ser Lys
705                 710                 715                 720

Val Leu Asp Gly Val His Gln His Leu Gln Lys Lys Asn His Ser Lys
            725                 730                 735

Ile Val Asp Leu Phe Lys Glu Leu Glu Ala Ile Lys Gln Gln Thr Ile
        740                 745                 750

Phe Asp Ile Asp Asn Ala Lys Thr Glu Val Glu Ile Asp Asn Leu Val
    755                 760                 765

His Asp Ala Phe Ser Lys Met Asn Ala Thr Val Ala Lys Phe Gln Lys
    770                 775                 780

Gly Leu Glu Thr Asn Thr Pro Glu Thr Pro Asp Thr Pro Lys Ile Pro
785                 790                 795                 800

Glu Leu Pro Gln Ala Pro Asp Thr Pro Gln Ala Pro Asp Thr Pro His
            805                 810                 815

Val Pro Glu Ser Pro Lys Ala Pro Glu Ala Pro Arg Val Pro Glu Ser
        820                 825                 830

Pro Lys Thr Pro Glu Ala Pro His Val Pro Glu Ser Pro Lys Ala Pro
    835                 840                 845

Glu Ala Pro Arg Val Pro Glu Ser Pro Lys Thr Pro Glu Ala Pro His
    850                 855                 860

Val Pro Glu Ser Pro Lys Thr Pro Glu Ala Pro Lys Ile Pro Glu Pro
865                 870                 875                 880

Pro Lys Thr Pro Asp Val Pro Lys Leu Pro Asp Val Pro Lys Leu Pro
            885                 890                 895

Asp Val Pro Lys Leu Pro Asp Ala Pro Lys Leu Pro Asp Gly Leu Asn
        900                 905                 910

Lys Val Gly Gln Ala Val Phe Thr Ser Thr Asp Gly Asn Thr Lys Val
    915                 920                 925

Thr Val Val Phe Asp Lys Pro Thr Asp Ala Asp Lys Leu His Leu Lys
    930                 935                 940

Glu Val Thr Thr Lys Glu Leu Ala Asp Lys Ile Ala His Lys Thr Gly
945                 950                 955                 960

Gly Gly Thr Val Arg Val Phe Asp Leu Ser Leu Ser Lys Gly Gly Lys
            965                 970                 975
```

-continued

```
Glu Thr His Val Asn Gly Glu Arg Thr Val Arg Leu Ala Leu Gly Gln
            980                 985                 990

Thr Gly Ser Asp Val His Val Tyr His Val Lys Glu Asn Gly Asp Leu
        995                1000                1005

Glu Arg Ile Pro Ser Lys Val Glu Asn Gly Gln Val Val Phe Lys Thr
    1010                1015                1020

Asn His Phe Ser Leu Phe Ala Ile Lys Thr Leu Ser Lys Asp Gln Asn
1025                1030                1035                1040

Val Thr Pro Pro Lys Gln Thr Lys Pro Ser Thr Gln Gly Ser Gln Val
                1045                1050                1055

Glu Ile Ala Glu Ser Gln Thr Gly Lys Phe Gln Ser Lys Ala Ala Asn
            1060                1065                1070

His Lys Ala Leu Ala Thr Gly Asn Glu Thr Val Ala Lys Gly Asn Pro
        1075                1080                1085

Thr Ser Thr Thr Glu Lys Lys Leu Pro Tyr Thr Gly Val Ala Ser Asn
    1090                1095                1100

Leu Val Leu Glu Ile Met Gly Leu Leu Gly Leu Ile Gly Thr Ser Phe
1105                1110                1115                1120

Ile Ala Met Lys Arg Arg Lys Ser
                1125
```

(2) INFORMATION FOR SEQ ID NO: 7:

(i) SEQUENCE CHARACTERISTICS:
- (A) LENGTH: 3294 base pairs
- (B) TYPE: nucleic acid
- (C) STRANDEDNESS: double
- (D) TOPOLOGY: linear (ii) MOLECULE TYPE: cDNA (ix) FEATURE:
- (A) NAME/KEY: CDS
- (B) LOCATION: 1..3294

(xi) SEQUENCE DESCRIPTION: SEQ ID NO: 7:

```
GAA GGA GAT ATA CAT ATG AGT GAG CTT GTA AAG GAC GAT AGT GTG AAG       48
Glu Gly Asp Ile His Met Ser Glu Leu Val Lys Asp Asp Ser Val Lys
  1               5                  10                  15

ACT ACC GAG GTT GCA GCT AAG CCC TAT CCA AGT ATG GCT CAA ACA GAT       96
Thr Thr Glu Val Ala Ala Lys Pro Tyr Pro Ser Met Ala Gln Thr Asp
             20                  25                  30

CAA GGA AAT AAT TCA TCA TCC TCG GAA CTT GAG ACA ACA AGG ATG GAA      144
Gln Gly Asn Asn Ser Ser Ser Ser Glu Leu Glu Thr Thr Arg Met Glu
         35                  40                  45

ATT CCT ACA ACA GAC ATA AAA AAA GCT GTT GAA CCG GTC GAG AAA ACA      192
Ile Pro Thr Thr Asp Ile Lys Lys Ala Val Glu Pro Val Glu Lys Thr
     50                  55                  60

GCT GGG GAA ACA TCT GCC ACT CAT ACT GGA AAA CGA GAG AAA CAA TTA      240
Ala Gly Glu Thr Ser Ala Thr His Thr Gly Lys Arg Glu Lys Gln Leu
 65                  70                  75                  80

CAA CAA TGG AAA AAT AAT CTA AAA AAT GAT GTG GAT AAC ACA ATT CTA      288
Gln Gln Trp Lys Asn Asn Leu Lys Asn Asp Val Asp Asn Thr Ile Leu
                 85                  90                  95

TCT CAT GAA CAG AAA AAT GAG TTT AAA ACA AAA ATT GAT GAA ACA AAT      336
Ser His Glu Gln Lys Asn Glu Phe Lys Thr Lys Ile Asp Glu Thr Asn
            100                 105                 110

GAT TCT GAT GCA TTA TTA GAA TTA GAA AAT CAA TTT AAC GAA ACT AAT      384
Asp Ser Asp Ala Leu Leu Glu Leu Glu Asn Gln Phe Asn Glu Thr Asn
        115                 120                 125
```

-continued

```
AGA CTG TTA CAC ATC AAA CAA CAT GAA GAA GTT GAG AAA GAT AAG AAA      432
Arg Leu Leu His Ile Lys Gln His Glu Glu Val Glu Lys Asp Lys Lys
    130                 135                 140

GCT AAG CAA CAG AAA ACT CTG AAA CAG TCA GAT ACG AAA GTA GAT CTA      480
Ala Lys Gln Gln Lys Thr Leu Lys Gln Ser Asp Thr Lys Val Asp Leu
145                 150                 155                 160

AGC AAT ATT GAC AAA GAG CTT AAT CAT CAA AAA AGT CAA GAA GCG GGA      528
Ser Asn Ile Asp Lys Glu Leu Asn His Gln Lys Ser Gln Glu Ala Gly
                165                 170                 175

ATC ACA AAT GAA GAT AAA GAT TCT ATG CTG AAA AAA ATC GAA GAT ATT      576
Ile Thr Asn Glu Asp Lys Asp Ser Met Leu Lys Lys Ile Glu Asp Ile
            180                 185                 190

CGT AAA CAA GCT CAA CAA CCA GAT AAA AAA GAA GAT GCC GAA GTA AAG      624
Arg Lys Gln Ala Gln Gln Pro Asp Lys Lys Glu Asp Ala Glu Val Lys
        195                 200                 205

GTT CGT GAA GAA CTA GGT AAA CTC TTT AGT TCA ACT AAA GCT GGT CTG      672
Val Arg Glu Glu Leu Gly Lys Leu Phe Ser Ser Thr Lys Ala Gly Leu
    210                 215                 220

GAT CAA GAA ATT CAA GAG CAT GTG AAG AAA GAA ACG AGT AGT GAG GAA      720
Asp Gln Glu Ile Gln Glu His Val Lys Lys Glu Thr Ser Ser Glu Glu
225                 230                 235                 240

AAT ACT CAG AAA GTT GAT GAA CAC TAT GCT AAT AGC CTT CAG AAC CTT      768
Asn Thr Gln Lys Val Asp Glu His Tyr Ala Asn Ser Leu Gln Asn Leu
                245                 250                 255

GCT CAA AAA TCT CTT GAA GAA CTA GAT AAG GCA ACT ACC AAT GAA CAA      816
Ala Gln Lys Ser Leu Glu Glu Leu Asp Lys Ala Thr Thr Asn Glu Gln
            260                 265                 270

GCT ACA CAA GTT AAA AAT CAA TTC TTA GAA AAC GCT CAA AAG CTC AAA      864
Ala Thr Gln Val Lys Asn Gln Phe Leu Glu Asn Ala Gln Lys Leu Lys
        275                 280                 285

GAA ATA CAA CCT CTT ATC AAA GAA ACG AAT GTG AAA TTG TAT AAG GCT      912
Glu Ile Gln Pro Leu Ile Lys Glu Thr Asn Val Lys Leu Tyr Lys Ala
    290                 295                 300

ATG AGT GAG AGC TTG GAG CAG GTT GAG AAG GAA TTA AAA CAT AAT TCG      960
Met Ser Glu Ser Leu Glu Gln Val Glu Lys Glu Leu Lys His Asn Ser
305                 310                 315                 320

GAA GCT AAT TTA GAA GAT TTG GTT GCG AAA TCT AAA GAA ATC GTA AGA     1008
Glu Ala Asn Leu Glu Asp Leu Val Ala Lys Ser Lys Glu Ile Val Arg
                325                 330                 335

GAA TAC GAA GGA AAA CTT AAT CAA TCT AAA AAT CTT CCA GAA TTA AAG     1056
Glu Tyr Glu Gly Lys Leu Asn Gln Ser Lys Asn Leu Pro Glu Leu Lys
            340                 345                 350

CAA CTA GAA GAG GAA GCT CAT TCG AAG TTG AAA CAA GTT GTG GAG GAT     1104
Gln Leu Glu Glu Glu Ala His Ser Lys Leu Lys Gln Val Val Glu Asp
        355                 360                 365

TTT AGA AAA AAA TTT AAA ACG TCA GAG CAA GTG ACA CCA AAA AAA CGT     1152
Phe Arg Lys Lys Phe Lys Thr Ser Glu Gln Val Thr Pro Lys Lys Arg
    370                 375                 380

CTC AAA CGA GAT TTA GCT GCT AAT GAA AAT AAT CAA CAA AAG ATT GAG     1200
Leu Lys Arg Asp Leu Ala Ala Asn Glu Asn Asn Gln Gln Lys Ile Glu
385                 390                 395                 400

TTA ACA GTT TCA CCA GAG AAT ATC ACT GTA TAT GAA GGT GAA GAC GTG     1248
Leu Thr Val Ser Pro Glu Asn Ile Thr Val Tyr Glu Gly Glu Asp Val
                405                 410                 415

AAA TTT ACA GTC ACA GCT AAA AGT GAT TCG AAG ACG ACG TTG GAC TTC     1296
Lys Phe Thr Val Thr Ala Lys Ser Asp Ser Lys Thr Thr Leu Asp Phe
            420                 425                 430

AGT GAT CTT TTA ACA AAA TAT AAT CCG TCT GTA TCA GAT AGA ATT AGT     1344
Ser Asp Leu Leu Thr Lys Tyr Asn Pro Ser Val Ser Asp Arg Ile Ser
        435                 440                 445
```

-continued

```
ACA AAT TAT AAG ACT AAC ACG GAT AAT CAT AAG ATT GCC GAA ATC ACT     1392
Thr Asn Tyr Lys Thr Asn Thr Asp Asn His Lys Ile Ala Glu Ile Thr
    450                 455                 460

ATC AAG AAT TTG AAG CTA AAT GAA AGT CAA ACA GTG ACT CTA AAA GCT     1440
Ile Lys Asn Leu Lys Leu Asn Glu Ser Gln Thr Val Thr Leu Lys Ala
465                 470                 475                 480

AAA GAT GAT TCT GGC AAT GTA GTT GAA AAA ACA TTC ACT ATT ACA GTG     1488
Lys Asp Asp Ser Gly Asn Val Val Glu Lys Thr Phe Thr Ile Thr Val
                485                 490                 495

CAA AAG AAA GAG GAG AAA CAA GTT CCT AAA ACA CCA GAG CAG AAA GAT     1536
Gln Lys Lys Glu Glu Lys Gln Val Pro Lys Thr Pro Glu Gln Lys Asp
            500                 505                 510

TCT AAA ACG GAA GAA AAG GTT CCT CAA GAA CCA AAA TCA AAT GAC AAG     1584
Ser Lys Thr Glu Glu Lys Val Pro Gln Glu Pro Lys Ser Asn Asp Lys
        515                 520                 525

AAT CAA TTA CAA GAG TTG ATT AAA TCA GCT CAA CAA GAA CTG GAA AAG     1632
Asn Gln Leu Gln Glu Leu Ile Lys Ser Ala Gln Gln Glu Leu Glu Lys
    530                 535                 540

TTA GAA AAA GCA ATA AAA GAA TTA ATG GAG CAA CCA GAG ATT CCA TCC     1680
Leu Glu Lys Ala Ile Lys Glu Leu Met Glu Gln Pro Glu Ile Pro Ser
545                 550                 555                 560

AAT CCA GAG TAT GGT ATT CAA AAA TCT ATT TGG GAG TCA CAA AAA GAG     1728
Asn Pro Glu Tyr Gly Ile Gln Lys Ser Ile Trp Glu Ser Gln Lys Glu
                565                 570                 575

CCT ATC CAG GAA GCC ATA ACA AGT TTT AAG AAG ATT ATT GGT GAT TCA     1776
Pro Ile Gln Glu Ala Ile Thr Ser Phe Lys Lys Ile Ile Gly Asp Ser
            580                 585                 590

TCT TCA AAA TAC TAC ACA GAG CAC TAT TTT AAC AAA TAT AAA TCT CAT     1824
Ser Ser Lys Tyr Tyr Thr Glu His Tyr Phe Asn Lys Tyr Lys Ser His
        595                 600                 605

TTT ATG AAT TAT CAA CTT CAT GCA CAA ATG GAG ATG CTG ACT AGA AAA     1872
Phe Met Asn Tyr Gln Leu His Ala Gln Met Glu Met Leu Thr Arg Lys
    610                 615                 620

GTG GTT CAG TAT ATG AAC AAA TAT CCT GAT AAT GCA GAA ATT AAA AAG     1920
Val Val Gln Tyr Met Asn Lys Tyr Pro Asp Asn Ala Glu Ile Lys Lys
625                 630                 635                 640

ATA TTT GAG TCA GAT ATG AAG AGA ACG AAA GAA GAT AAT TAC GGA AGT     1968
Ile Phe Glu Ser Asp Met Lys Arg Thr Lys Glu Asp Asn Tyr Gly Ser
                645                 650                 655

TTA GAA AAT GAT GCT TTG AAA GGC TAT TTT GAG AAA TAT TTC CTT ACA     2016
Leu Glu Asn Asp Ala Leu Lys Gly Tyr Phe Glu Lys Tyr Phe Leu Thr
            660                 665                 670

CCA TTT AAT AAA ATT AAG CAG ATT GTA GAT GAT TTC GAT AAA AAA GTA     2064
Pro Phe Asn Lys Ile Lys Gln Ile Val Asp Asp Phe Asp Lys Lys Val
        675                 680                 685

GAA CAA GAT CAG CCA GCA CCA ATT CCG GAA AAT TCA GAA ATG GAT CAG     2112
Glu Gln Asp Gln Pro Ala Pro Ile Pro Glu Asn Ser Glu Met Asp Gln
    690                 695                 700

GCT AAG GAA AAG GCT AAG ATT GCT GTA TCG AAG TAT ATG AGT AAG GTT     2160
Ala Lys Glu Lys Ala Lys Ile Ala Val Ser Lys Tyr Met Ser Lys Val
705                 710                 715                 720

TTA GAT GGA GTT CAT CAA CAT CTG CAG AAG AAA AAT CAC AGT AAA ATT     2208
Leu Asp Gly Val His Gln His Leu Gln Lys Lys Asn His Ser Lys Ile
                725                 730                 735

GTT GAT CTT TTT AAG GAA CTT GAA GCG ATT AAA CAA CAA ACT ATT TTT     2256
Val Asp Leu Phe Lys Glu Leu Glu Ala Ile Lys Gln Gln Thr Ile Phe
            740                 745                 750

GAT ATT GAC AAT GCA AAG ACT GAA GTA GAG ATT GAT AAC TTA GTA CAC     2304
Asp Ile Asp Asn Ala Lys Thr Glu Val Glu Ile Asp Asn Leu Val His
```

-continued

```
        755             760             765

GAT GCA TTC TCA AAA ATG AAT GCT ACT GTT GCT AAA TTT CAA AAA GGT     2352
Asp Ala Phe Ser Lys Met Asn Ala Thr Val Ala Lys Phe Gln Lys Gly
    770             775             780

CTA GAG ACA AAT ACG CCA GAA ACT CCA GAT ACA CCG AAG ATT CCA GAG     2400
Leu Glu Thr Asn Thr Pro Glu Thr Pro Asp Thr Pro Lys Ile Pro Glu
785             790             795                 800

CTA CCT CAA GCC CCA GAT ACA CCG CAG GCT CCA GAC ACA CCG CAT GTT     2448
Leu Pro Gln Ala Pro Asp Thr Pro Gln Ala Pro Asp Thr Pro His Val
            805             810             815

CCG CAA TCA CCA AAG GCC CCA GAA GCA CCG CGT GTT CCG GAA TCA CCA     2496
Pro Gln Ser Pro Lys Ala Pro Glu Ala Pro Arg Val Pro Glu Ser Pro
        820             825             830

AAG ACT CCA GAA GCA CCC CAT GTT CCG GAA TCA CCA AAG GCC CCA GAA     2544
Lys Thr Pro Glu Ala Pro His Val Pro Glu Ser Pro Lys Ala Pro Glu
        835             840             845

GCA CCG CGT GTT CCG GAA TCA CCA AAG ACT CCA GAA GCA CCG CAT GTT     2592
Ala Pro Arg Val Pro Glu Ser Pro Lys Thr Pro Glu Ala Pro His Val
    850             855             860

CCG GAA TCA CCA AAG ACT CCA GAA GCA CCA AAG ATT CCG GAA CCC CCT     2640
Pro Glu Ser Pro Lys Thr Pro Glu Ala Pro Lys Ile Pro Glu Pro Pro
865             870             875                 880

AAG ACT CCA GAC GTC CCT AAC CTT CCA GAC GTC CCT AAG CTT CCA GAC     2688
Lys Thr Pro Asp Val Pro Asn Leu Pro Asp Val Pro Lys Leu Pro Asp
            885             890             895

GTC CCT AAG CTT CCA GAT GCA CCG AAG TTA CCA CAT GGG TTA AAT AAA     2736
Val Pro Lys Leu Pro Asp Ala Pro Lys Leu Pro His Gly Leu Asn Lys
        900             905             910

GTT GGA CAA GCA GTA TTT ACA TCA ACT GAT GGA AAT ACT AAG GTT ACG     2784
Val Gly Gln Ala Val Phe Thr Ser Thr Asp Gly Asn Thr Lys Val Thr
        915             920             925

GTT GTA TTT GAT AAA CCT ACA GAT GCT GAT AAG TTA CAT CTC AAG GAA     2832
Val Val Phe Asp Lys Pro Thr Asp Ala Asp Lys Leu His Leu Lys Glu
    930             935             940

GTA ACG ACG AAA GAG TTG GCT GAT AAA ATT GCT CAT AAA ACA GGA GGA     2880
Val Thr Thr Lys Glu Leu Ala Asp Lys Ile Ala His Lys Thr Gly Gly
945             950             955                 960

GGA ACA GTT CGT GTG TTT GAC TTA TCT CTT TCT AAA GGA GGC AAG GAA     2928
Gly Thr Val Arg Val Phe Asp Leu Ser Leu Ser Lys Gly Gly Lys Glu
            965             970             975

ACA CAT GTC AAT GGA GAA CGA ACT GTT CGG CTC GCG CTT GGG CAG ACT     2976
Thr His Val Asn Gly Glu Arg Thr Val Arg Leu Ala Leu Gly Gln Thr
        980             985             990

GGC TCA GAT GTT CAC GTC TAT CAC GTA AAG GAA AAT GGC GAC CTT GAG     3024
Gly Ser Asp Val His Val Tyr His Val Lys Glu Asn Gly Asp Leu Glu
        995             1000            1005

CGT ATT CCT TCT AAA GTT GAA AAT GGG CAA GTT GTT TTT AAA ACG AAC     3072
Arg Ile Pro Ser Lys Val Glu Asn Gly Gln Val Val Phe Lys Thr Asn
    1010            1015            1020

CAC TTC AGT TTG TTT GCG ATT AAG ACA CTT TCT AAG GAT CAA AAT GTT     3120
His Phe Ser Leu Phe Ala Ile Lys Thr Leu Ser Lys Asp Gln Asn Val
1025            1030            1035                1040

ACT CCA CCG AAG CAG ACT AAA CCT TCT ACC CAA GGC AGT CAA GTA GAG     3168
Thr Pro Pro Lys Gln Thr Lys Pro Ser Thr Gln Gly Ser Gln Val Glu
            1045            1050            1055

ATT GCA GAG AGT CAA ACT GGA AAA TTC CAG ACT AAA GCA GCT AAT CAT     3216
Ile Ala Glu Ser Gln Thr Gly Lys Phe Gln Thr Lys Ala Ala Asn His
        1060            1065            1070

AAA CCA CTG GCT ACT GGA AAT GAA ACA GTG GCA AAA GGA AAT CCT ACA     3264
```

-continued

```
Lys Pro Leu Ala Thr Gly Asn Glu Thr Val Ala Lys Gly Asn Pro Thr
        1075                1080                1085

TCA ACA ACG GAA AAG AAA CTC GAG CAC CAC                         3294
Ser Thr Thr Glu Lys Lys Leu Glu His His
    1090                1095
```

(2) INFORMATION FOR SEQ ID NO: 8:

(i) SEQUENCE CHARACTERISTICS:
(A) LENGTH: 1098 amino acids
(B) TYPE: amino acid
(D) TOPOLOGY: linear (ii) MOLECULE TYPE: protein (xi) SEQUENCE DESCRIPTION: SEQ ID NO: 8:

```
Glu Gly Asp Ile His Met Ser Glu Leu Val Lys Asp Asp Ser Val Lys
  1               5                  10                  15

Thr Thr Glu Val Ala Ala Lys Pro Tyr Pro Ser Met Ala Gln Thr Asp
             20                  25                  30

Gln Gly Asn Asn Ser Ser Ser Ser Glu Leu Glu Thr Thr Arg Met Glu
        35                  40                  45

Ile Pro Thr Thr Asp Ile Lys Lys Ala Val Glu Pro Val Glu Lys Thr
    50                  55                  60

Ala Gly Glu Thr Ser Ala Thr His Thr Gly Lys Arg Glu Lys Gln Leu
 65                  70                  75                  80

Gln Gln Trp Lys Asn Asn Leu Lys Asn Asp Val Asp Asn Thr Ile Leu
                 85                  90                  95

Ser His Glu Gln Lys Asn Glu Phe Lys Thr Lys Ile Asp Glu Thr Asn
            100                 105                 110

Asp Ser Asp Ala Leu Leu Glu Leu Glu Asn Gln Phe Asn Glu Thr Asn
        115                 120                 125

Arg Leu Leu His Ile Lys Gln His Glu Glu Val Glu Lys Asp Lys Lys
    130                 135                 140

Ala Lys Gln Gln Lys Thr Leu Lys Gln Ser Asp Thr Lys Val Asp Leu
145                 150                 155                 160

Ser Asn Ile Asp Lys Glu Leu Asn His Gln Lys Ser Gln Glu Ala Gly
                165                 170                 175

Ile Thr Asn Glu Asp Lys Asp Ser Met Leu Lys Lys Ile Glu Asp Ile
            180                 185                 190

Arg Lys Gln Ala Gln Gln Pro Asp Lys Lys Glu Asp Ala Glu Val Lys
        195                 200                 205

Val Arg Glu Glu Leu Gly Lys Leu Phe Ser Ser Thr Lys Ala Gly Leu
    210                 215                 220

Asp Gln Glu Ile Gln Glu His Val Lys Lys Glu Thr Ser Ser Glu Glu
225                 230                 235                 240

Asn Thr Gln Lys Val Asp Glu His Tyr Ala Asn Ser Leu Gln Asn Leu
                245                 250                 255

Ala Gln Lys Ser Leu Glu Glu Leu Asp Lys Ala Thr Thr Asn Glu Gln
            260                 265                 270

Ala Thr Gln Val Lys Asn Gln Phe Leu Glu Asn Ala Gln Lys Leu Lys
        275                 280                 285

Glu Ile Gln Pro Leu Ile Lys Glu Thr Asn Val Lys Leu Tyr Lys Ala
    290                 295                 300

Met Ser Glu Ser Leu Glu Gln Val Glu Lys Glu Leu Lys His Asn Ser
305                 310                 315                 320
```

-continued

```
Glu Ala Asn Leu Glu Asp Leu Val Ala Lys Ser Lys Glu Ile Val Arg
                325                 330                 335

Glu Tyr Glu Gly Lys Leu Asn Gln Ser Lys Asn Leu Pro Glu Leu Lys
            340                 345                 350

Gln Leu Glu Glu Glu Ala His Ser Lys Leu Lys Gln Val Val Glu Asp
        355                 360                 365

Phe Arg Lys Lys Phe Lys Thr Ser Glu Gln Val Thr Pro Lys Lys Arg
    370                 375                 380

Leu Lys Arg Asp Leu Ala Ala Asn Glu Asn Asn Gln Gln Lys Ile Glu
385                 390                 395                 400

Leu Thr Val Ser Pro Glu Asn Ile Thr Val Tyr Glu Gly Glu Asp Val
                405                 410                 415

Lys Phe Thr Val Thr Ala Lys Ser Asp Ser Lys Thr Thr Leu Asp Phe
            420                 425                 430

Ser Asp Leu Leu Thr Lys Tyr Asn Pro Ser Val Ser Asp Arg Ile Ser
        435                 440                 445

Thr Asn Tyr Lys Thr Asn Thr Asp Asn His Lys Ile Ala Glu Ile Thr
    450                 455                 460

Ile Lys Asn Leu Lys Leu Asn Glu Ser Gln Thr Val Thr Leu Lys Ala
465                 470                 475                 480

Lys Asp Asp Ser Gly Asn Val Val Glu Lys Thr Phe Thr Ile Thr Val
                485                 490                 495

Gln Lys Lys Glu Glu Lys Gln Val Pro Lys Thr Pro Glu Gln Lys Asp
            500                 505                 510

Ser Lys Thr Glu Glu Lys Val Pro Gln Glu Pro Lys Ser Asn Asp Lys
        515                 520                 525

Asn Gln Leu Gln Glu Leu Ile Lys Ser Ala Gln Gln Glu Leu Glu Lys
    530                 535                 540

Leu Glu Lys Ala Ile Lys Glu Leu Met Glu Gln Pro Glu Ile Pro Ser
545                 550                 555                 560

Asn Pro Glu Tyr Gly Ile Gln Lys Ser Ile Trp Glu Ser Gln Lys Glu
                565                 570                 575

Pro Ile Gln Glu Ala Ile Thr Ser Phe Lys Lys Ile Ile Gly Asp Ser
            580                 585                 590

Ser Ser Lys Tyr Tyr Thr Glu His Tyr Phe Asn Lys Tyr Lys Ser His
        595                 600                 605

Phe Met Asn Tyr Gln Leu His Ala Gln Met Glu Met Leu Thr Arg Lys
    610                 615                 620

Val Val Gln Tyr Met Asn Lys Tyr Pro Asp Asn Ala Glu Ile Lys Lys
625                 630                 635                 640

Ile Phe Glu Ser Asp Met Lys Arg Thr Lys Glu Asp Asn Tyr Gly Ser
                645                 650                 655

Leu Glu Asn Asp Ala Leu Lys Gly Tyr Phe Glu Lys Tyr Phe Leu Thr
            660                 665                 670

Pro Phe Asn Lys Ile Lys Gln Ile Val Asp Asp Phe Asp Lys Lys Val
        675                 680                 685

Glu Gln Asp Gln Pro Ala Pro Ile Pro Glu Asn Ser Glu Met Asp Gln
    690                 695                 700

Ala Lys Glu Lys Ala Lys Ile Ala Val Ser Lys Tyr Met Ser Lys Val
705                 710                 715                 720

Leu Asp Gly Val His Gln His Leu Gln Lys Lys Asn His Ser Lys Ile
                725                 730                 735

Val Asp Leu Phe Lys Glu Leu Glu Ala Ile Lys Gln Gln Thr Ile Phe
```

-continued

```
            740                 745                 750

Asp Ile Asp Asn Ala Lys Thr Glu Val Glu Ile Asp Asn Leu Val His
        755                 760                 765

Asp Ala Phe Ser Lys Met Asn Ala Thr Val Ala Lys Phe Gln Lys Gly
    770                 775                 780

Leu Glu Thr Asn Thr Pro Glu Thr Pro Asp Thr Pro Lys Ile Pro Glu
785                 790                 795                 800

Leu Pro Gln Ala Pro Asp Thr Pro Gln Ala Pro Asp Thr Pro His Val
                805                 810                 815

Pro Gln Ser Pro Lys Ala Pro Glu Ala Pro Arg Val Pro Glu Ser Pro
            820                 825                 830

Lys Thr Pro Glu Ala Pro His Val Pro Glu Ser Pro Lys Ala Pro Glu
        835                 840                 845

Ala Pro Arg Val Pro Glu Ser Pro Lys Thr Pro Glu Ala Pro His Val
    850                 855                 860

Pro Glu Ser Pro Lys Thr Pro Glu Ala Pro Lys Ile Pro Glu Pro Pro
865                 870                 875                 880

Lys Thr Pro Asp Val Pro Asn Leu Pro Asp Val Pro Lys Leu Pro Asp
                885                 890                 895

Val Pro Lys Leu Pro Asp Ala Pro Lys Leu Pro His Gly Leu Asn Lys
            900                 905                 910

Val Gly Gln Ala Val Phe Thr Ser Thr Asp Gly Asn Thr Lys Val Thr
        915                 920                 925

Val Val Phe Asp Lys Pro Thr Asp Ala Asp Lys Leu His Leu Lys Glu
    930                 935                 940

Val Thr Thr Lys Glu Leu Ala Asp Lys Ile Ala His Lys Thr Gly Gly
945                 950                 955                 960

Gly Thr Val Arg Val Phe Asp Leu Ser Leu Ser Lys Gly Gly Lys Glu
                965                 970                 975

Thr His Val Asn Gly Glu Arg Thr Val Arg Leu Ala Leu Gly Gln Thr
            980                 985                 990

Gly Ser Asp Val His Val Tyr His Val Lys Glu Asn Gly Asp Leu Glu
        995                 1000                1005

Arg Ile Pro Ser Lys Val Glu Asn Gly Gln Val Val Phe Lys Thr Asn
    1010                1015                1020

His Phe Ser Leu Phe Ala Ile Lys Thr Leu Ser Lys Asp Gln Asn Val
1025                1030                1035                1040

Thr Pro Pro Lys Gln Thr Lys Pro Ser Thr Gln Gly Ser Gln Val Glu
                1045                1050                1055

Ile Ala Glu Ser Gln Thr Gly Lys Phe Gln Thr Lys Ala Ala Asn His
            1060                1065                1070

Lys Pro Leu Ala Thr Gly Asn Glu Thr Val Ala Lys Gly Asn Pro Thr
        1075                1080                1085

Ser Thr Thr Glu Lys Lys Leu Glu His His
    1090                1095
```

(2) INFORMATION FOR SEQ ID NO: 9:

(i) SEQUENCE CHARACTERISTICS:
(A) LENGTH: 3492 base pairs
(B) TYPE: nucleic acid
(C) STRANDEDNESS: single
(D) TOPOLOGY: linear (ii) MOLECULE TYPE: cDNA -continued

```
(ix) FEATURE:
      (A) NAME/KEY: CDS
      (B) LOCATION: 1..3492

(xi) SEQUENCE DESCRIPTION: SEQ ID NO: 9:

ATG TTT AAA TCT AAT TAT GAA AGA AAA ATG CGT TAT TCC ATT CGT AAA       48
Met Phe Lys Ser Asn Tyr Glu Arg Lys Met Arg Tyr Ser Ile Arg Lys
  1               5                  10                  15

TTT AGT GTA GGA GTA GCT AGT GTA GCG GTA GCT AGT TTG TTC ATG GGA       96
Phe Ser Val Gly Val Ala Ser Val Ala Val Ala Ser Leu Phe Met Gly
             20                  25                  30

AGC GTT GCT CAT GCA AGT GAG CTT GTA AAG CAC GAT AGT GTG AAG ACT      144
Ser Val Ala His Ala Ser Glu Leu Val Lys His Asp Ser Val Lys Thr
         35                  40                  45

ACC GAG GTT GCA GCT AAG CCC TAT CCA AGT ATG GCT CAA ACA GAT CAA      192
Thr Glu Val Ala Ala Lys Pro Tyr Pro Ser Met Ala Gln Thr Asp Gln
     50                  55                  60

GGA AAT AAT TCA TCA TCC TCG GAA CTT GAG ACA ACA AAG ATC GAA ATT      240
Gly Asn Asn Ser Ser Ser Ser Glu Leu Glu Thr Thr Lys Ile Glu Ile
 65                  70                  75                  80

CCT ACA ACA GAC ATA AAA AAA GCT GTT GAA CCG CTC GAG AAA ACA GCT      288
Pro Thr Thr Asp Ile Lys Lys Ala Val Glu Pro Leu Glu Lys Thr Ala
                 85                  90                  95

GGG GAA ACA TCT GCC ACT GAT ACT GGA AAA CGA GAG AAA CAA TTA CAA      336
Gly Glu Thr Ser Ala Thr Asp Thr Gly Lys Arg Glu Lys Gln Leu Gln
            100                 105                 110

CAA TGG AAA AAT AAT CTA AAA AAT GAT GTG CAT AAC ACA ATT CTA TCT      384
Gln Trp Lys Asn Asn Leu Lys Asn Asp Val His Asn Thr Ile Leu Ser
        115                 120                 125

CAT GAA CAG AAA AAT GAG TTT AAA ACA AAA ATT GAT GAA ACA AAT GAT      432
His Glu Gln Lys Asn Glu Phe Lys Thr Lys Ile Asp Glu Thr Asn Asp
    130                 135                 140

TCT GAT GCA TTA TTA GAA TTA GAA AAT CAA TTT AAC GAA ACT AAT AGA      480
Ser Asp Ala Leu Leu Glu Leu Glu Asn Gln Phe Asn Glu Thr Asn Arg
145                 150                 155                 160

CTG TTA CAC ATC AAA CAA CAT GAA GAA GTT GAG AAA GAT AAG AAA GCT      528
Leu Leu His Ile Lys Gln His Glu Glu Val Glu Lys Asp Lys Lys Ala
                165                 170                 175

AAG CAA CAG AAA ACT CTG AAA CAG TCA GAT ACC AAA GTA GAT CTA AGC      576
Lys Gln Gln Lys Thr Leu Lys Gln Ser Asp Thr Lys Val Asp Leu Ser
            180                 185                 190

AAT ATT GAC AAA GAG CTT AAT CAT CAA AAA AGT CAA GTT GAA ACC ATG      624
Asn Ile Asp Lys Glu Leu Asn His Gln Lys Ser Gln Val Glu Thr Met
        195                 200                 205

GCA GAG CAA CTC GGG ATC ACA AAT GAA GAT AAA GAT TCT ATG CTG AAA      672
Ala Glu Gln Leu Gly Ile Thr Asn Glu Asp Lys Asp Ser Met Leu Lys
    210                 215                 220

AAA ATC GAA GAT ATT CGT AAA CAA GCT CAA CAA GCA GAT AAA AAA GAA      720
Lys Ile Glu Asp Ile Arg Lys Gln Ala Gln Gln Ala Asp Lys Lys Glu
225                 230                 235                 240

GAT GCC GAA GTA AAG GTT CGT GAA GAA CTA GGT AAA CTC TTT ACT TCA      768
Asp Ala Glu Val Lys Val Arg Glu Glu Leu Gly Lys Leu Phe Thr Ser
                245                 250                 255

ACT AAA GCT GGT CTG GAT CAA GAA ATT CAA GAG CAT GTG AAG AAA GAA      816
Thr Lys Ala Gly Leu Asp Gln Glu Ile Gln Glu His Val Lys Lys Glu
            260                 265                 270

ACG ACT AGT GAG GAA AAT ACT CAG AAA GTT GAT GAA CAC TAT CCT AAT      864
Thr Thr Ser Glu Glu Asn Thr Gln Lys Val Asp Glu His Tyr Pro Asn
        275                 280                 285

AGC CTT CAG AAC CTT GCT CAA AAA TCT CTT GAA GAA CTA GAT AAG GCA      912
```

-continued

```
Ser Leu Gln Asn Leu Ala Gln Lys Ser Leu Glu Glu Leu Asp Lys Ala
    290                 295                 300

ACT ACC AAT GAA CAA GCT ACA CAA GTT AAA AAT CAA TTC TTA GAA AAC      960
Thr Thr Asn Glu Gln Ala Thr Gln Val Lys Asn Gln Phe Leu Glu Asn
305                 310                 315                 320

GCT CAA AAG CTC AAA GAA ATA CAA CCT CTT ATC AAA GAA ACG AAT GTG     1008
Ala Gln Lys Leu Lys Glu Ile Gln Pro Leu Ile Lys Glu Thr Asn Val
                325                 330                 335

AAA TTG TAT AAG GCT ATG AGT GAG AGC TTG GAG CAG GTT GAG AAG CAA     1056
Lys Leu Tyr Lys Ala Met Ser Glu Ser Leu Glu Gln Val Glu Lys Gln
            340                 345                 350

TTA AAA CAT AAT TCG CAA GCT AAT TTA GAA GAT TTG GTT GCG AAA TCT     1104
Leu Lys His Asn Ser Gln Ala Asn Leu Glu Asp Leu Val Ala Lys Ser
        355                 360                 365

AAA GAA ATC GTA AGA GAA TAC GAA GGA AAA CTT AAT CAA TCT AAA AAT     1152
Lys Glu Ile Val Arg Glu Tyr Glu Gly Lys Leu Asn Gln Ser Lys Asn
    370                 375                 380

CTT CCA GAA TTA AAG CAA CTA GAA GAG GAA GCT CAT TCG AAG TTG AAA     1200
Leu Pro Glu Leu Lys Gln Leu Glu Glu Glu Ala His Ser Lys Leu Lys
385                 390                 395                 400

CAA GTT GTG GAG GAT TTT AGA AAA AAA TTT AAA ACC TCA GAG CAA GTG     1248
Gln Val Val Glu Asp Phe Arg Lys Lys Phe Lys Thr Ser Glu Gln Val
                405                 410                 415

ACA CCA AAA AAA CGT GTC AAA CGA GAT TTA GCT GCT AAT GAA AAT AAT     1296
Thr Pro Lys Lys Arg Val Lys Arg Asp Leu Ala Ala Asn Glu Asn Asn
            420                 425                 430

CAA CAA AAG ATT GAG TTA ACA GTT TCA CCA GAG AAT ATC ACT GTA TAT     1344
Gln Gln Lys Ile Glu Leu Thr Val Ser Pro Glu Asn Ile Thr Val Tyr
        435                 440                 445

GAA GGT GAA GAC CTG AAA TTT ACA CTC ACA GCT AAA AGT GAT TCG AAG     1392
Glu Gly Glu Asp Leu Lys Phe Thr Leu Thr Ala Lys Ser Asp Ser Lys
    450                 455                 460

ACG ACG TTG GAC TTC AGT GAT CTT TTA ACA AAA TAT AAT CCG TCT GTA     1440
Thr Thr Leu Asp Phe Ser Asp Leu Leu Thr Lys Tyr Asn Pro Ser Val
465                 470                 475                 480

TCA GAT AGA ATT AGT ACA AAT TAT AAG ACT AAC ACG GAT AAT CAT AAG     1488
Ser Asp Arg Ile Ser Thr Asn Tyr Lys Thr Asn Thr Asp Asn His Lys
                485                 490                 495

ATT GCC GAA ATC ACT ATC AAG AAT TTG AAG CTA AAT GAA AGT CAA ACA     1536
Ile Ala Glu Ile Thr Ile Lys Asn Leu Lys Leu Asn Glu Ser Gln Thr
            500                 505                 510

GTG ACT CTA AAA GCT AAA GAT GAT TCT GGC AAT GTA GTT CAA AAA ACA     1584
Val Thr Leu Lys Ala Lys Asp Asp Ser Gly Asn Val Val Gln Lys Thr
        515                 520                 525

TTC ACT ATT ACA GTG CAA AAG AAA GAG GAG AAA CAA GTT CCT AAA ACA     1632
Phe Thr Ile Thr Val Gln Lys Lys Glu Glu Lys Gln Val Pro Lys Thr
    530                 535                 540

CCA GAG CAG AAA GAT TCT AAA ACG GAA GAA AAG GTT CCT CAA GAA CCA     1680
Pro Glu Gln Lys Asp Ser Lys Thr Glu Glu Lys Val Pro Gln Glu Pro
545                 550                 555                 560

AAA TCA AAT GAC AAG AAT CAA TTA CAA GAG TTG ATT AAA TCA GCT CAA     1728
Lys Ser Asn Asp Lys Asn Gln Leu Gln Glu Leu Ile Lys Ser Ala Gln
                565                 570                 575

CAA CAA CTG GAA AAG TTA GAA AAA GCA ATA AAA GAA TTA ATG GAG CAA     1776
Gln Gln Leu Glu Lys Leu Glu Lys Ala Ile Lys Glu Leu Met Glu Gln
            580                 585                 590

CCA GAG ATT CCA TCC AAT CCA GAG TAT GGT ATT CAA AAA TCT ATT TGG     1824
Pro Glu Ile Pro Ser Asn Pro Glu Tyr Gly Ile Gln Lys Ser Ile Trp
        595                 600                 605
```

-continued

```
GAG TCA CAA AAA GAG CCT ATC CAG GAA GCC ATA ACA AGT TTT AAG AAG      1872
Glu Ser Gln Lys Glu Pro Ile Gln Glu Ala Ile Thr Ser Phe Lys Lys
    610                 615                 620

ATT ATT GGT GAT TCA TCT TCA AAA TAC TAC ACA GAG CAC TAT TTT AAC      1920
Ile Ile Gly Asp Ser Ser Ser Lys Tyr Tyr Thr Glu His Tyr Phe Asn
625                 630                 635                 640

AAA TAT AAA TCT GAT TTT ATG AAT TAT CAA CTT CAT GCA CAA ATG GAG      1968
Lys Tyr Lys Ser Asp Phe Met Asn Tyr Gln Leu His Ala Gln Met Glu
                645                 650                 655

ATG CTG ACT AGA AAA GTG GTT CAG TAT ATC AAC AAA TAT CCT GAT AAT      2016
Met Leu Thr Arg Lys Val Val Gln Tyr Ile Asn Lys Tyr Pro Asp Asn
            660                 665                 670

GCA GAA ATT AAA AAG ATA TTT GAG TCA GAT ATG AAG AGA ACG AAA GAA      2064
Ala Glu Ile Lys Lys Ile Phe Glu Ser Asp Met Lys Arg Thr Lys Glu
        675                 680                 685

GAT AAT TAC GGA AGT TTA GAA AAT GAT GCT TTG AAA GGC TAT TTT GAG      2112
Asp Asn Tyr Gly Ser Leu Glu Asn Asp Ala Leu Lys Gly Tyr Phe Glu
    690                 695                 700

AAA TAT TTC CTT ACA CCA TTT AAT AAA ATT AAG CAG ATT GTA GAT GAT      2160
Lys Tyr Phe Leu Thr Pro Phe Asn Lys Ile Lys Gln Ile Val Asp Asp
705                 710                 715                 720

TTG GAT AAA AAA GTA GAA CAA GAT CAG CCA GCA CCA ATT CCG GAA AAT      2208
Leu Asp Lys Lys Val Glu Gln Asp Gln Pro Ala Pro Ile Pro Glu Asn
                725                 730                 735

TCA GAA ATG GAT CAG GCT AAG GAA AAG GCT AAG ATT GCT GTA TCG AAG      2256
Ser Glu Met Asp Gln Ala Lys Glu Lys Ala Lys Ile Ala Val Ser Lys
            740                 745                 750

TAT ATG AGT AAG GTT TTA GAT GGA GTT CAT CAA CAT CTG CAG AAG AAA      2304
Tyr Met Ser Lys Val Leu Asp Gly Val His Gln His Leu Gln Lys Lys
        755                 760                 765

AAT AAC ACT AAA ATT GTT GAT CTT TTT AAG GAA CTT GAA GCG ATT AAA      2352
Asn Asn Thr Lys Ile Val Asp Leu Phe Lys Glu Leu Glu Ala Ile Lys
    770                 775                 780

CAA CAA ACT ATT TTT GAT ATT GAC AAT GCA AAG ACT GAA GTA GAG ATT      2400
Gln Gln Thr Ile Phe Asp Ile Asp Asn Ala Lys Thr Glu Val Glu Ile
785                 790                 795                 800

GAT AAC TTA GTA CAC GAT GCA TTC TCA AAA ATG AAT GCT ACT GTT GCT      2448
Asp Asn Leu Val His Asp Ala Phe Ser Lys Met Asn Ala Thr Val Ala
                805                 810                 815

AAA TTT CAA AAA GGT CTA GAG ACA AAT ACG CCA GAA ACT CCA CAT ACA      2496
Lys Phe Gln Lys Gly Leu Glu Thr Asn Thr Pro Glu Thr Pro His Thr
            820                 825                 830

CCC AAG ATT CCA GAG CTA CCT CAA GCC CCA GAT ACA CCG CAG GCT CCA      2544
Pro Lys Ile Pro Glu Leu Pro Gln Ala Pro Asp Thr Pro Gln Ala Pro
        835                 840                 845

GAC ACA CCG CAT GTT CCG GAA TCA CCA AAG GCC CCA GAA GCA CCC CGT      2592
Asp Thr Pro His Val Pro Glu Ser Pro Lys Ala Pro Glu Ala Pro Arg
    850                 855                 860

GTT CCG GAA TCA CCA AAC ACT CCA GAA GCA CCG CAT GTT CCC CAA TCA      2640
Val Pro Glu Ser Pro Asn Thr Pro Glu Ala Pro His Val Pro Gln Ser
865                 870                 875                 880

CCA AAG GCC CCA GAA GCA CCG CGT GTT CCG GAA TCA CCA AAC ACT CCA      2688
Pro Lys Ala Pro Glu Ala Pro Arg Val Pro Glu Ser Pro Asn Thr Pro
                885                 890                 895

GAA GCA CCG CAT GTT CCG GAA TCA CCA AAG ACT CCA GAA GCA CCA AAG      2736
Glu Ala Pro His Val Pro Glu Ser Pro Lys Thr Pro Glu Ala Pro Lys
            900                 905                 910

ATT CCG GAA CCC CCT AAG ACT CCA GAC GTC CCT AAG CTT CCA GAC GTC      2784
Ile Pro Glu Pro Pro Lys Thr Pro Asp Val Pro Lys Leu Pro Asp Val
        915                 920                 925
```

-continued

```
CCT AAG CTT CCA GAC GTC CCT AAG CTT CCA GAT GCA CCC AAG TTA CCA     2832
Pro Lys Leu Pro Asp Val Pro Lys Leu Pro Asp Ala Pro Lys Leu Pro
    930                 935                 940

GAT GGG TTA AAT AAA GTT GGA CAA GCA GTA TTT ACA TCA ACT GAT GGA     2880
Asp Gly Leu Asn Lys Val Gly Gln Ala Val Phe Thr Ser Thr Asp Gly
945                 950                 955                 960

AAT ACT AAG GTT ACG GTT GTA TTT GAT AAA CCT ACA GAT GCT GAT AAG     2928
Asn Thr Lys Val Thr Val Val Phe Asp Lys Pro Thr Asp Ala Asp Lys
                965                 970                 975

TTA CAT CTC AAG GAA CTA ACG ACG AAA GAG TTG GCT GAT AAA ATT GCT     2976
Leu His Leu Lys Glu Leu Thr Thr Lys Glu Leu Ala Asp Lys Ile Ala
            980                 985                 990

CAT AAA ACA GGA GGA GGA ACA GTT CGT GTG TTT GAC TTA TCT CTT TCT     3024
His Lys Thr Gly Gly Gly Thr Val Arg Val Phe Asp Leu Ser Leu Ser
        995                 1000                1005

AAA GGA GGC AAG GAA ACA CAT GTC AAT GGA CAA CGA ACT GTT CGG CTC     3072
Lys Gly Gly Lys Glu Thr His Val Asn Gly Gln Arg Thr Val Arg Leu
    1010                1015                1020

GCG CTT GGG CAG ACT GGC TCA GAT GTT CAC GTC TAT CAC GTA AAG GAA     3120
Ala Leu Gly Gln Thr Gly Ser Asp Val His Val Tyr His Val Lys Glu
1025                1030                1035                1040

AAT GGC GAC CTT GAG CGT ATT CCT TCT AAA GTT GAA AAT GGG CAA GTT     3168
Asn Gly Asp Leu Glu Arg Ile Pro Ser Lys Val Glu Asn Gly Gln Val
                1045                1050                1055

GTT TTT AAA ACG AAC CAC TTC AGT TTG TTT GCG ATT AAG ACA CTT TCT     3216
Val Phe Lys Thr Asn His Phe Ser Leu Phe Ala Ile Lys Thr Leu Ser
            1060                1065                1070

AAG GAT CAA AAT GTT ACT CCA CCG AAG CAG ACT AAA CCT TCT ACC CAA     3264
Lys Asp Gln Asn Val Thr Pro Pro Lys Gln Thr Lys Pro Ser Thr Gln
        1075                1080                1085

GGC AGT CAA GTA GAG ATT GCA GAG AGT CAA ACT GGA AAA TTC CAG AGT     3312
Gly Ser Gln Val Glu Ile Ala Glu Ser Gln Thr Gly Lys Phe Gln Ser
    1090                1095                1100

AAA GCA GCT AAT CAT AAA GCA CTC GCT ACT GGA AAT GAA ACA GTG GCA     3360
Lys Ala Ala Asn His Lys Ala Leu Ala Thr Gly Asn Glu Thr Val Ala
1105                1110                1115                1120

AAA GGA AAT CCT ACA TCA ACA ACG CAA AAG AAA TTG CCA TAT ACA GGA     3408
Lys Gly Asn Pro Thr Ser Thr Thr Gln Lys Lys Leu Pro Tyr Thr Gly
                1125                1130                1135

GTG GCA TCT AAT CTA GTT CTT GAA ATT ATG GGT CTC CTT GGT TTG ATT     3456
Val Ala Ser Asn Leu Val Leu Glu Ile Met Gly Leu Leu Gly Leu Ile
            1140                1145                1150

GGA ACT TCA TTC ATC GCA ATG AAA AGA AGA AAA TCA                     3492
Gly Thr Ser Phe Ile Ala Met Lys Arg Arg Lys Ser
        1155                1160
```

(2) INFORMATION FOR SEQ ID NO: 10:

(i) SEQUENCE CHARACTERISTICS:
(A) LENGTH: 1164 amino acids
(B) TYPE: amino acid
(D) TOPOLOGY: linear (ii) MOLECULE TYPE: protein (xi) SEQUENCE DESCRIPTION: SEQ ID NO: 10:

```
Met Phe Lys Ser Asn Tyr Glu Arg Lys Met Arg Tyr Ser Ile Arg Lys
  1               5                  10                  15

Phe Ser Val Gly Val Ala Ser Val Ala Val Ala Ser Leu Phe Met Gly
             20                  25                  30
```

-continued

```
Ser Val Ala His Ala Ser Glu Leu Val Lys His Asp Ser Val Lys Thr
         35                  40                  45

Thr Glu Val Ala Ala Lys Pro Tyr Pro Ser Met Ala Gln Thr Asp Gln
     50                  55                  60

Gly Asn Asn Ser Ser Ser Ser Glu Leu Glu Thr Thr Lys Ile Glu Ile
 65                  70                  75                  80

Pro Thr Thr Asp Ile Lys Lys Ala Val Glu Pro Leu Glu Lys Thr Ala
                 85                  90                  95

Gly Glu Thr Ser Ala Thr Asp Thr Gly Lys Arg Glu Lys Gln Leu Gln
            100                 105                 110

Gln Trp Lys Asn Asn Leu Lys Asn Asp Val His Asn Thr Ile Leu Ser
        115                 120                 125

His Glu Gln Lys Asn Glu Phe Lys Thr Lys Ile Asp Glu Thr Asn Asp
    130                 135                 140

Ser Asp Ala Leu Leu Glu Leu Glu Asn Gln Phe Asn Glu Thr Asn Arg
145                 150                 155                 160

Leu Leu His Ile Lys Gln His Glu Glu Val Glu Lys Asp Lys Lys Ala
                165                 170                 175

Lys Gln Gln Lys Thr Leu Lys Gln Ser Asp Thr Lys Val Asp Leu Ser
            180                 185                 190

Asn Ile Asp Lys Glu Leu Asn His Gln Lys Ser Gln Val Glu Thr Met
        195                 200                 205

Ala Glu Gln Leu Gly Ile Thr Asn Glu Asp Lys Asp Ser Met Leu Lys
    210                 215                 220

Lys Ile Glu Asp Ile Arg Lys Gln Ala Gln Gln Ala Asp Lys Lys Glu
225                 230                 235                 240

Asp Ala Glu Val Lys Val Arg Glu Glu Leu Gly Lys Leu Phe Thr Ser
                245                 250                 255

Thr Lys Ala Gly Leu Asp Gln Glu Ile Gln Glu His Val Lys Lys Glu
            260                 265                 270

Thr Thr Ser Glu Glu Asn Thr Gln Lys Val Asp Glu His Tyr Pro Asn
        275                 280                 285

Ser Leu Gln Asn Leu Ala Gln Lys Ser Leu Glu Glu Leu Asp Lys Ala
    290                 295                 300

Thr Thr Asn Glu Gln Ala Thr Gln Val Lys Asn Gln Phe Leu Glu Asn
305                 310                 315                 320

Ala Gln Lys Leu Lys Glu Ile Gln Pro Leu Ile Lys Glu Thr Asn Val
                325                 330                 335

Lys Leu Tyr Lys Ala Met Ser Glu Ser Leu Glu Gln Val Glu Lys Gln
            340                 345                 350

Leu Lys His Asn Ser Gln Ala Asn Leu Glu Asp Leu Val Ala Lys Ser
        355                 360                 365

Lys Glu Ile Val Arg Glu Tyr Glu Gly Lys Leu Asn Gln Ser Lys Asn
    370                 375                 380

Leu Pro Glu Leu Lys Gln Leu Glu Glu Glu Ala His Ser Lys Leu Lys
385                 390                 395                 400

Gln Val Val Glu Asp Phe Arg Lys Lys Phe Lys Thr Ser Glu Gln Val
                405                 410                 415

Thr Pro Lys Lys Arg Val Lys Arg Asp Leu Ala Ala Asn Glu Asn Asn
            420                 425                 430

Gln Gln Lys Ile Glu Leu Thr Val Ser Pro Glu Asn Ile Thr Val Tyr
        435                 440                 445

Glu Gly Glu Asp Leu Lys Phe Thr Leu Thr Ala Lys Ser Asp Ser Lys
```

-continued

```
    450                 455                 460

Thr Thr Leu Asp Phe Ser Asp Leu Leu Thr Lys Tyr Asn Pro Ser Val
465                 470                 475                 480

Ser Asp Arg Ile Ser Thr Asn Tyr Lys Thr Asn Thr Asp Asn His Lys
                485                 490                 495

Ile Ala Glu Ile Thr Ile Lys Asn Leu Lys Leu Asn Glu Ser Gln Thr
            500                 505                 510

Val Thr Leu Lys Ala Lys Asp Asp Ser Gly Asn Val Val Gln Lys Thr
        515                 520                 525

Phe Thr Ile Thr Val Gln Lys Lys Glu Glu Lys Gln Val Pro Lys Thr
    530                 535                 540

Pro Glu Gln Lys Asp Ser Lys Thr Glu Glu Lys Val Pro Gln Glu Pro
545                 550                 555                 560

Lys Ser Asn Asp Lys Asn Gln Leu Gln Glu Leu Ile Lys Ser Ala Gln
                565                 570                 575

Gln Gln Leu Glu Lys Leu Glu Lys Ala Ile Lys Glu Leu Met Glu Gln
            580                 585                 590

Pro Glu Ile Pro Ser Asn Pro Glu Tyr Gly Ile Gln Lys Ser Ile Trp
        595                 600                 605

Glu Ser Gln Lys Glu Pro Ile Gln Glu Ala Ile Thr Ser Phe Lys Lys
    610                 615                 620

Ile Ile Gly Asp Ser Ser Ser Lys Tyr Tyr Thr Glu His Tyr Phe Asn
625                 630                 635                 640

Lys Tyr Lys Ser Asp Phe Met Asn Tyr Gln Leu His Ala Gln Met Glu
                645                 650                 655

Met Leu Thr Arg Lys Val Val Gln Tyr Ile Asn Lys Tyr Pro Asp Asn
            660                 665                 670

Ala Glu Ile Lys Lys Ile Phe Glu Ser Asp Met Lys Arg Thr Lys Glu
        675                 680                 685

Asp Asn Tyr Gly Ser Leu Glu Asn Asp Ala Leu Lys Gly Tyr Phe Glu
    690                 695                 700

Lys Tyr Phe Leu Thr Pro Phe Asn Lys Ile Lys Gln Ile Val Asp Asp
705                 710                 715                 720

Leu Asp Lys Lys Val Glu Gln Asp Gln Pro Ala Pro Ile Pro Glu Asn
                725                 730                 735

Ser Glu Met Asp Gln Ala Lys Glu Lys Ala Lys Ile Ala Val Ser Lys
            740                 745                 750

Tyr Met Ser Lys Val Leu Asp Gly Val His Gln His Leu Gln Lys Lys
        755                 760                 765

Asn Asn Thr Lys Ile Val Asp Leu Phe Lys Glu Leu Glu Ala Ile Lys
    770                 775                 780

Gln Gln Thr Ile Phe Asp Ile Asp Asn Ala Lys Thr Glu Val Glu Ile
785                 790                 795                 800

Asp Asn Leu Val His Asp Ala Phe Ser Lys Met Asn Ala Thr Val Ala
                805                 810                 815

Lys Phe Gln Lys Gly Leu Glu Thr Asn Thr Pro Glu Thr Pro His Thr
            820                 825                 830

Pro Lys Ile Pro Glu Leu Pro Gln Ala Pro Asp Thr Pro Gln Ala Pro
        835                 840                 845

Asp Thr Pro His Val Pro Glu Ser Pro Lys Ala Pro Glu Ala Pro Arg
    850                 855                 860

Val Pro Glu Ser Pro Asn Thr Pro Glu Ala Pro His Val Pro Gln Ser
865                 870                 875                 880
```

-continued

```
Pro Lys Ala Pro Glu Ala Pro Arg Val Pro Glu Ser Pro Asn Thr Pro
                885                 890                 895

Glu Ala Pro His Val Pro Glu Ser Pro Lys Thr Pro Glu Ala Pro Lys
            900                 905                 910

Ile Pro Glu Pro Pro Lys Thr Pro Asp Val Pro Lys Leu Pro Asp Val
        915                 920                 925

Pro Lys Leu Pro Asp Val Pro Lys Leu Pro Asp Ala Pro Lys Leu Pro
    930                 935                 940

Asp Gly Leu Asn Lys Val Gly Gln Ala Val Phe Thr Ser Thr Asp Gly
945                 950                 955                 960

Asn Thr Lys Val Thr Val Val Phe Asp Lys Pro Thr Asp Ala Asp Lys
                965                 970                 975

Leu His Leu Lys Glu Leu Thr Thr Lys Glu Leu Ala Asp Lys Ile Ala
            980                 985                 990

His Lys Thr Gly Gly Gly Thr Val Arg Val Phe Asp Leu Ser Leu Ser
        995                 1000                1005

Lys Gly Gly Lys Glu Thr His Val Asn Gly Gln Arg Thr Val Arg Leu
    1010                1015                1020

Ala Leu Gly Gln Thr Gly Ser Asp Val His Val Tyr His Val Lys Glu
1025                1030                1035                1040

Asn Gly Asp Leu Glu Arg Ile Pro Ser Lys Val Glu Asn Gly Gln Val
                1045                1050                1055

Val Phe Lys Thr Asn His Phe Ser Leu Phe Ala Ile Lys Thr Leu Ser
            1060                1065                1070

Lys Asp Gln Asn Val Thr Pro Pro Lys Gln Thr Lys Pro Ser Thr Gln
        1075                1080                1085

Gly Ser Gln Val Glu Ile Ala Glu Ser Gln Thr Gly Lys Phe Gln Ser
    1090                1095                1100

Lys Ala Ala Asn His Lys Ala Leu Ala Thr Gly Asn Glu Thr Val Ala
1105                1110                1115                1120

Lys Gly Asn Pro Thr Ser Thr Thr Gln Lys Lys Leu Pro Tyr Thr Gly
                1125                1130                1135

Val Ala Ser Asn Leu Val Leu Glu Ile Met Gly Leu Leu Gly Leu Ile
            1140                1145                1150

Gly Thr Ser Phe Ile Ala Met Lys Arg Arg Lys Ser
        1155                1160
```

(2) INFORMATION FOR SEQ ID NO: 11:

(i) SEQUENCE CHARACTERISTICS:
  (A) LENGTH: 106 amino acids
  (B) TYPE: amino acid
  (C) STRANDEDNESS: single
  (D) TOPOLOGY: Not Relevant (ii) MOLECULE TYPE: peptide (xi) SEQUENCE DESCRIPTION: SEQ ID NO: 11:

```
Leu Leu His Ile Lys Gln His Glu Glu Val Glu Lys Asp Lys Lys Ala
1               5                   10                  15

Lys Gln Gln Lys Thr Leu Lys Gln Ser Asp Thr Lys Val Asp Leu Ser
            20                  25                  30

Asn Ile Asp Lys Glu Leu Asn His Gln Lys Ser Gln Val Glu Lys Met
        35                  40                  45

Ala Glu Gln Lys Gly Ile Thr Asn Glu Asp Lys Asp Ser Met Leu Lys
    50                  55                  60
```

```
Lys Ile Glu Asp Ile Arg Lys Gln Ala Gln Gln Ala Asp Lys Lys Glu
65                  70                  75                  80

Asp Ala Glu Val Lys Val Arg Glu Glu Leu Gly Lys Leu Phe Ser Ser
                85                  90                  95

Thr Lys Ala Gly Leu Asp Gln Glu Ile Gln
            100                 105
```

(2) INFORMATION FOR SEQ ID NO: 12:

(i) SEQUENCE CHARACTERISTICS:
(A) LENGTH: 147 amino acids
(B) TYPE: amino acid
(C) STRANDEDNESS: single
(D) TOPOLOGY: Not Relevant (ii) MOLECULE TYPE: peptide (xi) SEQUENCE DESCRIPTION: SEQ ID NO: 12:

```
Asp Ser Asp Ala Leu Leu Glu Leu Glu Asn Gln Phe Asn Glu Thr Asn
1               5                   10                  15

Arg Leu Leu His Ile Lys Gln His Glu Glu Val Glu Lys Asp Lys Lys
            20                  25                  30

Ala Lys Gln Gln Lys Thr Leu Lys Gln Ser Asp Thr Lys Val Asp Leu
        35                  40                  45

Ser Asn Ile Asp Lys Glu Leu Asn His Gln Lys Ser Gln Val Glu Lys
    50                  55                  60

Met Ala Glu Gln Lys Gly Ile Thr Asn Glu Asp Lys Asp Ser Met Leu
65                  70                  75                  80

Lys Lys Ile Glu Asp Ile Arg Lys Gln Ala Gln Gln Ala Asp Lys Lys
                85                  90                  95

Glu Asp Ala Glu Val Lys Val Arg Glu Glu Leu Gly Lys Leu Phe Ser
            100                 105                 110

Ser Thr Lys Ala Gly Leu Asp Gln Glu Ile Gln Glu His Val Lys Lys
        115                 120                 125

Glu Thr Ser Ser Glu Glu Asn Thr Gln Lys Val Asp Glu His Tyr Ala
    130                 135                 140

Asn Ser Leu
145
```

(2) INFORMATION FOR SEQ ID NO: 13:

(i) SEQUENCE CHARACTERISTICS:
(A) LENGTH: 147 amino acids
(B) TYPE: amino acid
(C) STRANDEDNESS: single
(D) TOPOLOGY: Not Relevant (ii) MOLECULE TYPE: peptide (xi) SEQUENCE DESCRIPTION: SEQ ID NO: 13:

```
Asp Ser Asp Ala Leu Leu Glu Leu Glu Asn Gln Phe Asn Glu Thr Asn
1               5                   10                  15

Arg Leu Leu His Ile Lys Gln His Glu Glu Val Glu Lys Asp Lys Lys
            20                  25                  30

Ala Lys Gln Gln Lys Thr Leu Lys Gln Ser Asp Thr Lys Val Asp Leu
        35                  40                  45

Ser Asn Ile Asp Lys Glu Leu Asn His Gln Lys Ser Gln Val Glu Lys
    50                  55                  60

Met Ala Glu Gln Lys Gly Ile Thr Asn Glu Asp Lys Asp Ser Met Leu
```

```
65                  70                  75                  80

Lys Lys Ile Glu Asp Ile Arg Lys Gln Ala Gln Gln Ala Asp Lys Lys
                85                  90                  95

Glu Asp Ala Glu Val Lys Val Arg Glu Glu Leu Gly Lys Leu Phe Ser
            100                 105                 110

Ser Thr Lys Ala Gly Leu Asp Gln Glu Ile Gln Glu His Val Lys Lys
        115                 120                 125

Glu Thr Ser Ser Glu Glu Asn Thr Gln Lys Val Asp Glu His Tyr Ala
    130                 135                 140

Asn Ser Leu
145
```

(2) INFORMATION FOR SEQ ID NO: 14:

(i) SEQUENCE CHARACTERISTICS:
(A) LENGTH: 111 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 14:

```
Val Asp Leu Ser Asn Ile Asp Lys Glu Leu Asn His Gln Lys Ser Gln
1               5                   10                  15

Val Glu Lys Met Ala Glu Gln Lys Gly Ile Thr Asn Glu Asp Lys Asp
            20                  25                  30

Ser Met Leu Lys Lys Ile Glu Asp Ile Arg Lys Gln Ala Gln Gln Ala
        35                  40                  45

Asp Lys Lys Glu Asp Ala Glu Val Lys Val Arg Glu Glu Leu Gly Lys
    50                  55                  60

Leu Phe Ser Ser Thr Lys Ala Gly Leu Asp Gln Glu Ile Gln Glu His
65                  70                  75                  80

Val Lys Lys Glu Thr Ser Ser Glu Glu Asn Thr Gln Lys Val Asp Glu
                85                  90                  95

His Tyr Ala Asn Ser Leu Gln Asn Leu Ala Gln Lys Ser Leu Glu
            100                 105                 110
```

(2) INFORMATION FOR SEQ ID NO: 15:

(i) SEQUENCE CHARACTERISTICS:
(A) LENGTH: 111 amino acids
(B) TYPE: amino acid
(C) STRANDEDNESS: single
(D) TOPOLOGY: Not Relevant (ii) MOLECULE TYPE: peptide (xi) SEQUENCE DESCRIPTION: SEQ ID NO: 15:

```
Val Asp Leu Ser Asn Ile Asp Lys Glu Leu Asn His Gln Lys Ser Gln
1               5                   10                  15

Val Glu Lys Met Ala Glu Gln Lys Gly Ile Thr Asn Glu Asp Lys Asp
            20                  25                  30

Ser Met Leu Lys Lys Ile Glu Asp Ile Arg Lys Gln Ala Gln Gln Ala
        35                  40                  45

Asp Lys Lys Glu Asp Ala Glu Val Lys Val Arg Glu Glu Leu Gly Lys
    50                  55                  60

Leu Phe Ser Ser Thr Lys Ala Gly Leu Asp Gln Glu Ile Gln Glu His
65                  70                  75                  80
```

-continued

```
Val Lys Lys Glu Thr Ser Ser Glu Glu Asn Thr Gln Lys Val Asp Glu
                85                  90                  95

His Tyr Ala Asn Ser Leu Gln Asn Leu Ala Gln Lys Ser Leu Glu
            100                 105                 110
```

(2) INFORMATION FOR SEQ ID NO: 16:

(i) SEQUENCE CHARACTERISTICS:
(A) LENGTH: 120 amino acids
(B) TYPE: amino acid
(C) STRANDEDNESS: single
(D) TOPOLOGY: Not Relevant (ii) MOLECULE TYPE: peptide (xi) SEQUENCE DESCRIPTION: SEQ ID NO: 16:

```
Val Asp Leu Ser Asn Ile Asp Lys Glu Leu Asn His Gln Lys Ser Gln
1               5                   10                  15

Val Glu Lys Met Ala Glu Gln Lys Gly Ile Thr Asn Glu Asp Lys Asp
            20                  25                  30

Ser Met Leu Lys Lys Ile Glu Asp Ile Arg Lys Gln Ala Gln Gln Ala
        35                  40                  45

Asp Lys Lys Glu Asp Ala Glu Val Lys Val Arg Glu Glu Leu Gly Lys
    50                  55                  60

Leu Phe Ser Ser Thr Lys Ala Gly Leu Asp Gln Glu Ile Gln Glu His
65                  70                  75                  80

Val Lys Lys Glu Thr Ser Ser Glu Glu Asn Thr Gln Lys Val Asp Glu
                85                  90                  95

His Tyr Ala Asn Ser Leu Gln Asn Leu Ala Gln Lys Ser Leu Glu Glu
            100                 105                 110

Leu Asp Lys Ala Thr Thr Asn Glu
        115                 120
```

(2) INFORMATION FOR SEQ ID NO: 17:

(i) SEQUENCE CHARACTERISTICS:
(A) LENGTH: 120 amino acids
(B) TYPE: amino acid
(C) STRANDEDNESS: single
(D) TOPOLOGY: Not Relevant (ii) MOLECULE TYPE: peptide (xi) SEQUENCE DESCRIPTION: SEQ ID NO: 17:

```
Val Asp Leu Ser Asn Ile Asp Lys Glu Leu Asn His Gln Lys Ser Gln
1               5                   10                  15

Val Glu Lys Met Ala Glu Gln Lys Gly Ile Thr Asn Glu Asp Lys Asp
            20                  25                  30

Ser Met Leu Lys Lys Ile Glu Asp Ile Arg Lys Gln Ala Gln Gln Ala
        35                  40                  45

Asp Lys Lys Glu Asp Ala Glu Val Lys Val Arg Glu Glu Leu Gly Lys
    50                  55                  60

Leu Phe Ser Ser Thr Lys Ala Gly Leu Asp Gln Glu Ile Gln Glu His
65                  70                  75                  80

Val Lys Lys Glu Thr Ser Ser Glu Glu Asn Thr Gln Lys Val Asp Glu
                85                  90                  95

His Tyr Ala Asn Ser Leu Gln Asn Leu Ala Gln Lys Ser Leu Glu Glu
            100                 105                 110

Leu Asp Lys Ala Thr Thr Asn Glu
        115                 120
```

(2) INFORMATION FOR SEQ ID NO: 18:

(i) SEQUENCE CHARACTERISTICS:
(A) LENGTH: 58 amino acids
(B) TYPE: amino acid
(C) STRANDEDNESS: single
(D) TOPOLOGY: Not Relevant (ii) MOLECULE TYPE: peptide (xi) SEQUENCE DESCRIPTION: SEQ ID NO: 18:

```
Val Asp Leu Ser Asn Ile Asp Lys Glu Leu Asn His Gln Lys Ser Gln
1               5                   10                  15

Val Glu Lys Met Ala Glu Gln Lys Gly Ile Thr Asn Glu Asp Lys Asp
            20                  25                  30

Ser Met Leu Lys Lys Ile Glu Asp Ile Arg Lys Gln Ala Gln Gln Ala
        35                  40                  45

Asp Lys Lys Glu Asp Ala Glu Val Lys Val
    50                  55
```

(2) INFORMATION FOR SEQ ID NO: 19:

(i) SEQUENCE CHARACTERISTICS:
(A) LENGTH: 58 amino acids
(B) TYPE: amino acid
(C) STRANDEDNESS: single
(D) TOPOLOGY: Not Relevant (ii) MOLECULE TYPE: peptide (xi) SEQUENCE DESCRIPTION: SEQ ID NO: 19:

```
Val Asp Leu Ser Asn Ile Asp Lys Glu Leu Asn His Gln Lys Ser Gln
1               5                   10                  15

Val Glu Lys Met Ala Glu Gln Lys Gly Ile Thr Asn Glu Asp Lys Asp
            20                  25                  30

Ser Met Leu Lys Lys Ile Glu Asp Ile Arg Lys Gln Ala Gln Gln Ala
        35                  40                  45

Asp Lys Lys Glu Asp Ala Glu Val Lys Val
    50                  55
```

(2) INFORMATION FOR SEQ ID NO: 20:

(i) SEQUENCE CHARACTERISTICS:
(A) LENGTH: 102 amino acids
(B) TYPE: amino acid
(C) STRANDEDNESS: single
(D) TOPOLOGY: Not Relevant (ii) MOLECULE TYPE: peptide (xi) SEQUENCE DESCRIPTION: SEQ ID NO: 20:

```
Val Asp Leu Ser Asn Ile Asp Lys Glu Leu Asn His Gln Lys Ser Gln
1               5                   10                  15

Val Glu Lys Met Ala Glu Gln Lys Gly Ile Thr Asn Glu Asp Lys Asp
            20                  25                  30

Ser Met Leu Lys Lys Ile Glu Asp Ile Arg Lys Gln Ala Gln Gln Ala
        35                  40                  45

Asp Lys Lys Glu Asp Ala Glu Val Lys Val Arg Glu Glu Leu Gly Lys
    50                  55                  60

Leu Phe Ser Ser Thr Lys Ala Gly Leu Asp Gln Glu Ile Gln Glu His
65                  70                  75                  80
```

-continued

```
Val Lys Lys Glu Thr Ser Ser Glu Glu Asn Thr Gln Lys Val Asp Glu
            85                  90                  95

His Tyr Ala Asn Ser Leu
            100
```

(2) INFORMATION FOR SEQ ID NO: 21:

(i) SEQUENCE CHARACTERISTICS:
(A) LENGTH: 78 amino acids
(B) TYPE: amino acid
(C) STRANDEDNESS: single
(D) TOPOLOGY: Not Relevant (ii) MOLECULE TYPE: peptide (xi) SEQUENCE DESCRIPTION: SEQ ID NO: 21:

```
Val Asp Leu Ser Asn Ile Asp Lys Glu Leu Asn His Gln Lys Ser Pro
1               5                   10                  15

Val Glu Lys Met Ala Glu Pro Lys Gly Ile Thr Asn Glu Asp Lys Asp
            20                  25                  30

Ser Met Leu Lys Lys Ile Glu Asp Ile Arg Lys Gln Ala Gln Gln Ala
        35                  40                  45

Asp Lys Lys Glu Asp Ala Glu Val Lys Val Arg Glu Glu Leu Gly Lys
    50                  55                  60

Leu Phe Ser Ser Thr Lys Ala Gly Leu Asp Gln Glu Ile Gln
65                  70                  75
```

(2) INFORMATION FOR SEQ ID NO: 22:

(i) SEQUENCE CHARACTERISTICS:
(A) LENGTH: 78 amino acids
(B) TYPE: amino acid
(C) STRANDEDNESS: single
(D) TOPOLOGY: Not Relevant (ii) MOLECULE TYPE: peptide (xi) SEQUENCE DESCRIPTION: SEQ ID NO: 22:

```
Val Asp Leu Ser Asn Ile Asp Lys Glu Leu Asn His Gln Lys Ser Gln
1               5                   10                  15

Val Glu Ala Met Ala Glu Gln Ala Gly Ile Thr Asn Glu Asp Lys Asp
            20                  25                  30

Ser Met Leu Lys Lys Ile Glu Asp Ile Arg Lys Gln Ala Gln Gln Ala
        35                  40                  45

Asp Lys Lys Glu Asp Ala Glu Val Lys Val Arg Glu Glu Leu Gly Lys
    50                  55                  60

Leu Phe Ser Ser Thr Lys Ala Gly Leu Asp Gln Glu Ile Gln
65                  70                  75
```

(2) INFORMATION FOR SEQ ID NO: 23:

(i) SEQUENCE CHARACTERISTICS:
(A) LENGTH: 72 amino acids
(B) TYPE: amino acid
(C) STRANDEDNESS: single
(D) TOPOLOGY: Not Relevant (ii) MOLECULE TYPE: peptide (xi) SEQUENCE DESCRIPTION: SEQ ID NO: 23:

```
Val Asp Leu Ser Asn Ile Asp Lys Glu Leu Asn His Gln Lys Ser Gln
1               5                   10                  15

Glu Ala Gly Ile Thr Asn Glu Asp Lys Asp Ser Met Leu Lys Lys Ile
```

-continued

```
            20                  25                  30

Glu Asp Ile Arg Lys Gln Ala Gln Gln Ala Asp Lys Lys Glu Asp Ala
        35                  40                  45

Glu Val Lys Val Arg Glu Glu Leu Gly Lys Leu Phe Ser Ser Thr Lys
    50                  55                  60

Ala Gly Leu Asp Gln Glu Ile Gln
65                  70
```

(2) INFORMATION FOR SEQ ID NO: 24:

(i) SEQUENCE CHARACTERISTICS:
(A) LENGTH: 78 amino acids
(B) TYPE: amino acid
(C) STRANDEDNESS: single
(D) TOPOLOGY: Not Relevant (ii) MOLECULE TYPE: peptide (xi) SEQUENCE DESCRIPTION: SEQ ID NO: 24:

```
Val Asp Leu Ser Asn Ile Asp Lys Glu Leu Asn His Gln Lys Ser Gln
1               5                   10                  15

Val Glu Thr Met Ala Glu Gln Leu Gly Ile Thr Asn Glu Asp Lys Asp
            20                  25                  30

Ser Met Leu Lys Lys Ile Glu Asp Ile Arg Lys Gln Ala Gln Gln Ala
        35                  40                  45

Asp Lys Lys Glu Asp Ala Glu Val Lys Val Arg Glu Glu Leu Gly Lys
    50                  55                  60

Leu Phe Ser Ser Thr Lys Ala Gly Leu Asp Gln Glu Ile Gln
65                  70                  75
```

(2) INFORMATION FOR SEQ ID NO: 25:

(i) SEQUENCE CHARACTERISTICS:
(A) LENGTH: 9 amino acids
(B) TYPE: amino acid
(C) STRANDEDNESS: single
(D) TOPOLOGY: Not Relevant (ii) MOLECULE TYPE: peptide (xi) SEQUENCE DESCRIPTION: SEQ ID NO: 25:

```
Glu Leu Ile Lys Ser Ala Gln Gln Glu
1               5
```

(2) INFORMATION FOR SEQ ID NO: 26:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 26:

```
GTTGAAGCAA TGGCAGAGCA AGCGGGAATC ACAAATGAAG                          40
```

(2) INFORMATION FOR SEQ ID NO: 27:

(i) SEQUENCE CHARACTERISTICS:
(A) LENGTH: 42 base pairs
(B) TYPE: nucleic acid
(C) STRANDEDNESS: single
(D) TOPOLOGY: Not Relevant (ii) MOLECULE TYPE: cDNA (xi) SEQUENCE DESCRIPTION: SEQ ID NO: 27:

```
GATTCCCGCT TGCTCTGCCA TTGCTTCAAC TTGACTTTTT TG                    42
```

(2) INFORMATION FOR SEQ ID NO: 28:

(i) SEQUENCE CHARACTERISTICS:
(A) LENGTH: 30 base pairs
(B) TYPE: nucleic acid
(C) STRANDEDNESS: single
(D) TOPOLOGY: Not Relevant (ii) MOLECULE TYPE: cDNA (xi) SEQUENCE DESCRIPTION: SEQ ID NO: 28:

```
AAGGATCCAA GTGAGCTTGT AAAGGACGAT                                  30
```

(2) INFORMATION FOR SEQ ID NO: 29:

(i) SEQUENCE CHARACTERISTICS:
(A) LENGTH: 32 base pairs
(B) TYPE: nucleic acid
(C) STRANDEDNESS: single
(D) TOPOLOGY: Not Relevant (ii) MOLECULE TYPE: cDNA (xi) SEQUENCE DESCRIPTION: SEQ ID NO: 29:

```
AAAACTCGAG TTTCTTTTCC GTTGTTGATG TA                               32
```

(2) INFORMATION FOR SEQ ID NO: 30:

(i) SEQUENCE CHARACTERISTICS:
(A) LENGTH: 15 amino acids
(B) TYPE: amino acid
(C) STRANDEDNESS: single
(D) TOPOLOGY: linear (ii) MOLECULE TYPE: cDNA (xi) SEQUENCE DESCRIPTION: SEQ ID NO: 30:

```
Asn His Gln Lys Ser Gln Val Glu Lys Met Ala Glu Gln Lys Gly
1               5                   10                  15
```

(2) INFORMATION FOR SEQ ID NO: 31:

(i) SEQUENCE CHARACTERISTICS:
(A) LENGTH: 57 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 1..54

(xi) SEQUENCE DESCRIPTION: SEQ ID NO: 31:

```
AGA TCT CGA TCC CGC GAA ATT AAT ACG ACT CAC TAT AGG GGA ATT GTG       48
Arg Ser Arg Ser Arg Glu Ile Asn Thr Thr His Tyr Arg Gly Ile Val
  1               5                  10                  15

AGC GGA TAA                                                           57
Ser Gly
```

(2) INFORMATION FOR SEQ ID NO: 32:

-continued

```
    (i) SEQUENCE CHARACTERISTICS:
         (A) LENGTH: 18 amino acids
         (B) TYPE: amino acid
         (D) TOPOLOGY: linear

   (ii) MOLECULE TYPE: protein

   (xi) SEQUENCE DESCRIPTION: SEQ ID NO: 32:

Arg Ser Arg Ser Arg Glu Ile Asn Thr Thr His Tyr Arg Gly Ile Val
  1               5                  10                  15

Ser Gly


(2) INFORMATION FOR SEQ ID NO: 33:

    (i) SEQUENCE CHARACTERISTICS:
         (A) LENGTH: 30 base pairs
         (B) TYPE: nucleic acid
         (C) STRANDEDNESS: double
         (D) TOPOLOGY: linear

   (ii) MOLECULE TYPE: cDNA

   (ix) FEATURE:
         (A) NAME/KEY: CDS
         (B) LOCATION: 1..27

   (xi) SEQUENCE DESCRIPTION: SEQ ID NO: 33:

CAA TTC CCC TCT AGA AAT AAT TTT GTT TAA                                    30
Gln Phe Pro Ser Arg Asn Asn Phe Val
  1               5


(2) INFORMATION FOR SEQ ID NO: 34:

    (i) SEQUENCE CHARACTERISTICS:
         (A) LENGTH: 9 amino acids
         (B) TYPE: amino acid
         (D) TOPOLOGY: linear

   (ii) MOLECULE TYPE: protein

   (xi) SEQUENCE DESCRIPTION: SEQ ID NO: 34:

Gln Phe Pro Ser Arg Asn Asn Phe Val
  1               5
```